United States Patent [19]

Godowski et al.

[11] Patent Number: 5,914,237

[45] Date of Patent: *Jun. 22, 1999

[54] KINASE RECEPTOR ACTIVATION ASSAY

[75] Inventors: Paul J. Godowski; Melanie R. Mark, both of Burlingame; Michael D. Sadick, El Cerrito; Wai Lee Tan Wong, Los Altos, all of Calif.

[73] Assignee: Genentech Incorporated, South San Francisco, Calif.

[ * ] Notice: This patent is subject to a terminal disclaimer.

[21] Appl. No.: 08/440,816

[22] Filed: May 15, 1995

Related U.S. Application Data

[63] Continuation of application No. 08/286,305, Aug. 5, 1994, which is a continuation-in-part of application No. 08/170,558, Dec. 20, 1993, which is a continuation of application No. 08/157,563, Nov. 23, 1993, abandoned.

[51] Int. Cl.$^6$ ...................... G01N 33/567; G01N 33/573; C12Q 1/48
[52] U.S. Cl. .................... 435/7.21; 435/7.4; 435/7.94; 435/15; 436/501; 436/518; 436/531; 436/548; 530/388.22; 530/388.26; 530/389.6
[58] Field of Search ..................... 435/7.21, 7.4, 435/7.94, 15; 436/501, 518, 531, 548; 530/388.22, 388.26, 389.6

[56] References Cited

U.S. PATENT DOCUMENTS 4,859,609 8/1989 Dull et al. ............................ 436/501

FOREIGN PATENT DOCUMENTS

| 244221 | 11/1987 | European Pat. Off. . |
| WO 93/15201 | 5/1993 | WIPO . |
| WO 94/19463 | 1/1994 | WIPO . |

OTHER PUBLICATIONS

Cleaveland et al., "A Microtiter–Based Assay for the Detection of Protein Tyrosine Kinase Activity" *Analytical Biochemistry* 190:249–253 (1990).

Corfas et al., "ARIA, a protein that stimulates acetylcholine receptor synthesis, also induces tyrosine phosphorylation of a 185–kDa muscle transmembrane protein" *Proc. Natl. Acad. Sci. USA* 90:1624–1628 (Feb. 1993).

Dijke et al., "Serine/Threonine Kinase Receptors" *Progress in Growth Factor Research* 5:55–72 (1994).

Donato et al., "Tumor Necrosis Factor Regulates Tyrosine Phosphorylation on Epidermal Growth Factor Receptors in A431 Carcinoma Cells: Evidence for a Distinct Mechanism" *Cell Growth and Differentiation* 3:259–268 (1992).

Fantl et al., "Signalling by Recptor Tyrosine Kinases" *Annual Review in Biochemistry* 62:453–481 (1993).

Fujimoto, "brt, A Mouse Gene Encoding a Novel Receptor–type Protein–Tyrosine Kinase, is Preferentially Expressed in the Brain" *Oncogene* 9:693–698 (1994).

GenBank, "Release 79" (along with hstyro3 and hstyro3y sequences available on GenBank) (Oct. 15, 1993).

Glenney et al., "Monoclonal antibodies to phosphotyrosine" *Journal of Immunological Methods* 109:277–285 (1988).

Hagino et al., "Enzyme–Linked Immunosorbent Assay Method for Human Autophosphorylated Insulin Receptor" *Diabetes* 43:274–280 (Feb. 1994).

Holmes et al., "Identification of heregulin, a specific activator of p185$^{erbB2}$" *Science* 256:1205–1210 (1992).

Hunter, "Protein Kinase Classification" *Methods in Enzymology* 200:3–9 (1991).

Hunter, "Synthetic Peptide Substrates for a Tyrosine Protein Kinase" *Journal of Biological Chemistry* 257(9):4843–4848 (1982).

Hunter et al., "Protein–Tyrosine Kinases" *Annual Review in Biochemistry* 54:897–930 (1985).

Kamps, "Generation and Use of Anti–Phosphotyrosine Antibodies for Immunoblotting" *Methods in Enzymology* 201:101–110 (1991).

Kasuga et al., "Insulin Stimulation of Phosphorylation of the /142 Subunit of the Insulin Receptor" *Journal of Biological Chemistry* 257(17):9891–9894 (1982).

Kasuga et al., "Phosphorylation of the Insulin Receptor in Cultured Hepatoma Cells and a Solubilized System" *Methods in Enzymology* 109:609–621 (1985).

(List continued on next page.)

*Primary Examiner*—Ponnathapura Achutamurthy
*Assistant Examiner*—P. Ponnaluri
*Attorney, Agent, or Firm*—Wendy M. Lee

[57] ABSTRACT

An assay for measuring activation (i.e., autophosphorylation) of a tyrosine kinase receptor of interest is disclosed.

(a) A first solid phase is coated with a substantially homogeneous population of cells so that the cells adhere to the first solid phase. The cells have either an endogenous tyrosine kinase receptor or have been transformed with DNA encoding a receptor or "receptor construct" and the DNA has been expressed so that the receptor or receptor construct is presented in the cell membranes of the cells.

(b) A ligand is then added to the solid phase having the adhering cells, such that the tyrosine kinase receptor is exposed to the ligand.

(c) Following exposure to the ligand, the adherent cells are solubilized, thereby releasing cell lysate.

(d) A second solid phase is coated with a capture agent which binds specifically to the tyrosine kinase receptor, or, in the case of a receptor construct, to the flag polypeptide.

(e) The cell lysate obtained in step (c) is added to the wells containing the adhering capture agent so as to capture the receptor or receptor construct to the wells.

(f) A washing step is then carried out, so as to remove unbound cell lysate, leaving the captured receptor or receptor construct.

(g) The captured receptor or receptor construct is exposed to a labelled anti-phosphotyrosine antibody which identifies phosphorylated residues in the tyrosine kinase receptor.

(h) Binding of the anti-phosphotyrosine antibody to the captured receptor or receptor construct is measured.

29 Claims, 67 Drawing Sheets

OTHER PUBLICATIONS

King et al., "High throughput assay for inhibitors of the epidermal growth factor receptor–associated tyrosine kinase" *Life Sciences* 53:1465–1472 (1993).

Klein et al., "A mecrotiter well assay system to measure insulin activation of insulin receptor kinase in intact human mononuclear cells" *Diabetes* 42:883–890 (Jun. 1, 1993).

Knutson et al., "Comparison of insulin receptor tyrosine phosphorylation under in vitro and in situ conditions: assessment of specific protein tyrosine phosphorylation with the use of $_{32}$P–phosphate–labeled substrates" *Archives of Biochemistry & Biophysics* 285(2):197–204, 1991.

Kozma et al., "Comparison of Three Methods for Detecting Tyrosine–Phosphorylated Proteins" *Methods in Enzymology* 201:28–43 (1991).

Lai et al. "An Extended Family of Protein–Tyrosine Kinase Genes Differentially Expressed in the Vertebrate Nervous System" *Neuron* 6:691–704 (May 1991).

Lai et al., "Structure, expression, and activity of Tyro 3, a neural adhesion–related receptor tyrosine kinase" *Oncogene* 9:2567–2578 (1994).

Lazaro et al., "Description of an Enzyme–Linked Immunosorbent Assay for the Detection of Protein Tyrosine Kinase" *Analytical Biochemistry* 192:257–261 (1991).

Madden et al., "Two Nonradioactive Assays for Phosphotyrosine Phosphatases with Activity toward the Insulin Receptor" *Annual of Biochemistry* 199:210–215 (1991).

Mark et al., "rse, a Novel Receptor–type Tyrosine Kinase with Homology to Axl/Ufo, Is Expressed at High Levels in the Brain" *Journal of Biological Chemistry* 269(14):10720–10728 (Apr. 8, 1994).

Mathews, "Activin Receptors and Cellular Signaling by the Receptor Serine Kinase Family" *Endocrine Review* 15(3):310–325 (1994).

O'Bryan et al., "axl, a transforming gene isolated from primary human myeloid leukemia cells, encodes a novel receptor tyrosine kinase" *Molecular & Cellular Biology* 11:5016–5031 (1991).

Ohashi et al., "Cloning of the cDNA for a Novel Receptor Tyrosine Kinase, Sky, Predominantly Expressed in Brain" *Oncogene* 9:699–705 (1994).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Pazin et al., "Triggering Signaling Cascades by Receptor Tyrosine Kinases" *TIBS* 17:374–378 (1992).

Pike, "Assay of Growth Factor–Stimulated Tyrosine Kinases Using Synthetic Peptide Substrates" *Methods of Enzymology* 146:353–362 (1987).

Polvi et al., "The Human TYRO3 Gene and Pseudogene are Located in Chromosome 15q14–q25" *Gene* 134:289–293 (1993).

Sale, "Serine/threonine kinases and tyrosine phosphatases that act on the insulin receptor" *Biochemical Society Transactions* 20:664–670 (1992).

Stark et al., "FGFR–4, a new member of the fibroblast growth factor receptor family, expressed in the definitive endoderm and skeletal muscle lineages of the mouse" *Development* 113:641–651 (1991).

Ullrich and Schlessinger, "Signal Transduction by Receptors with Tyrosine Kinase Activity" *Cell* 61:203–212 (Apr. 1990).

Wang, "Isolation of Antibodies for Phosphotyrosine by Immunization with a v–abl Oncogene–Encoded Protein" *Molecular & Cellular Biology* 5(12):3640–3643 (1985).

Wang et al., "Evidence for Association of the Cloned Liver Growth Hormone Receptor with a Tyrosine Kinase" *Journal of Biological Chemistry* 267(24):17390–17396 (1992).

White et al., "Preparation and Use of Anti–Phosphotyrosine Antibodies to Study Structure and Function of Insulin Receptor" *Methods in Enzymology* 201:65–79 (1991).

Wilks et al., "The Application of the polymerase chain reaction to cloning members of the protein tyrosine kinase family" *Gene* 85:67–74 (1989).

Paborsky et al, Protein Engineering. vol. 3. No. 6 547–553, 1990.

Meloche et al. Molecular Biology of the Cell. vol. 3, 63–71. Jan. 1992.

Fendly et al. Journal of Biological Response Modifiers 9:449–455, 1990.

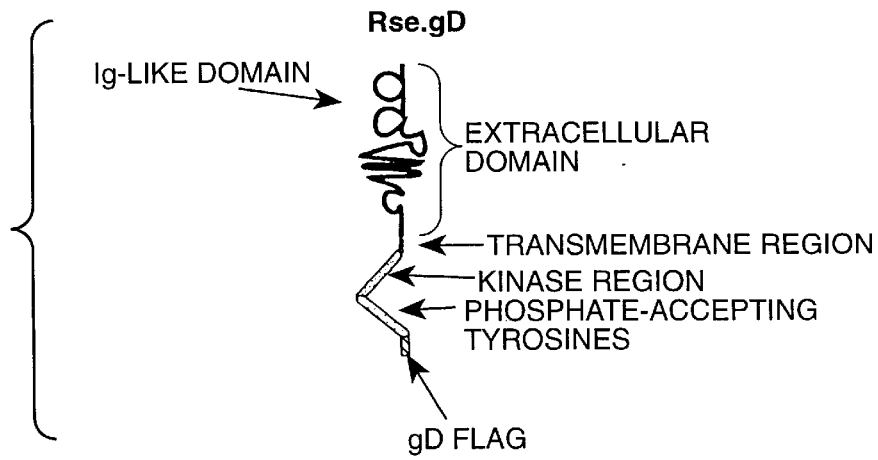
FIG._1A
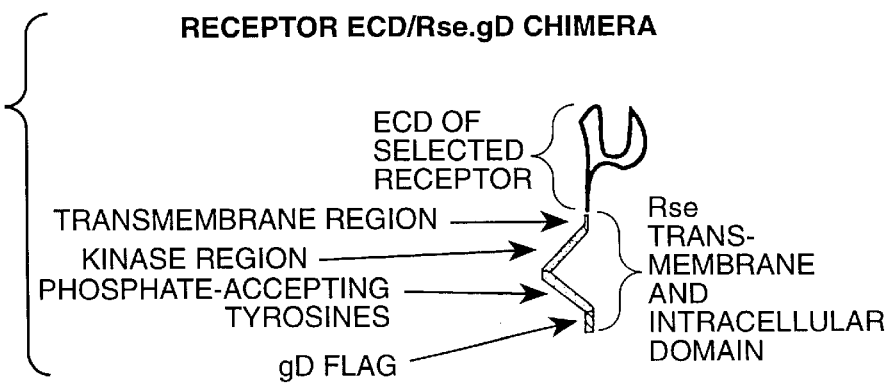
FIG._1B
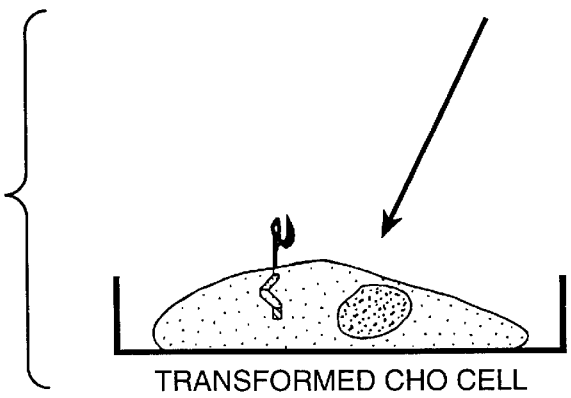
FIG._1C

FIG._2A

```
         *   *   *   *   *   *   *   *   *   *   *   *   *   *   *   *   *   *
signal sequence                                                                    * L
   *   *   *   *   *   *   *   *   *   *   *   *   *   *   *   *   *   *   *   * L
   * M   A   L   R   R   S   M   G   R   P   G   L   P   P   P   P   R   L   G   L A A L A S L L
 1 ATGGGCCTGA GGCGGAGCAT GGGGCGGCCG GGGGGGCTCCCG CGCTGCCGCT CCGGCGCTCG GCTGCTGCT GGGGGCTCTG GCTTCTCTGC
                          extracellular domain
   *   *   *   * * *
   * L   P   E   S   A   A   A   G   L   K   L   M   G   A   P   V   K   L   T   V   S   Q   G   Q   P   V   K   L   N   C   S   V   E
101 TGCTCCCCGGA GTCCGCCGCC AGCCATGGG GCAGGTCTGA AGCTCATGGG AGCCCCGGTG AAGCTGACAG TGTCTCAGGG GCAGCCGGTG AAGCTCAACT GCAGTGTGGA 35 G   M   E   E   P   D   I   Q   W   V   K   D   G   A   V   V   Q   N   L   D   Q   L   Y   I   P   V   S   E   Q   H   W   I   G
 201 GGGGATGGAG GAGCCTGACA TCCAGTGGGT GAAGGATGGG GCTGTGGTCC AGAACTTGGA CCAGTTGTAC ATCCCAGTCA GCGAGCAGCA CTGGATCGGC 68 F   L   S   L   K   S   V   E   R   S   D   A   G   R   Y   W   C   Q   V   E   D   G   G   E   T   E   I   S   Q   P   V   W   L   T
 301 TTCCTCAGCC TGAAGTCAGT GGAGCGCTCT GACGCCGGCC GGTACTGGTG CCAGGTGGTG GATGGGGGTG AAACCGAGAT CTCCCAGCCA GTGTGGCTCA 101 V   E   G   V   P   F   F   T   V   E   P   K   D   L   A   V   P   P   N   A   P   F   Q   L   S   C   E   A   V   G   P   P   E
 401 GTGGAGGGAG TGCCATTT TTCACAGTGG AGCCCAAAGA TCTGGCAGTG CCCCCCAATG CCCCCTTTCA ACTGTCTTGT GAGGCTGTGG GTCCCCCTGA 135 P   V   T   I   V   W   W   R   G   T   K   I   G   G   P   A   P   S   P   S   V   L   N   V   T   G   V   T   Q   S   T   M
 501 CCGGTAGAAGG TGTGCCATTT ATTGTCTGGT GGAGAGGAAC TACGAAGATC GGGGGACCCG CTCCCCTCCC ATCTGTTTTA AATGTAACAG GGTGACCCAG AGCACCATG 168 F   S   C   E   A   H   N   L   K   G   L   A   S   S   R   T   A   T   V   H   L   Q   A   L   P   A   A   P   F   N   I   T   V   T
 601 TTTTCCTGTG AAGCTCACAA CCTAAAAGGC CTGGCCTCTT CTCGCACAGC CACTGTTCAC CTTCAAGCAC TGCCTGCAGC CCCCTTCAAC ATCACCGTGA 201 K   L   S   S   N   A   S   V   A   W   M   P   G   A   D   G   R   A   L   L   Q   S   C   T   V   Q   V   T   Q   A   P   G
 701 AAAGCTTTC CAGCAGCAAC GCTAGTGTGG CCTGGATGCC AGGTGCTGAT GGCCGAGCTC TGCTACAGTC CTGTACAGTT CAGGTGACAC AGGCCCCAGG 235 G   W   E   V   L   A   V   V   V   P   F   T   C   L   L   R   D   L   V   P   A   T   N   Y   S   L   R   V   R   C
 801 AGGCTGGGAA GTCCTGGCTG TTGTGGTCCC TGTGCCCCCC TTTACCTGCC TGCTCCGGGA CCTGGTGCCT GCCACCAACT ACAGCCTCAG GGTGCGCTGT 268 A   N   A   L   G   P   S   P   Y   A   D   W   V   P   F   Q   T   K   G   L   A   P   A   S   A   P   Q   N   L   H   A   I   R   T
 901 GCCAATGCCT TGGGGCCCTC TCCCTATGCT GACTGGGTGC CCTTTCAGAC CAAGGTCTA GCCCCAGCCA GCCCTCCCCA AAACCTCCAT GCCATCCGCA 301 D   S   G   L   I   L   E   W   E   E   V   I   P   E   A   P   L   E   G   P   L   G   P   Y   K   L   S   W   V   Q   D   N   G
1001 CAGATTCAGG CCTCATCTTG GAGTGGGAAG AAGTGATCCC CGAGGCCCCT TTGGAAGGCC CCCTGGGACC CTACAAACTG TCCTGGGTTC AAGACAATGG
```

FIG._2B

```
368  T   Q   D   E   L   T   V   E   G   T   R   A   N   L   T   G   W   D   P   Q   K   D   L   I   V   R   V   C   V   S   N   A   V
1101 AACCCAGGAT GAGCTGACAG TGGAGGGGAC CAGGGCCAAT TTGACAGGCT GGGATCCCCA AAAGGACCTG ATCGTACGTG TGTGGTCTC CAATGCAGTT
                                                                                                transmembrane domain
401  G   C   G   P   W   S   Q   P   L   V   V   S   S   H   D   R   A   G   Q   Q   G   P   P   H   S   R   T   S   W   V   P   V   V   L
1201 GGCTGTGGAC CCTGGAGTCA GCCACTGGTG GTCTCTTCTC ATGACCGTGC AGGCCAGCAG GGCCCTTCCTC ACAGCCCGAC ATCCTGGGTA CCTGTGGTCC 435  G   V   L   T   A   L   V   T   A   A   A   L   I   L   L   R   K   R   R   K   E   T   R   F   G   Q   A   F   D   S   V
1301 TTGGTGTGCT AACGGCCCTG GTGACGGCTG CTGCCCTGGC CCTCATCCTG CTTCGAAAGA GACGGAAAGA GACGCGGTTT GGGCAAGCCT TTGACAGTGT
                                                intracellular domain 468  M   A   R   G   E   P   A   V   H   F   R   A   A   R   S   F   N   R   E   R   P   E   R   I   E   A   T   L   D   S   L   G   I
1401 CATGGCCCGG GGAGACCAG CCGTTCACTT CCGGGCAGCC CGGTCCTTCA ATCGAGAAAG GCCCGAGCGC ATCGAGGCCA CATTGGACAG CTTGGGCATC 501  S   D   E   L   K   E   K   L   E   D   V   L   I   P   E   Q   Q   F   T   L   G   R   M   L   G   K   G   E   F   G   S   V   R   E
1501 AGCGATGAAC TAAAGGAAAA ACTGGAGGAT GTGCTCATCC CAGAGCAGCA GTTCACCCTG GGCCGGATGT TGGGCAAAGG AGAGTTTGGT TCAGTGCGGG 535  A   Q   L   K   Q   E   D   G   S   F   V   K   V   A   V   K   M   L   K   A   D   I   I   A   S   S   D   I   E   E   F   L   R
1601 AGGCCCAGCT GAAGCAAGAG GATGGCTCCT TTGTGAAAGT GGCTGTGAAG ATGCTGAAAG CTGACATCAT TGCCTCAAGC GACATTGAAG AGTTCCTCAG 568  E   A   A   C   M   K   E   F   D   H   P   H   V   A   K   L   V   G   V   S   L   R   S   R   A   K   G   R   L   P   I   P   M
1701 GGAAGCAGCT TGCATGAAGG AGTTTGACCA TCCACACGTG GCCAAACTTG TGGGGTAAG CCTCCGGAGC AGGGCTAAAG GCCGTCTCCC CATCCCCATG 601  V   I   L   P   F   M   K   H   G   D   L   H   A   F   L   L   A   S   R   I   G   E   N   P   F   N   L   P   L   Q   T   L   I   R
1801 GTCATCTTGC CCTTCATGAA GCATGGGGAC CTGCATGCCT TCCTGCTCGC CTCCCGGATT GGGGAGAACC CCTTTAACCT ACCCCTCCAG ACCCTGATCC 635  F   M   V   D   I   A   C   G   M   E   Y   L   S   S   R   N   F   I   H   R   D   L   A   A   R   N   C   M   L   A   E   D   M
1901 GGTTCATGGT GGACATTGCC TGCGGGCATG GAGTACCTGA GTAGCCGGAA CTTCATCCAC CGAGACCTGG CTGCTCGGAAT TGCATGCTGG CAGAGACAT 668  T   V   C   V   A   D   F   G   L   S   R   K   I   Y   S   G   D   Y   Y   R   Q   G   C   A   S   K   L   P   V   K   W   L   A
2001 GACAGTGTGT GTGGCTGACT TCGGACTCTC CCGGAAGATC TACAGTGGGG ACTACTATCG TCAAGGCTGT GCCTCCAAAC TGCCTGTCAA GTGGCTGGCC
```

FIG._2C

```
701  L  E  S  L     A  D  N     L  Y  T     V  Q  S  D     V  W  A     F  G  V     T  M  W  E     I  M  T     R  G  Q     T  P  Y  A
2101 CTGGAGAGCC TGGCCGACAA CCTGTATACT GTGCAGAGTG ACGTGTGGGC GTTCGGGGTG ACCATGTGGG AGATCATGAC ACGTGGGCAG ACGCCATATG

735  G  I  E     N  A  E     I  Y  N  Y     L  I  G     G  N  R     L  K  Q  P     P  E  C     M  E  D     V  Y  D  L     M  Y  Q
2201 CTGGCATCGA AAACGCTGAG ATTTACAACT ACCTCATTGG CGGGAACCGC CTGAAACAGC CTCCGGAGTG TATGGAGGAC GTGTATGATC TCATGTACCA

768  C  W  S     A  D  P  K     Q  R  P     S  F  T     C  L  R  M     E  L  E     N  I  L     G  Q  L  S     V  L  S     A  S  Q
2301 GTGCTGGAGT GCTGACCCCA AGCAGCGCCC GAGCTTTACT TGTCTGCGAA TGGAACTGGA GAACATCTTG GGCCAGCTGT CTGTGCTATC TGCCAGCCAG

801  D  P  L  Y     I  N  I     E  R  A     E  E  P  T     A  G  G     S  L  E     L  P  G  R     D  Q  P     Y  S  G     A  G  D  G
2401 GACCCCTTAT ACATCAACAT CGAGAGAGCT GAGGAGCCCA CTGCGGGAGG CAGCCTGGAG CTACCTGGCA GGGATCAGCC CTACAGTGGG GCTGGGGATG

835  S  G  M     G  A  V     G  G  T  P     S  D  C     R  Y  I     L  T  P  G     G  L  A     E  Q  P     G  Q  A  E     H  Q  P
2501 GCAGTGGCAT GGGGGCAGTG GGTGGCACTC CCAGTGACTG TCGGTACATA CTCACCCCCG GAGGGCTGGC TGAGCAGCCA GGGCAGGCAG AGCACCAGCC gD flag polypeptide
868  E  S  P     L  N  E  T     Q  R  L     L  L  L     Q  Q  G  L     L  P  H     S  S  C        A  D  A  S     L  K  M     A  D  P
2601 AGAGAGTCCC CTCAATGAGA CACAGAGGCT TTTGCTGCTG CAGCAAGGGC TACTGCCACA CTCGAGCTGC GCAGATGCTA GCCTCAAGAT GGCTGATCCA 901  N  R  F  R     G  K  D     L  P  V     L  Q
2701 AATCGATTCC GGGGCAAAGA TCTTCCCGGTC CTGTAGAAGC TT
```

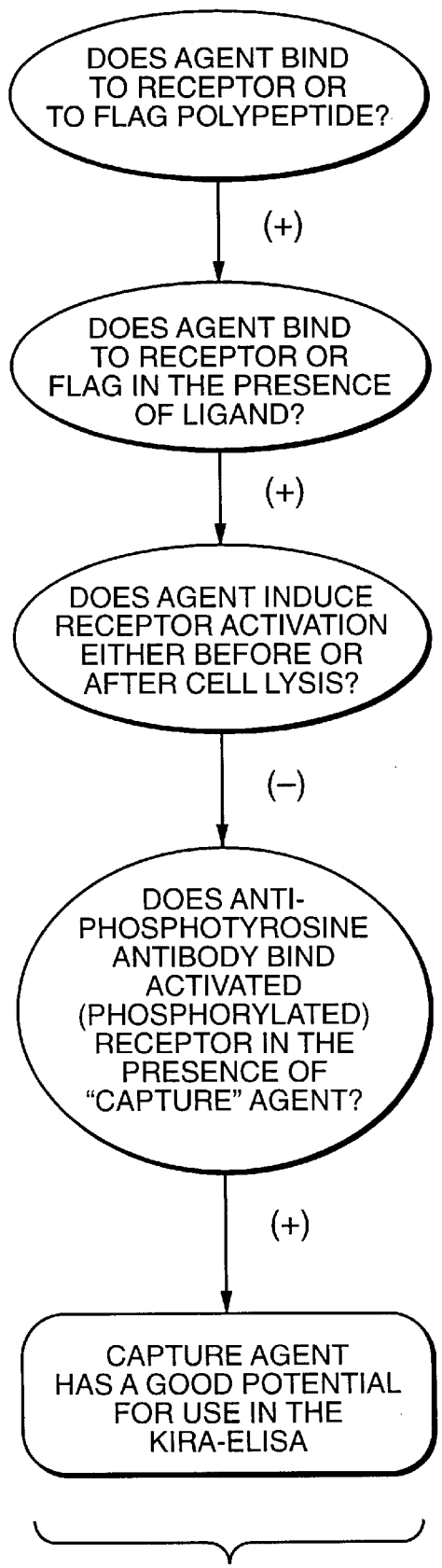
FIG._3

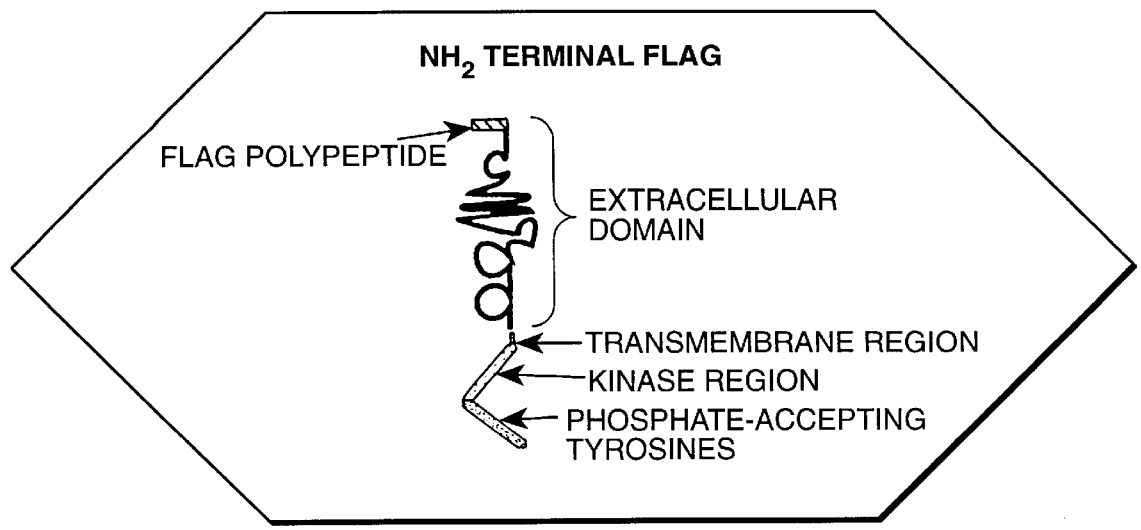
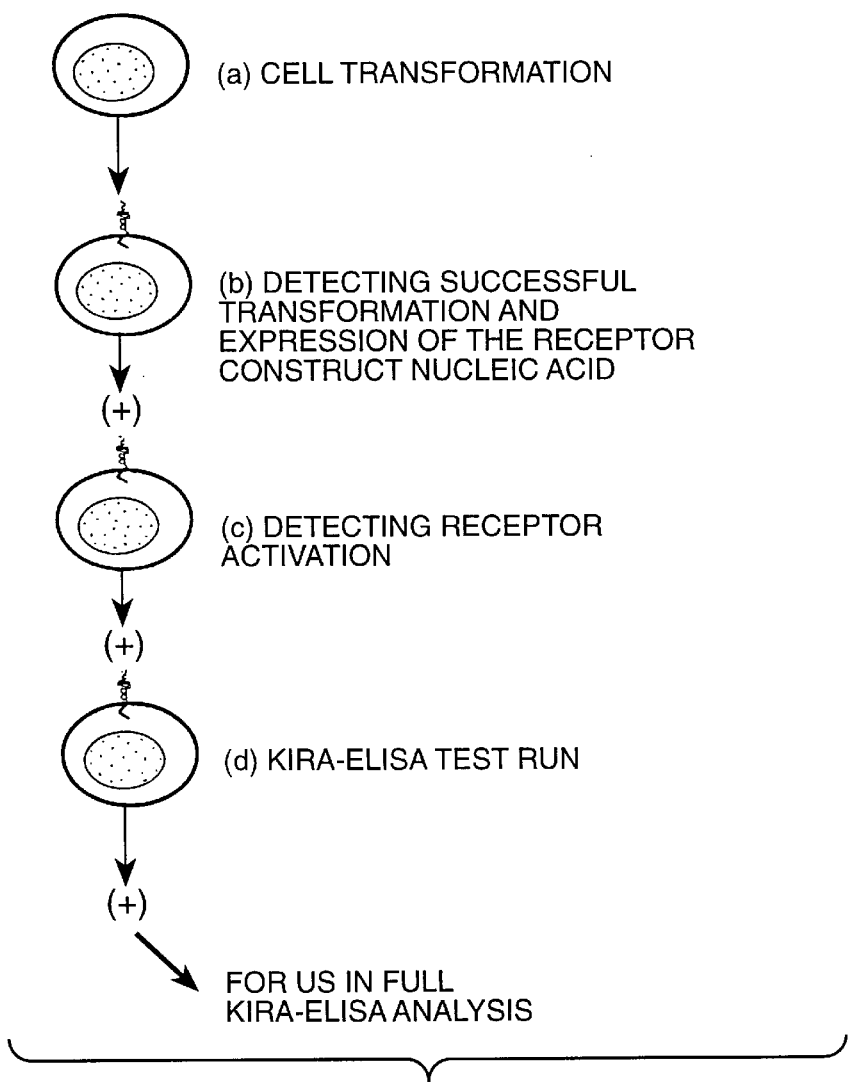
FIG._4

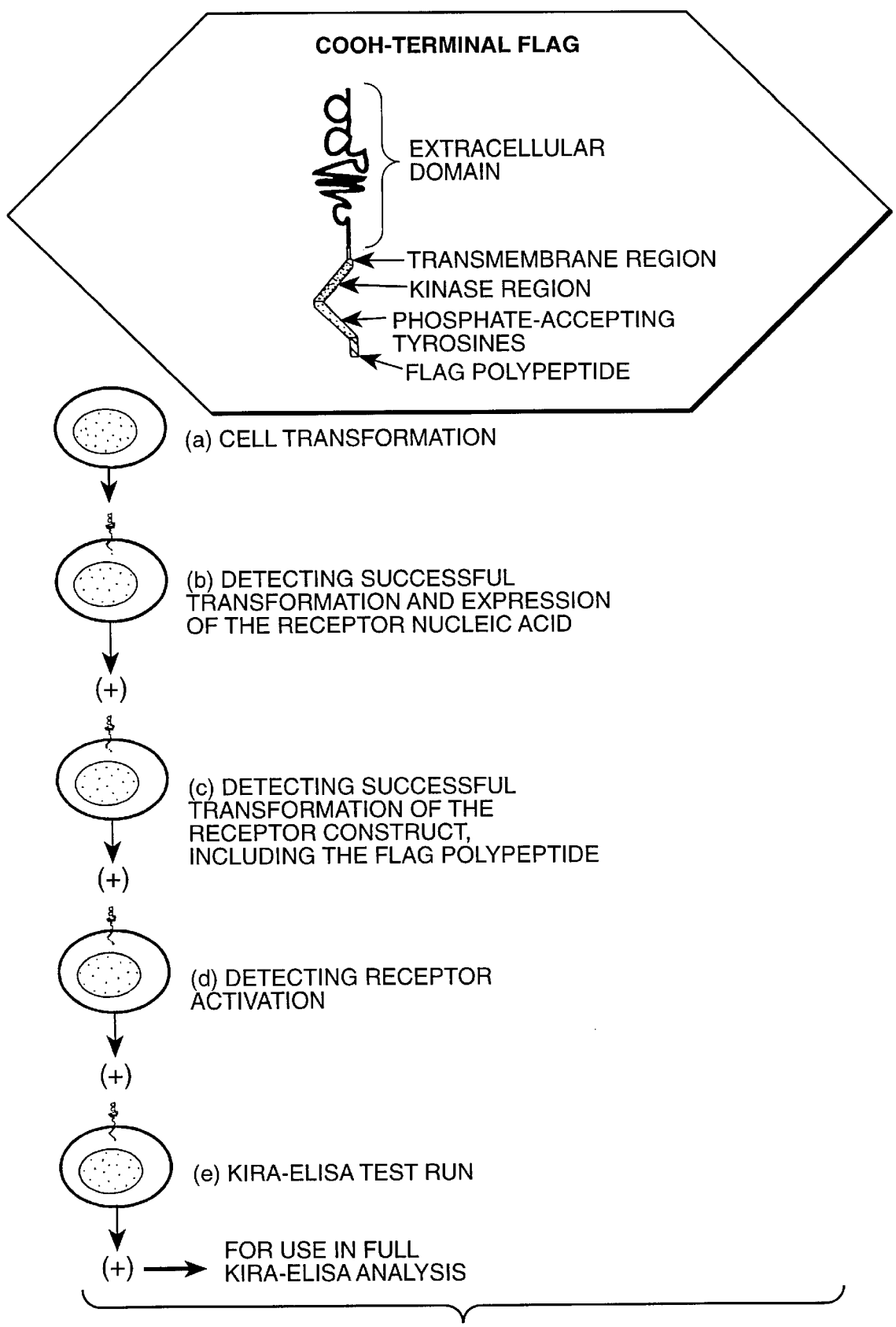
FIG._5

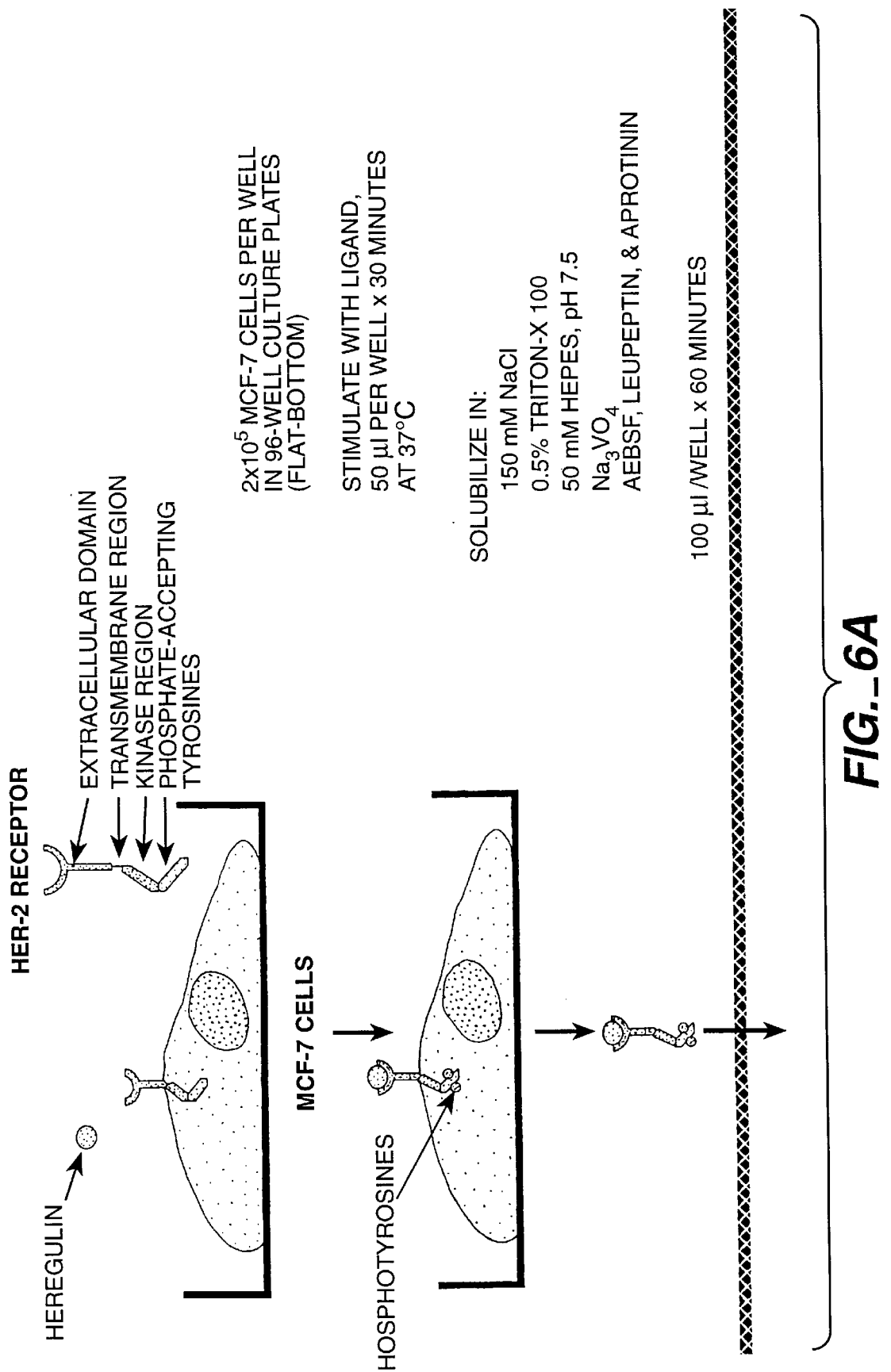
FIG._6A

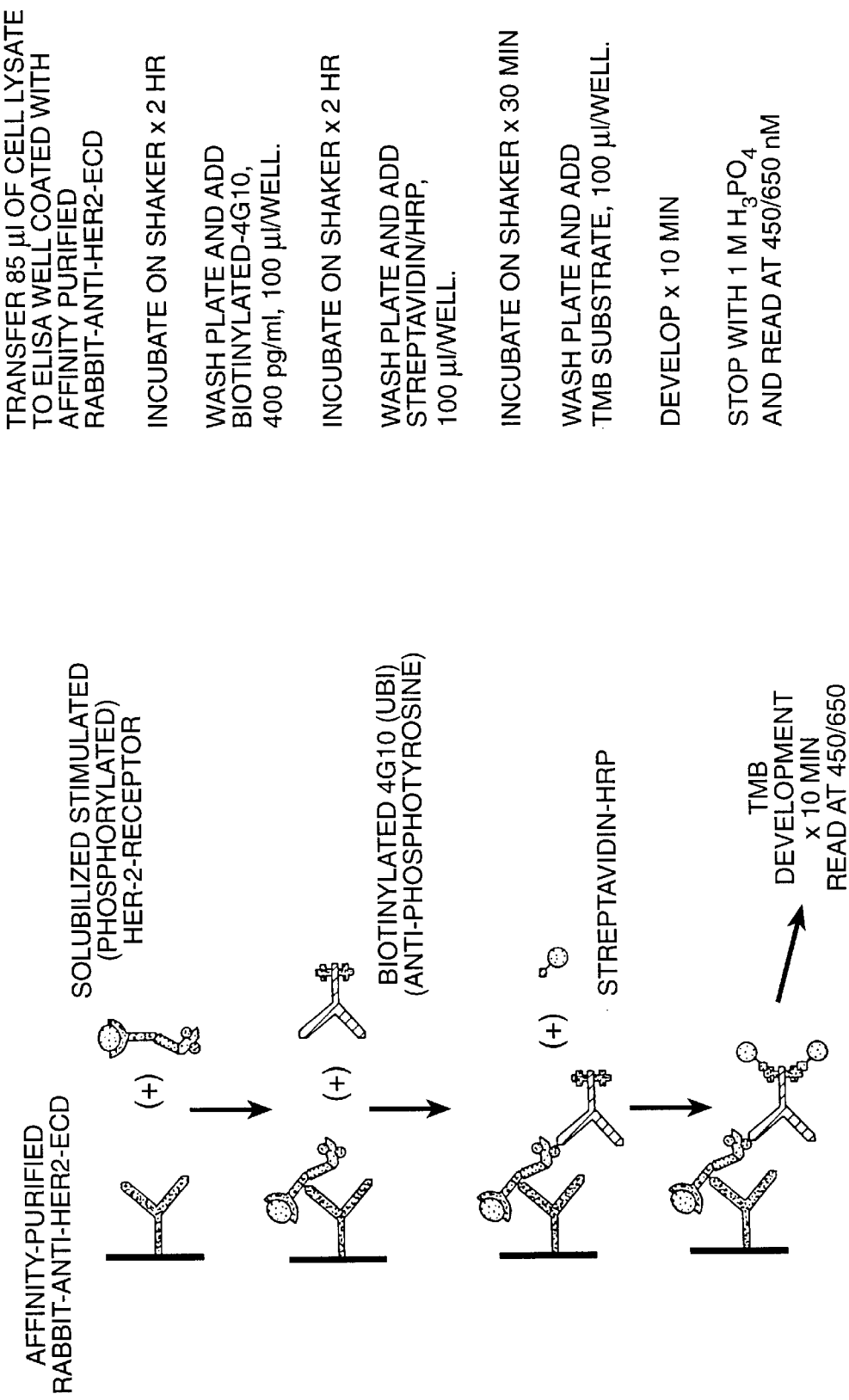
FIG._6B

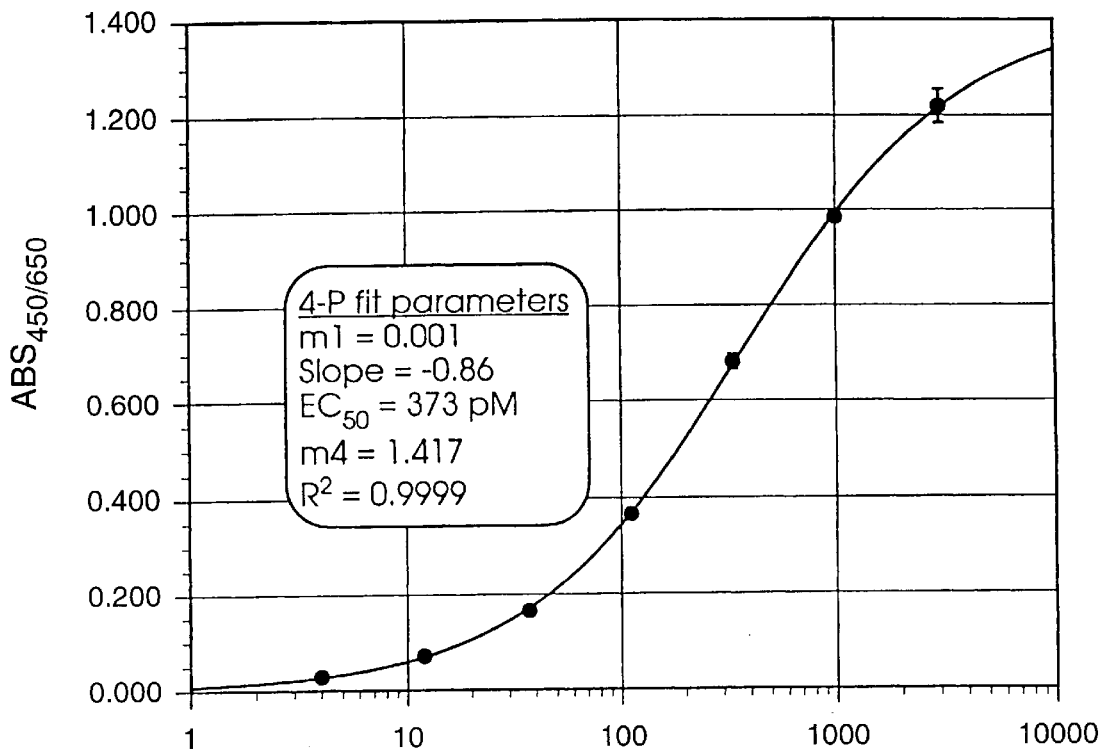
FIG._7
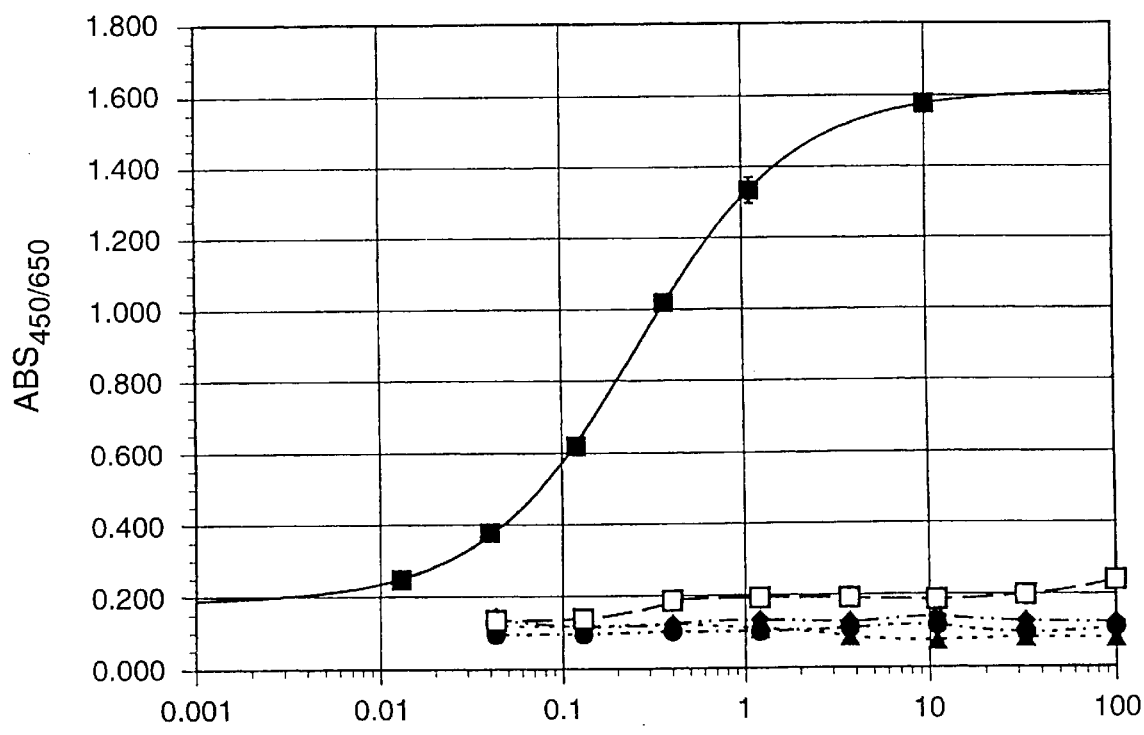
FIG._8

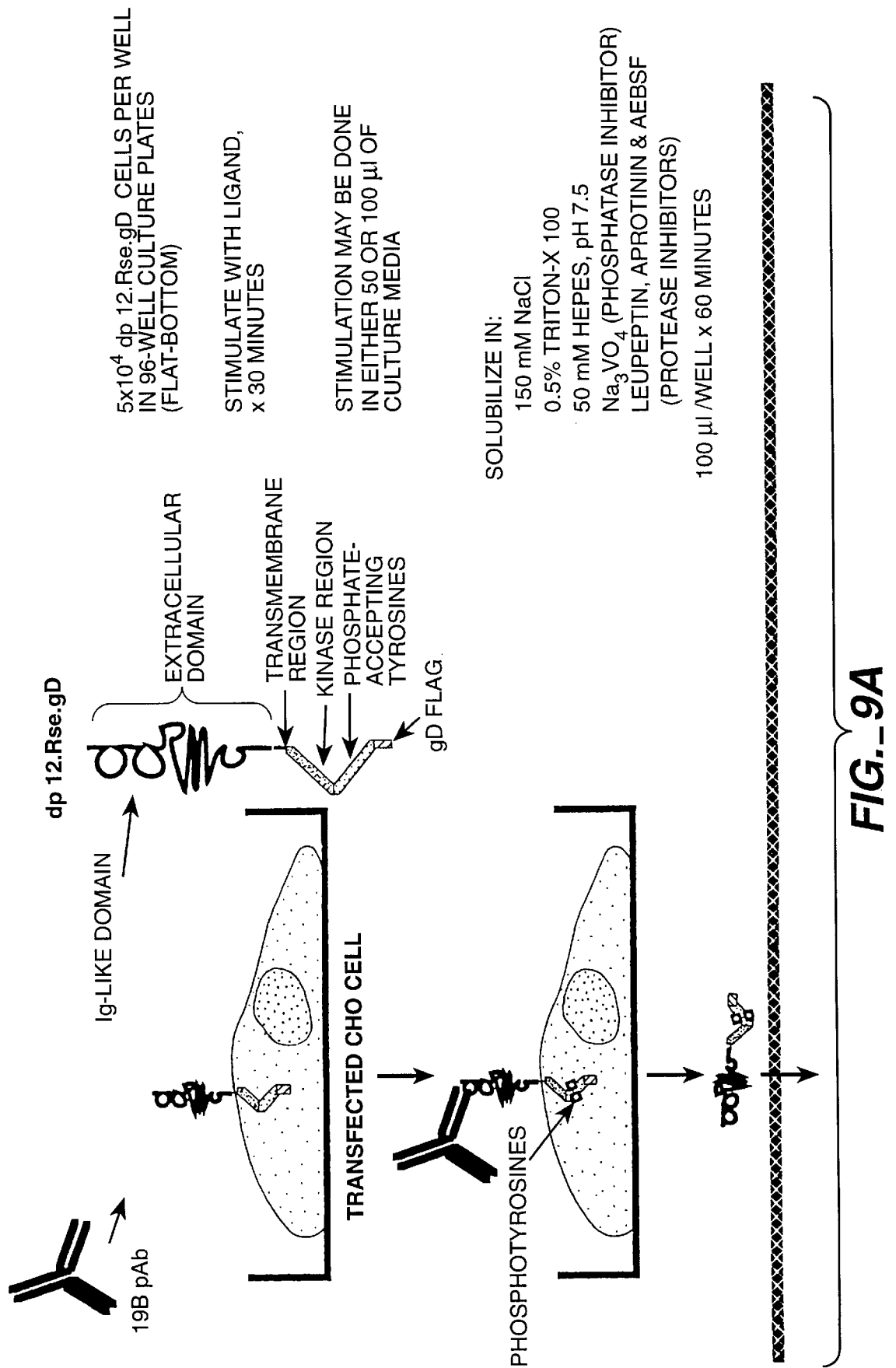
FIG._9A

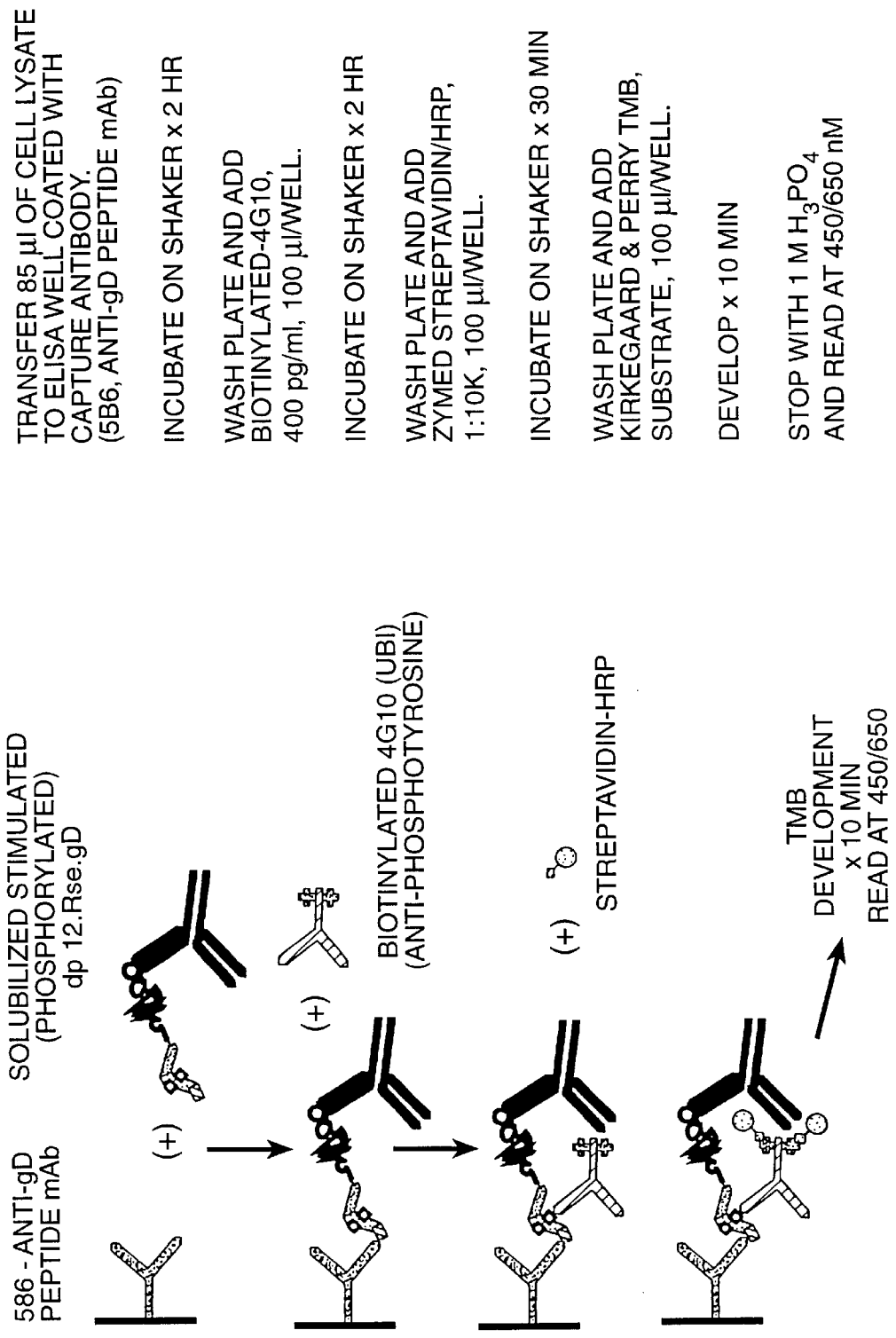
FIG._9B

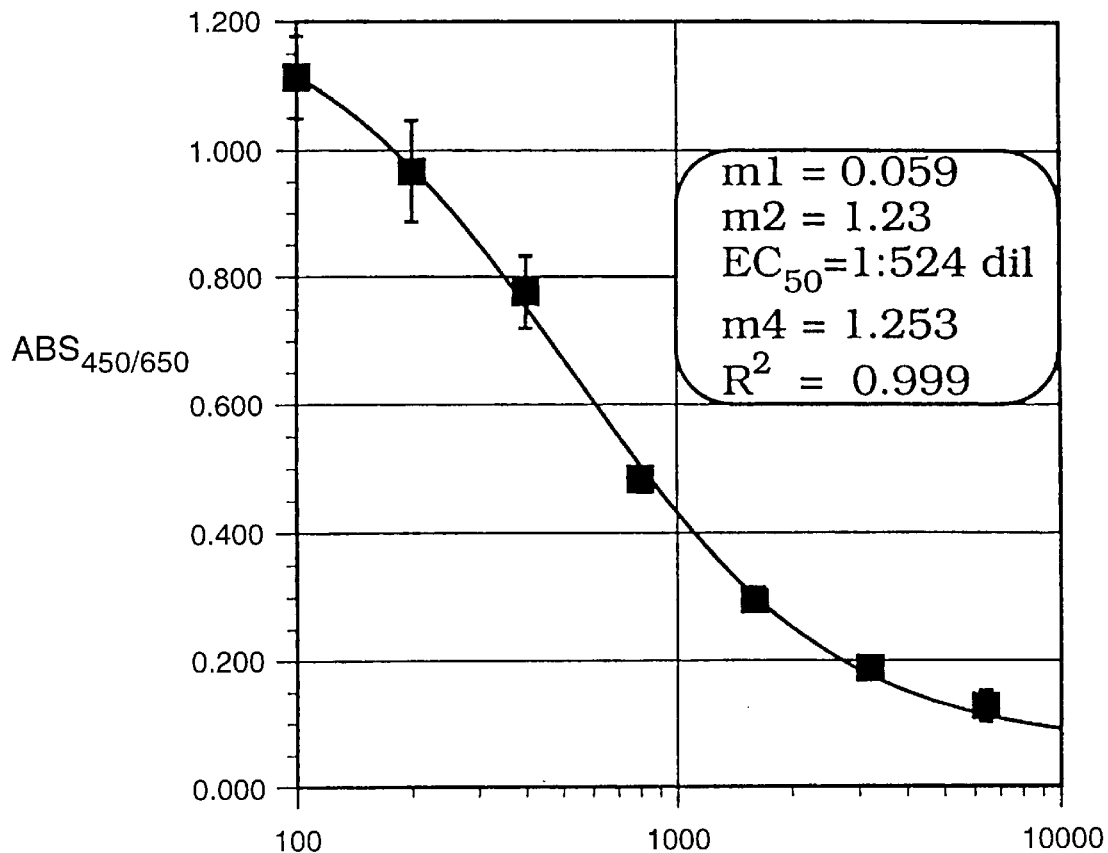
FIG._10
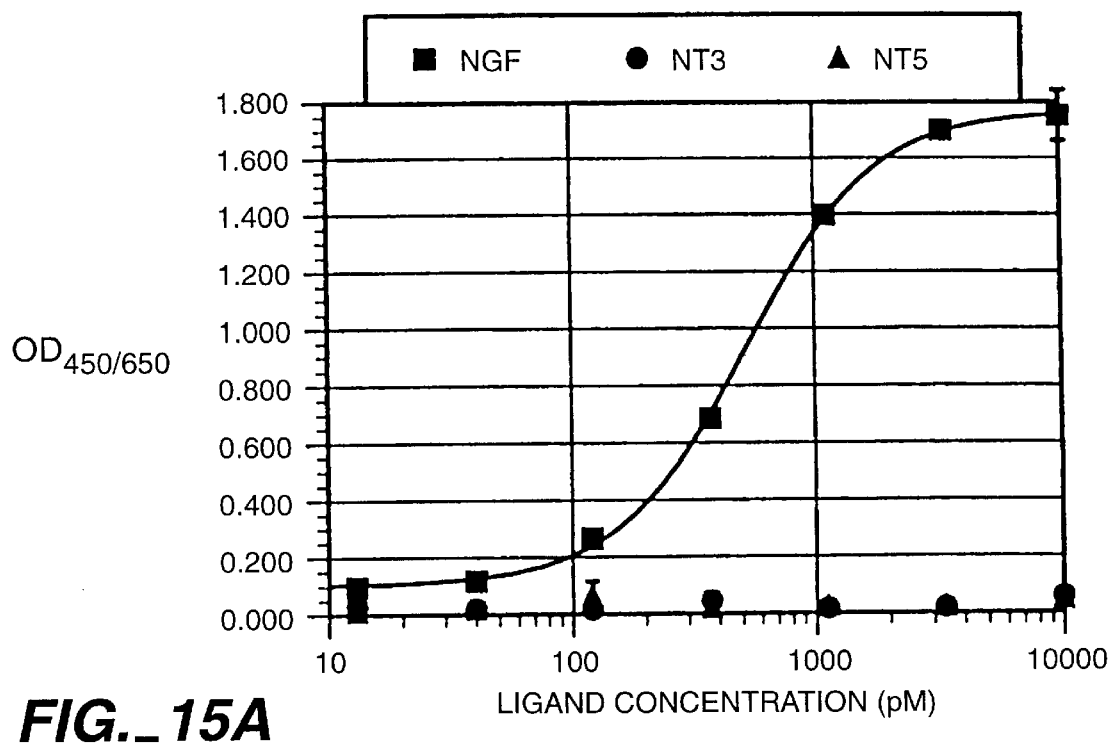
FIG._15A

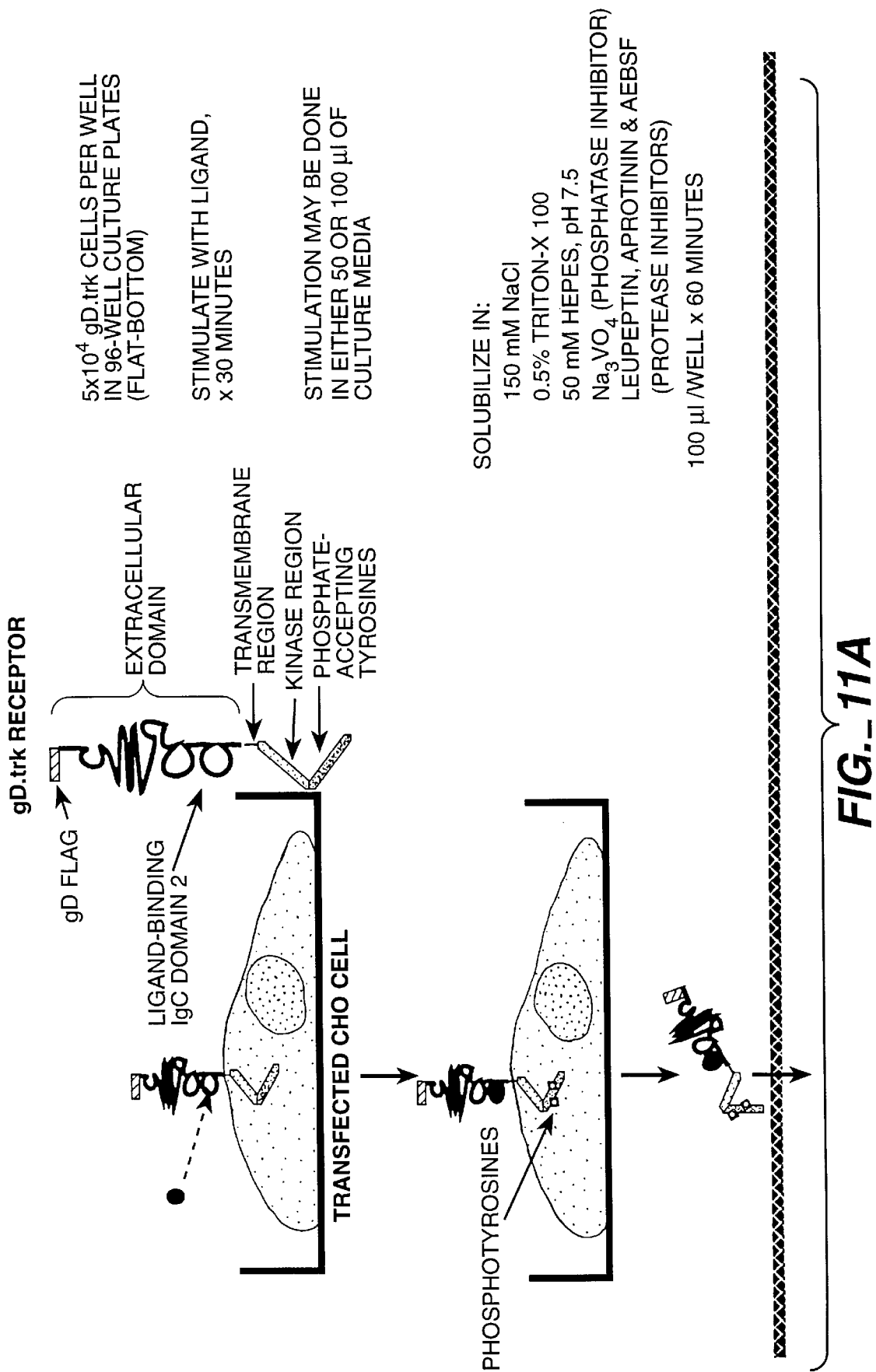
FIG._11A

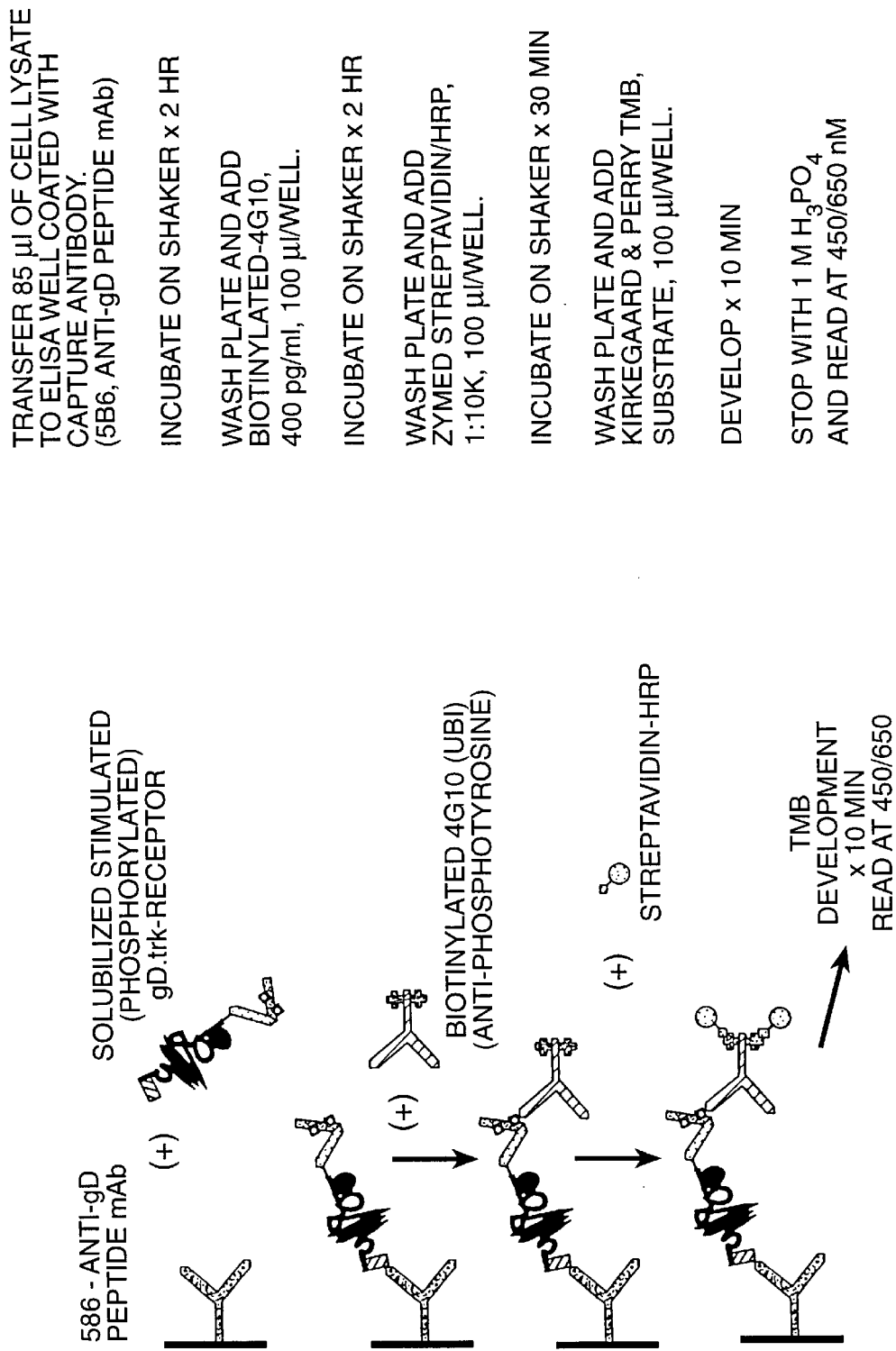
FIG._11B

```
                                ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker
           ^R1 site mutated in
           ^begin gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGCGAGG ACTGGGGACC CTGTGACAAG CTTCAGCGCG AACGACCAAC
      AGAGCAGTTA GAGGCGCTCC TGACCCCTGG GACACTGTTC GAAGTCGCGC TTGCTGGTTG ^Start gD
                                                      M*  G*  G*
1081  TACCCCGATC ATCAGTTATC CTTAAGGTCT CTTTTGTGTG GTGCGTTCCG GTATGGGGGG
      ATGGGGCTAG TAGTCAATAG GAATTCCAGA GAAAACACAC CACGCAAGGC CATACCCCCC 1   T*  A*  A*  R*  L*  G*  A*  V*  I*  L*  F*  V*  V*  I*  V*  G*  L*  H*  G*  V*
1141  GACTGCCGCC AGGTTGGGGG CCGTGATTTT GTTTGTCGTC CAAACAGCAG ATAGTGGGCC TCCATGGGGT
      CTGACGGCGG TCCAACCCCC GGCACTAAAA CAAACAGCAG TATCACCCGG AGGTACCCCA 24   R*  G*  K*  Y*  A*  L*  A    D    A    S    L    K    M    A    D    P    N    R    F    R
1201  CCGGCGGCAAA TATGCCTTGG CGGATGCCTC TCTCAAGATG GCCGACCCCA ATCGATTTCG
      GGCGCCGTTT ATACGGAACC GCCTACGGAG AGAGTTCTAC CGGCTGGGGT TAGCTAAAGC
```

*FIG._12A*

^Xho and GTA mutated in
^begin mature trkA

```
          G  K  D     L  P  V  L     D  Q  L     L  E  V     A  A  P  C     P  D  A
  44
1261    CGGCAAAGAC CTTCCGGTCC TGGACCAGCT GCTCGAGGTA GCCGCACCCT GCCCCGATGC
        GCCGTTTCTG GAAGGCCAGG ACCTGGTCGA CGAGCTCCAT CGGCGTGGGA CGGGGCTACG

C  C  P     H  G  S  S     G  L  R     C  T  R     D  G  A  L     D  S  L
  64
1321    CTGCTGCCCC CACGGCTCCT CGGGACTGCG ATGCACCCGG GATGGGGCCC TGGATAGCCT
        GACGACGGGG GTGCCGAGGA GCCCTGACGC TACGTGGGCC CTACCCCGGG ACCTATCGGA

H  H  L     P  G  A  E     N  L  T     E  L  Y     I  E  N  Q     Q  H  L
  84
1381    CCACCACCTG CCCGGCGCAG AGAACCTGAC TGAGCTCTAC ATCGAGAACC AGCAGCATCT
        GGTGGTGGAC GGGCCGCGTC TCTTGGACTG ACTCGAGATG TAGCTCTTGG TCGTCGTAGA

Q  Q  H  L     E  L  R  D     L  R  G     L  G  E     L  R  N  L     T  I  V
 104
1441    GCAGCATCTG GAGCTCCGTG ATCTGAGGGG CCTGGGGGAG CTGAGAAACC TCACCATCGT
        CGTCGTAGAC CTCGAGGCAC TAGACTCCCC GGACCCCCTC GACTCTTTGG AGTGGTAGCA

K  S  G     L  R  F  V     A  P  D     A  F  H     F  T  P  R     L  S  R
 124
1501    GAAGAGTGGT CTCCGTTTCG TGGCGCCAGA TGCCTTTCCAT TTCACTCCCTC GGCTCAGTCG
        CTTCTCACCA GAGGCAAAGC ACCGCGGTCT ACGGAAGGTA AAGTGAGGAG CCGAGTCAGC

L  N  L     S  F  N  A     L  E  S     L  S  W     K  T  V  Q     G  L  S
 144
1561    CCTGAATCTC TCCTTCAACG CTCTGGAGTC CTCTCCCTGG AAAACTGTGC AGGGCCTCTC
        GGACTTAGAG AGGAAGTTGC GAGACCTCAG GAGAGGGACC TTTTGACACG TCCCGGAGAG

L  Q  E     L  V  L  S     G  N  P     L  H  C     S  C  A  L     R  W  L
 164
1621    CTTACAGGAA CTGGTCCTGT CGGGGAACCC TCTGCACTGT TCTTGTGCCC TGCGCTGGCT
        GAATGTCCTT GACCAGGACA GCCCCTTGGG AGACGTGACA AGAACACGGG ACGCGACCGA
```

FIG._12B

| pos | | | | | | | | | | |
|---|---|---|---|---|---|---|---|---|---|---|
| 184 | Q | R | W | E | E | G | L | G | G | V | P | E | Q | K | L | Q | C | H | G |
| 1681 | ACAGCGCTGG | GAGGAGGAGG | GACTGGGCGG | AGTGCCTGAA | CAGAAGCTGC | AGTGTCATGG |
| | TGTCGCGACC | CTCCTCCTCC | CTGACCCGCC | TCACGGACTT | GTCTTCGACG | TCACAGTACC |
| 204 | Q | G | P | L | A | H | M | P | N | A | S | C | G | V | P | T | L | K | V | Q |
| 1741 | GCAAGGGCCC | CTGGCCCACA | TGCCCAATGC | CAGCTGTGGT | GTGCCCACGC | TGAAGGTCCA |
| | CGTTCCCGGG | GACCGGGTGT | ACGGGTTACG | GTCGACACCA | CACGGGTGCG | ACTTCCAGGT |
| 224 | V | P | N | A | S | V | D | D | V | L | L | R | C | Q | V | E | G |
| 1801 | GGTGCCCAAT | GCCTCGGTGG | ATGTGGGGGA | CGACGTGCTG | CTGCGGTGCC | AGGTGGAGGG |
| | CCACGGGTTA | CGGAGCCACC | TACACCCCCT | GCTGCACGAC | GACGCCACGG | TCCACCTCCC |
| 244 | R | G | L | E | Q | A | G | W | I | L | T | E | L | E | Q | S | A | T | V | M |
| 1861 | GCGGGGCCTG | GAGCAGGCCG | GCTGGATCCT | CACAGAGCTG | GAGCAGTCAG | CCACGGTGAT |
| | CGCCCCGGAC | CTCGTCCGGC | CGACCTAGGA | GTGTCTCGAC | CTCGTCAGTC | GGTGCCACTA |
| 264 | K | S | G | G | L | P | S | L | G | L | T | L | A | N | V | T | S | D | L | N |
| 1921 | GAAATCTGGG | GGTCTGCCAT | CCCTGGGGCT | GACCCTGGCC | AATGTCACCA | GTGACCTCAA |
| | CTTTAGACCC | CCAGACGGTA | GGGACCCCGA | CTGGGACCGG | TTACAGTGGT | CACTGGAGTT |
| 284 | R | K | N | L | T | C | W | A | E | N | D | V | G | R | A | E | V | S | V | Q |
| 1981 | CAGGAAGAAC | TTGACGTGCT | GGGCAGAGAA | CGATGTGGGC | CGGGCAGAGG | TCTCTGTTCA |
| | GTCCTTCTTG | AACTGCACGA | CCCGTCTCTT | GCTACACCCG | GCCCGTCTCC | AGAGACAAGT |
| 304 | V | N | V | S | F | P | A | L | H | T | A | V | E | M | H | H | W |
| 2041 | GGTCAACGTC | TCCTTCCCGG | CCAGTGTGCA | GCTGCACACG | GCGGTGGAGA | TGCACCACTG |
| | CCAGTTGCAG | AGGAAGGGCC | GGTCACACGT | CGACGTGTGC | CGCCACCTCT | ACGTGGTGAC |

```
184  Q   R   W   E   E   E   G   L   G   G   V   P   E   Q   K   L   Q   C   H   G
1681 ACAGCGCTGG GAGGAGGAGG GACTGGGCGG AGTGCCTGAA CAGAAGCTGC AGTGTCATGG
     TGTCGCGACC CTCCTCCTCC CTGACCCGCC TCACGGACTT GTCTTCGACG TCACAGTACC

204  Q   G   P   L   A   H   M   P   N   A   S   C   G   V   P   T   L   K   V   Q
1741 GCAAGGGCCC CTGGCCCACA TGCCCAATGC CAGCTGTGGT GTGCCCACGC TGAAGGTCCA
     CGTTCCCGGG GACCGGGTGT ACGGGTTACG GTCGACACCA CACGGGTGCG ACTTCCAGGT

224  V   P   N   A   S   V   D   V   G   D   D   V   L   L   R   C   Q   V   E   G
1801 GGTGCCCAAT GCCTCGGTGG ATGTGGGGGA CGACGTGCTG CTGCGGTGCC AGGTGGAGGG
     CCACGGGTTA CGGAGCCACC TACACCCCCT GCTGCACGAC GACGCCACGG TCCACCTCCC

244  R   G   L   E   Q   A   G   W   I   L   T   E   L   E   Q   S   A   T   V   M
1861 GCGGGGGCTG GAGCAGGCCG GCTGGATCCT CACAGAGCTG GAGCAGTCAG CCACGGTGAT
     CGCCCCCGAC CTCGTCCGGC CGACCTAGGA GTGTCTCGAC CTCGTCAGTC GGTGCCACTA

264  K   S   G   G   L   P   S   L   G   L   A   E   N   D   V   G   R   A   E   V
1921 GAAATCTGGG GGTCTGCCAT CCCTGGGGCT GGCAGAGAAC GATGTGGGGC GGGCAGAGGT
     CTTTAGACCC CCAGACGGTA GGGACCCCGA CCGTCTCTTG CTACACCCCG GCCCGTCTCC

284  R   K   N   L   T   C   W   A   E   N   D   V   G   L   H   T   A   V   E   M
1981 CAGGAAGAAC TTGACGTGCT GGGCAGAGAA CGATGTGGGC CGGGCAGAGG TCTCTGTTCA
     GTCCTTCTTG AACTGCACGA CCCGTCTCTT GCTACACCCG GCCCGTCTCC AGAGACAAGT

304  V   N   V   S   F   P   A   S   V   Q   L   H   T   A   V   E   M   H   H   W
2041 GGTCAACGTC TCCTTCCCGG CCAGTGTGCA GCTGCACACG GCGGTGGAGA TGCACCACTG
     CCAGTTGCAG AGGAAGGGCC GGTCACACGT CGACGTGTGC CGCCACCTCT ACGTGGTGAC
```

```
464  N K F      G I N R      P A V      L A P      E D G L      A M S
2521 AAACAAGTTT GGGATCAACC GCCCGGCTGT GCTGGCTCCA GAGGATGGGC TGGCCATGTC
     TTTGTTCAAA CCCTAGTTGG CGGGCCGACA CGACCGAGGT CTCCTACCCG ACCGGTACAG

484  L H F      M T L G      G S S      L S P      T E G K      G S G
2581 CCTGCATTTC ATGACATTGG GTGGCAGCTC CCTGTCCCCC ACCGAGGGCA AAGGCTCTGG
     GGACGTAAAG TACTGTAACC CACCGTCGAG GGACAGGGGG TGGCTCCCGT TTCCGAGACC

504  L Q G      H I I E      N P Q      Y F S      D A C V      H H I
2641 GCTCCAAGGC CACATCATCG AGAACCCACA ATACTTCAGT GATGCCTGTG TTCACCACAT
     CGAGGTTCCG GTGTAGTAGC TCTTGGGTGT TATGAAGTCA CTACGGACAC AAGTGGTGTA

524  K R R      D I V L      K W E      L G E      G A F G      K V F
2701 CAAGCGCCGG GACATCGTGC TCAAGTGGGA GCTGGGGGAG GGCGCCTTTG GGAAGGTCTT
     GTTCGCGGCC CTGTAGCACG AGTTCACCCT CGACCCCCTC CCGCGGAAAC CCTTCCAGAA

544  L A E      C H N L      Q D K      L P E      R E A E      V K A
2761 CCTTGCTGAG TGCCACAACC TCCAGGACAA GCTGCCTGAG CGTGAGGCTG AGGTCAAGGC
     GGAACGACTC ACGGTGTTGG AGGTCCTGTT CGACGGACTC GCACTCCGAC TCCAGTTCCG

564  L K E      A S E S      A R Q      D F Q      R E A E      L L T
2821 ACTGAAGGAG GCGTCCGAGA GTGCTCGGCA GGACTTCCAA CGTGAGGCTG AGCTGCTCAC
     TGACTTCCTC CGCAGGCTCT CACGAGCCGT CCTGAAGGTT GCACTCCGAC TCGACGAGTG

584  M L Q      H Q H I      V R F      F G V      C T E G      R P L
2881 CATGCTGCAG CACCAGCACA TCGTGCGCTT CTTCGGCGTC TGCACCGAGG GCCGCCCCCT
     GTACGACGTC GTGGTCGTGT AGCACGCGAA GAAGCCGCAG ACGTGGCTCC CGGCGGGGGA
```

FIG._12E

```
604  L  M  V   F  E  Y   M  R  H   G  D  L   N  R  F   L  R  S   H  G
2941 GCTCATGGTC TTTGAGTATA TGCGGCACGG GGACCTCAAC CGCTTCCTCC GATCCCATGG
     CGAGTACCAG AAACTCATAT ACGCCGTGCC CCTGGAGTTG GCGAAGGAGG CTAGGGTACC

624  P  D  A   K  L  L   A  G  G   E  D  V   A  P  G   P  L  G   L  G
3001 ACCTGATGCC AAGCTGCTGG CTGGTGGGGA GGATGTGGCT CCAGGCCCCC TGGGTCTGGG
     TGGACTACGG TTCGACGACC GACCACCCCT CCTACACCGA GGTCCGGGGG ACCCAGACCC

644  Q  L  L   A  V  A   S  Q  V   A  A  G   M  V  Y   L  A  G   L  H
3061 GCAGCTGCTG GCCGTGGCTA GCCAGGTCGC TGCGGGGATG GTGTACCTGG CGGGTCTGCA
     CGTCGACGAC CGGCACCGAT CGGTCCAGCG ACGCCCCTAC CACATGGACC GCCCAGACGT

664  F  V  H   R  D  L   A  T  R   N  C  L   V  G  Q   G  L  V   V  K
3121 TTTTGTGCAC CGGGACCTGG CCACACGCAA CTGTCTAGTG GGCCAGGGAC TGGTGGTCAA
     AAAACACGTG GCCCTGGACC GGTGTGCGTT GACAGATCAC CCGGTCCCTG ACCACCAGTT

684  I  G  D   F  G  M   S  R  D   I  Y  S   T  D  Y   Y  R  V   G  G
3181 GATTGGTGAT TTTGGCATGA GCAGGGATAT CTACAGCACC GACTATTACC GTGTGGGAGG
     CTAACCACTA AAACCGTACT CGTCCCTATA GATGTCGTGG CTGATAATGG CACACCCTCC

704  R  T  M   L  P  I   R  W  M   P  P  E   S  I  L   Y  R  K   F  T
3241 CCGCACCATG CTGCCCATTC GCTGGATGCC GCCCGAGAGC ATCCTGTACC GTAAGTTCAC
     GGCGTGGTAC GACGGGTAAG CGACCTACGG CGGGCTCTCG TAGGACATGG CATTCAAGTG

724  T  E  S   D  V  W   S  F  G   V  V  L   W  E  I   F  T  Y   G  K
3301 CACCGAGAGC GACGTGTGGA GCTTCGGCGT GGTGCTCTGG GAGATCTTCA CCTACGGCAA
     GTGGCTCTCG CTGCACACCT CGAAGCCGCA CCACGAGACC CTCTAGAAGT GGATGCCGTT

```
3361  GCAGCCCTGG TACCAGCTCT CCAACACGGA GGCAATCGAC TGCATCACGC AGGGACGTGA
      CGTCGGGACC ATGGTCGAGA GGTTGTGCCT CCGTTAGCTG ACGTAGTGCG TCCCTGCACT

764    L   E   R   P   R   A   C   P   P   E   V   Y   A   I   M   R   G   C   W   Q
3421  GTTGGAGCGG CCACGTGCCT GCCCACCAGA GGTCTACGCC ATCATGCGGG GCTGCTGGCA
      CAACCTCGCC GGTGCACGGA CGGGTGGTCT CCAGATGCGG TAGTACGCCC CGACGACCGT

784    R   E   P   Q   Q   R   H   S   I   K   D   V   H   A   R   L   Q   A   L   A
3481  GCGGGAGCCC CAGCAACGCC ACAGCATCAA GGATGTGCAC GCCCGGCTGC AAGCCCTGGC
      CGCCCTCGGG GTCGTTGCGG TGTCGTAGTT CCTACACGTG CGGGCCGACG TTCGGGACCG

R1 site added with cloning primer^
                R1 site removed with cut and fill^

804    Q   A   P   P   V   Y   L   D   V   L   G   Q
3541  CCAGGCACCT CCTGTCTACC TGGATGTCCT GGGCTAGAAT TAATTCAATC GATGGCCGCC
      GGTCCGTGGA GGACAGATGG ACCTACAGGA CCCGATCTTA ATTAAGTTAG CTACCGGCGG

^sv40 early poly A
3601  ATGGCCCAAC TTGTTTATTG CAGCTTATAA TGGTTACAAA TAAAGCAATA GCATCACAAA
      TACCGGGTTG AACAAATAAC GTCGAATATT ACCAATGTTT ATTTCGTTAT CGTAGTGTTT
```

*FIG._12G*

```
                ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker    ^begin gD from pchadII
 901  ACCTCGGTTC TATCGATTGA ATTCCACTGC CTTCCACCAA GCTCTGCAGG ATCCCAGAGT
      TGGAGCCAAG ATAGCTAACT TAAGGTGACG GAAGGTGGTT CGAGACGTCC TAGGGTCTCA 961  CAGGGGTCTG TATCTTCCTG CTGGTGGCTC CAGTTCAGGA ACAGTAAACC CTGCTCCGAA
      GTCCCCAGAC ATAGAAGGAC GACCACCGAG GTCAAGTCCT TGTCATTTGG GACGAGGCTT 1021  TATTGCCTCT CACATCTCGT CAATCTCCGC GAGGACTGGG GACCCTGTGA CAAGCTTCAG
      ATAACGGAGA GTGTAGAGCA GTTAGAGGCG CTCCTGACCC CTGGGACACT GTTCGAAGTC 1081  CGCGAACGAC CAACTACCCC GATCATCAGT TATCCTTAAG GTCTCTTTTG TGTGGTGCGT
      GCGCTTGCTG GTTGATGGGG CTAGTAGTCA ATAGGAATTC CAGAGAAAAC ACACCACGCA ^Start gD
  1       M* G* G* T* A*   A* R* L*    G* A* V* I*   L* F* V*   V* I* V*
1141  TCCGGTATGG GGGGACTGGC GCCCAGGTTG GGGGCCGTGA TTTTGTTTGT CGTCATAGTG
      AGGCCATACC CCCCTGACCG CGGGTCCAAC CCCCGGCACT AAAACAAACA GCAGTATCAC 19   G* L* H* G*   V* R* G*   K* Y* A*   L* A D A   S L K M A D
1201  GGCCTCCATG GGGTCCGCGG CAAATATGCC TTGGCGGATG CCTCTCTCAA GATGGCCGAC
      CCGGAGGTAC CCCAGGCGCC GTTTATACGG AACCGCCTAC GGAGAGAGTT CTACCGGCTG
```

*FIG._13A*

```
                                          xho and GTA mutated in^
                                                              start mature trkB^
 39  P   N   R   F   R   G   K   D   L   P   V   L   D   Q   L   L   E   V   C   P
1261 CCCAATCGAT TTCGCGGCAA AGACCTTCCG GTCCTGGACC AGCTGCTCGA GGTATGTCCC
     GGGTTAGCTA AAGCGCCGTT TCTGGAAGGC CAGGACCTGG TCGACGAGCT CCATACAGGG 59  T   S   C   K   C   S   A   S   R   I   W   C   S   D   P   S   P   G   I   V
1321 ACGTCCTGCA AATGCAGTGC CTCTCGGATC TGGTGCAGCG ACCCTTCTCC TGGCATCGTG
     TGCAGGACGT TTACGTCACG GAGAGCCTAG ACCACGTCGC TGGGAAGAGG ACCGTAGCAC 79  A   F   P   R   L   E   P   N   S   V   D   P   E   N   I   T   E   I   F   I
1381 GCATTTCCGA GATTGGAGCC TAACAGTGTA GATCCTGAGA ACATCACCGA AATTTTCATC
     CGTAAAGGCT CTAACCTCGG ATTGTCACAT CTAGGACTCT TGTAGTGGCT TTAAAAGTAG 99  A   N   Q   K   R   L   E   I   I   N   E   D   D   V   E   A   Y   V   G   L
1441 GCAAACCAGA AAAGGTTAGA AATCATCAAC GAAGATGATG TTGAAGCTTA TGTGGGACTG
     CGTTTGGTCT TTTCCAATCT TTAGTAGTTG CTTCTACTAC AACTTCGAAT ACACCCTGAC 119  R   N   L   T   I   V   D   S   G   L   K   F   V   A   H   K   A   F   L   K
1501 AGAAATCTGA CAATTGTGGA TTCTGGATTA AAATTTGTGG CTCATAAAGC ATTTCTGAAA
     TCTTTAGACT GTTAACACCT AAGACCTAAT TTTAAACACC GAGTATTTCG TAAAGACTTT 139  N   S   N   L   Q   H   I   N   F   T   R   N   K   L   T   S   L   S   R   K
1561 AACAGCAACC TGCAGCACAT CAATTTTACC CGAAACAAAC TGACGAGTTT GTCTAGGAAA
     TTGTCGTTGG ACGTCGTGTA GTTAAAATGG GCTTTGTTTG ACTGCTCAAA CAGATCCTTT 159  H   F   R   H   L   D   L   S   E   L   I   L   V   G   N   P   F   T   C   S
1621 CATTTCCGTC ACCTTGACTT GTCTGAACTG ATCCTGGTGG GCAATCCATT TACATGCTCC
     GTAAAGGCAG TGGAACTGAA CAGACTTGAC TAGGACCACC CGTTAGGTAA ATGTACGAGG
```

*FIG._13B*

```
179  C   D   I   M   W   I   K   T   L   Q   E   A   K   S   S   P   D   T   Q   D
1681 TGTGACATTA TGTGGATCAA CACCTAGTT GACTCTCCAA GAGGCTAAAT CCAGTCCAGA CACTCAGGAT
     ACACTGTAAT ACACCTAGTT CTGAGAGGTT CTCCGATTTA GGTCAGGTCT GTGAGTCCTA

199  L   Y   C   L   N   E   S   S   K   N   I   P   L   A   N   L   Q   I   P   N
1741 TTGTACTGCC TGAATGAAAG CAGCAAGAAT ATTCCCCTGG CAAACCTGCA GATACCCAAT
     AACATGACGG ACTTACTTTC GTCGTTCTTA TAAGGGGACC GTTTGGACGT CTATGGGTTA

219  C   G   L   P   S   A   N   L   A   A   P   N   L   T   V   E   E   G   K   S
1801 TGTGGTTTGC CATCTGCAAA TCTGGCCGCA CCTAACCTCA CTGTGGAGGA AGGAAAGTCT
     ACACCAAACG GTAGACGTTT AGACCGGCGT GGATTGGAGT GACACCTCCT TCCTTTCAGA

239  I   T   L   S   C   S   V   A   G   D   P   V   P   N   M   Y   W   D   V   G
1861 ATCACATTAT CCTGTAGTGT GGCAGGTGAT CCGGTTCCTA ATATGTATTG GGATGTTGGT
     TAGTGTAATA GGACATCACA CCGTCCACTA GGCCAAGGAT TATACATAAC CCTACAACCA

259  N   L   V   S   K   H   M   N   E   T   S   H   T   Q   G   S   L   R   I   T
1921 AACCTGGTTT CCAAACATAT GAATGAAACA AGCCACACAC AGGGCTCCTT AAGGATAACT
     TTGGACCAAA GGTTTGTATA CTTACTTTGT TCGGTGTGTG TCCCGAGGAA TTCCTATTGA

279  N   I   S   S   D   D   S   G   K   Q   I   S   C   V   A   E   N   L   V   G
1981 AACATTTCAT CCGATGACAG TGGGAAGCAG ATCTCTTGTG TGGCGGAAAA TCTTGTAGGA
     TTGTAAAGTA GGCTACTGTC ACCCTTCGTC TAGAGAACAC ACCGCCTTTT AGAACATCCT

299  E   D   Q   S   V   N   L   T   V   H   F   A   P   T   I   T   F   L   E
2041 GAAGATCAAG ATTCTGTCAA CCTCACTGTG CATTTTGCAC CAACTATCAC ATTCTCTGAA
     CTTCTAGTTC TAAGACAGTT GGAGTGACAC GTAAAACGTG GTTGATAGTG TAAAGAGCTT
```

FIG.—13C

```
319  S   P   T   S   D   H   H   W   C   I   P   F   T   V   K   G   N   P   K   P
2101 TCTCCAACCT CAGACCACCA CTGGTGCATT CCATTCACTG TGAAAGGCAA CCCAAAACCA
     AGAGGTTGGA GTCTGGTGGT GACCACGTAA GGTAAGTGAC ACTTTCCGTT GGGTTTTGGT

339  A   L   Q   W   F   Y   N   G   A   I   L   N   E   S   K   Y   I   C   T   K
2161 GCGCTTCAGT GGTTCTATAA CGGGGCAATA TTGAATGAGT CCAAATACAT CTGTACTAAA
     CGCGAAGTCA CCAAGATATT GCCCCGTTAT AACTTACTCA GGTTTATGTA GACATGATTT

359  I   H   V   T   N   H   T   E   Y   H   G   C   L   Q   L   D   N   P   T   H
2221 ATACATGTTA CCAATCACAC GGAGTACCAC GGCTGCCTCC AGCTGGATAA TCCCACTCAC
     TATGTACAAT GGTTAGTGTG CCTCATGGTG CCGACGGAGG TCGACCTATT AGGGTGAGTG

379  M   N   N   G   D   Y   T   L   I   A   K   N   E   Y   G   K   D   E   K   Q
2281 ATGAACAATG GGGACTACAC TCTAATAGCC AAGAATGAGT ATGGGAAGGA TGAGAAACAG
     TACTTGTTAC CCCTGATGTG AGATTATCGG TTCTTACTCA TACCCTTCCT ACTCTTTGTC

399  I   S   A   H   F   M   G   W   P   G   I   D   D   G   A   N   P   N   Y   P
2341 ATTTCTGCTC ACTTCATGGG CTGGCCTGGA ATTGACGATG GTGCAAACCC AAATTATCCT
     TAAAGACGAG TGAAGTACCC GACCGGACCT TAACTGCTAC CACGTTTGGG TTTAATAGGA

419  D   V   I   Y   E   D   Y   G   T   A   A   N   D   I   G   D   T   N   R
2401 GATGTAATTT ATGAAGATTA TGGAACTGCA GCGAATGACA TCGGGGACAC CACGAACAGA
     CTACATTAAA TACTTCTAAT ACCTTGACGT CGCTTACTGT AGCCCCTGTG GTGCTTGTCT

439  S   N   E   I   P   S   T   D   V   T   D   K   T   G   R   E   H   L   S   V
2461 AGTAATGAAA TCCCCTTCCAC AGACGTCACT GATAAAACCG GTCGGGAACA TCTCTCGGTC
     TCATTACTTT AGGGAAGGTG TCTGCAGTGA CTATTTTGGC CAGCCCTTGT AGAGAGCCAG

459  Y   A   V   V   I   A   S   V   V   G   F   C   L   L   V   M   L   F   L
2521 TATGCTGTGG TGGTGATTGC GTCTGTGGTG GGATTTTGCC TTTTGGTAAT GCTGTTTCTG
     ATACGACACC ACCACTAACG CAGACACCAC CCTAAAACGG AAAACCATTA CGACAAAGAC
```

FIG.-13D

```
479  L  K  L  A  R  H  S  K  F  G  M  K  G  P  A  S  V  I  S  N
2581 CTTAAGTTGG CAAGACACTC CAAGTTCAAA KFG ATGAAAGGCC CAGCCTCCGT TATCAGCAAT
     GAATTCAACC GTTCTGTGAG GTTCAAACCG TACTTTCCGG GTCGGAGGCA ATAGTCGTTA

499  D  D  D  S  A  S  P  L  H  H  I  S  N  G  S  N  T  P  S  S
2641 GATGATGACT CTGCCAGCCC ACTCCATCAC ATCTCCAATG GGAGTAACAC TCCATCTTCT
     CTACTACTGA GACGGTCGGG TGAGGTAGTG TAGAGGTTAC CCTCATTGTG AGGTAGAAGA

519  S  E  G  G  P  D  A  V  I  I  G  M  T  K  I  P  V  I  E  N
2701 TCGGAAGGTG GCCCAGATGC TGTCATTATT GGAATGACCA AGATCCCTGT CATTGAAAAT
     AGCCTTCCAC CGGGTCTACG ACAGTAATAA CCTTACTGGT TCTAGGGACA GTAACTTTTA

539  P  Q  Y  F  G  I  T  N  S  Q  L  K  P  D  T  F  V  Q  H  I
2761 CCCCAGTACT TTGGCATCAC CAACAGTCAG CTCAAGCCAG ACACATTTGT TCAGCACATC
     GGGGTCATGA AACCGTAGTG GTTGTCAGTC GAGTTCGGTC TGTGTAAACA AGTCGTGTAG

559  K  R  H  N  I  V  L  K  R  E  L  G  E  G  A  F  G  K  V  F
2821 AAGCGACATA ACATTGTTCT GAAAAGGGAG CTAGGCGAAG GAGCCTTTGG AAAAGTGTTC
     TTCGCTGTAT TGTAACAAGA CTTTTCCCTC GATCCGCTTC CTCGGAAACC TTTTCACAAG

579  L  A  E  C  Y  N  L  C  P  E  Q  D  K  I  L  V  A  V  K  T
2881 CTAGCTGAAT GCTATAACCT CTGTCCTGAG CAGGACAAGA TCCTGGTGGC AGTGAAGACC
     GATCGACTTA CGATATTGGA GACAGGACTC GTCCTGTTCT AGGACCACCG TCACTTCTGG

599  L  K  D  A  S  D  N  A  R  K  D  F  H  R  E  A  E  L  L  T
2941 CTGAAGGATG CCAGTGACAA TGCACGCAAG GACTTCCACC GTGAGGCCGA GCTCCTGACC
     GACTTCCTAC GGTCACTGTT ACGTGCGTTC CTGAAGGTGG CACTCCGGCT CGAGGACTGG
```

*FIG._13E*

```
619  N L Q H      E H I      V K F      Y G V C     V E G      D P L
3001 AACCTCCAGC ATGAGCACAT CGTCAAGTTC TATGGCGTCT GCGTGGAGGG CGACCCCCTC
     TTGGAGGTCG TACTCGTGTA GCAGTTCAAG ATACCGCAGA CGCACCTCCC GCTGGGGGAG

639  I M V F     E Y M      K H G      E G N      P P T E     L T Q      S Q M
3061 ATCATGGTCT TTGAGTACAT GAAGCATGGG GAGGGCAAC CGGCCCACGG AACTGACGCA GTCGCAGATG
     TAGTACCAGA AACTCATGTA CTTCGTACCC CTCCCGTTG GCCGGGTGCC TTGACTGCGT CAGCGTCTAC

659  P D A V    L M A       Q Q I       A A G       M V Y L     A S Q      H F V
3121 CCTGATGCCG TGCTGATGGC CCAGCAGAT CGCCGCGGGC ATGGTCTACC TGGCGTCCCA GCACTTCGTG
     GGACTACGGC ACGACTACCG GGTCGTCTA GCGGCGCCCG TACCAGATGG ACCGCAGGGT CGTGAAGCAC

679  L H I A     Q Q I      A T R       N C L       V G E N     L L V      K I G
3181 CTGCATATAG CCCAGCAGAT TGGCCACCAG GAACTGCCTG GTCGGGGAGA ACTTGCTGGT GAAAATCGGG
     GACGTATATC GGGTCGTCTA ACCGGTGGTC CTTGACGGAC CAGCCCCTCT TGAACGACCA CTTTTAGCCC

699  H R D L     A T R      S R D       V Y S       T D Y Y     R V G      G H T
3241 CACCGGGATT TGGCCACCAG TGTCCCGGGA CGTGTACAGC ACTGACTACT ACAGGGTCGG TGGCCACACA
     GTGGCCGCTAA ACCGGTGGTC ACAGGGCCCT GCACATGTCG TGACTGATGA TGTCCCAGCC ACCGGTGTGT

719  D F G M     S R D      R W M       P P E       S I M Y     R K F      T T E
3301 GACTTTGGGA TGTCCCGGGA CGTGTACAGC ACTGACTACT GCCTCCAGAG AGCATCATGT ACAGGAAATT CACGACGGAA
     CTGAAACCCT ACAGGGCCCT GCACATGTCG TGACTGATGA CGGAGGTCTC TCGTAGTACA TGTCCTTTAA GTGCTGCCTT

739  M L P I     R W M      P P E       V V L       W E I F     T Y G      K Q P
3361 ATGCTGCCCA TTCGCTGGAT GCCTCCAGAG GTCGTGTTG TGGGAGATTT TCACCTATGG CAAACAGCCC
     TACGACGGGT AAGCGACCTA CGGAGGTCTC CAGCACAAC ACCCTCTAAA AGTGGATACC GTTTGTCGGG

759  S D V W     S L G
3421 AGCGACGTCT GGAGCCTGGG
```

FIG._13F

```
              TCGCTGCAGA CCTCGGACCC CCAGCACAAC ACCCTCTAAA AGTGGATACC GTTTGTCGGG
779  W  Y  Q  L        S  N  N       E  V  I         E  C  I  T       Q  G  R       V  L  Q
3481 TGGTACCAGC TGTCAAACAA TGAGGTGATA GAGTGTATCA CTCAGGGCCG AGTCCTGCAG
     ACCATGGTCG ACAGTTTGTT ACTCCACTAT CTCACATAGT GAGTCCCGGC TCAGGACGTC

799  R  P  R  T        C  P  Q       E  V  Y          E  L  M  L       G  C  W       Q  R  E
3541 CGACCCCGCA CGTGCCCCCA GGAGGTGTAT GAGCTGATGC TGGGGTGCTG GCAGCGAGAG
     GCTGGGGCGT GCACGGGGGT CCTCCACATA CTCGACTACG ACCCCACGAC CGTCGCTCTC

819  P  H  M  R        K  N  I        K  G  I         H  T  L  L       Q  N  L       A  K  A
3601 CCCCACATGA GGAAGAACAT CAAGGGCATC CATACCCTCC TTCAGAACTT GGCCAAGGCA
     GGGGTGTACT CCTTCTTGTA GTTCCCGTAG GTATGGGAGG AAGTCTTGAA CCGGTTCCGT

839  S  P  V  Y        L  D  I        L  G  Q
3661 TCTCCGGTCT ACCTGGACAT TCTAGGCTAG GGCCCTTTTC CCCAGACCGA TCCTTCCCAA
     AGAGGCCAGA TGGACCTGTA AGATCCGATC CCGGGAAAAG GGGTCTGGCT AGGAAGGGTT half Xho Sal site from subcloning^
3721 CGTACTCCTC AGACGGGCTG AGAGGATGAA CATCTTTTAA CTGCCGCTGG AGGCCACCAA
     GCATGAGGAG TCTGCCCGAC TCTCCTACTT GTAGAAAATT GACGGCGACC TCCGGTGGTT 3781 GCTGCTCTCC TTCACTCTGA CAGTATTAAC ATCAAAGACT CCGAGAAGCT CTCGACCTGC
     CGACGAGAGG AAGTGAGACT GTCATAATTG TAGTTTCTGA GGCTCTTCGA GAGCTGGACG ^sv40 early poly A
3841 AGAAGCTTGG CCGCCATGGC CCAACTTGTT TATTGCAGCT TATAATGGTT ACAAATAAAG
     TCTTCGAACC GGCGGTACCG GGTTGAACAA ATAACGTCGA ATATTACCAA TGTTTATTTC
```

FIG._13G

```
                ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker
                  ^RI site mutated in
                  ^gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGCGAGG ACTGGGGACC CTGTGACAAG CTTCAGCGCG AACGACCAAC
      AGAGCAGTTA GAGGCGCTCC TGACCCCTGG GACACTGTTC GAAGTCGCGC TTGCTGGTTG ^Start
gD
                                                                M*  G*  G*
   1  TACCCCGATC ATCAGTTATC CTTAAGGTCT CTTTGTGTG  GTGCCGTTCC GTATGGGGGG
      ATGGGGCTAG TAGTCAATAG GAATTCCAGA GAAACACAC  CACGCAAGGC CATACCCCCC T*  A*  A*  R*  L*  G*  A*  V*  I*  L*  F*  V*  V*  I*  V*  G*  L*  H*  G*  V*
1141  GACTGCCGCC AGGTTGGGGG CCGTGATTTT GTTTGTCGTC ATAGTGGGCC TCCATGGGGT
      CTGACGGCGG TCCAACCCCC GGCACTAAAA CAAACAGCAG TATCACCCGG AGGTACCCCA 24  R*  G*  K*  Y*  A*  L*  A   D   A   S   L   K   M   A   D   P   N   R   F   R
1201  CCGGGCAAA TATGCCCTTGG CGGATGCCTC TCTCAAGATG GCCGACCCCA ATCGATTTCG
      GGCGCCGTTT ATACGGAACC GCCTACGGAG AGAGTTCTAC CGGCTGGGGT TAGCTAAAGC
```

FIG._14A

```
                                              ^Xho site and GTA mutated in
                                              ^begin mature trkC
         G   K   D     L   P   V   L   D   Q   L   E   V     C   P   A   N   C   V   C
    44                                                                                                                                                                                                                              
  1261   CGGCAAAGAC    CTTCCGGTCC  TGGACCAGCT  GCTCGAGGTA    TGCCCTGCAA  ATTGTGTCTG
         GCCGTTTCTG    GAAGGCCAGG  ACCTGGTCGA  CGAGCTCCAT    ACGGGACGTT  TAACACAGAC S   K   T     E   I   N   C     R   R   P     D   D   G     N   L   F   P     L   L   E
    64
  1321   CAGCAAGACT    GAGATCAATT  GCCGGCGGCC  GGACGATGGG    AACCTCTTCC  CCCTCCTGGA
         GTCGTTCTGA    CTCTAGTTAA  CGGCCGCCGG  CCTGCTACCC    TTGGAGAAGG  GGGAGGACCT G   Q   D     S   G   N   S     N   G   N     A   N   I     N   I   T   D     I   S   R
    84
  1381   AGGGCAGGAT    TCAGGGAACA  GCAATGGGAA  CGCCAATATC    AACATCACGG  ACATCTCAAG
         TCCCGTCCTA    AGTCCCTTGT  CGTTACCCTT  GCGGTTATAG    TTGTAGTGCC  TGTAGAGTTC N   I   T     S   I   H   I     E   N   W     R   S   L     H   T   L   N     A   V   D
   104
  1441   GAATATCACT    TCCATACACA  TAGAGAACTG  GCGCAGTCTT    CACACGCTCA  ACGCCGTGGA
         CTTATAGTGA    AGGTATGTGT  ATCTCTTGAC  CGCGTCAGAA    GTGTGCGAGT  TGCGGCACCT M   E   L     Y   T   G   L     Q   K   L     T   I   K     N   S   G   L     R   S   I
   124
  1501   CATGGAGCTC    TACACCGGAC  TTCAAAAGCT  GACCATCAAG    AACTCAGGAC  TTCGGAGCAT
         GTACCTCGAG    ATGTGGCCTG  AAGTTTTCGA  CTGGTAGTTC    TTGAGTCCTG  AAGCCTCGTA Q   P   R     A   F   A   K     N   P   H     L   R   Y     I   N   L   S     N   R
   144
  1561   TCAGCCCAGA    GCCTTTGCCA  AGAACCCCCA  TTTGCGTTAT    ATAAACCTGT  CAAGTAACCG
         AGTCGGGTCT    CGGAAACGGT  TCTTGGGGGT  AAACGCAATA    TATTTGGACA  GTTCATTGGC L   T   T     L   S   W   Q     L   F   Q     T   L   S     L   R   E   L     Q   L   E
   164
  1621   GCTCACCACA    CTCTCGTGGC  AGCTCTTCCA  GACGCTGAGT    CTTCGGGAAT  TGCAGTTGGA
```

FIG.-14B

```
                                  CGAGTGGTGT GAGAGCACCG TCGAGAAGGT CTGCGACTCA GAAGCCCTTA ACGTCAACCT

184  Q   N   F   F   N   C   S   C   D   I   R   W   M   Q   L   W   Q   E   Q   G
1681 GCAGAACTTT TTCAACTGCA GCTGTGACAT CCGCTGGATG CAGCTCTGGC AGGAGCAGGG
     CGTCTTGAAA AAGTTGACGT CGACACTGTA GGCGACCTAC GTCGAGACCG TCCTCGTCCC

204  E   A   K   L   N   S   Q   N   L   Y   C   I   N   A   D   G   S   Q   L   P
1741 GGAGGCCAAG CTCAACAGCC AGAACCTCTA CTGCATCAAT GCTGATGGCT CCCAGCTTCC
     CCTCCGGTTC GAGTTGTCGG TCTTGGAGAT GACGTAGTTA CGACTACCGA GGGTCGAAGG

224  L   F   R   M   N   I   S   Q   C   D   L   P   E   I   S   V   S   H   V   N
1801 TCTCTTCCGC ATGAACATCA GTCAGTGTGA CCTTCCTGAG ATCAGCGTGA GCCACGTCAA
     AGAGAAGGCG TACTTGTAGT CAGTCACACT GGAAGGACTC TAGTCGCACT CGGTGCAGTT

244  L   T   V   R   E   G   D   N   A   V   I   T   C   N   G   S   G   S   P   L
1861 CCTGACCGTA CGAGAGGGTG ACAATGCTGT TATCACTTGC AATGGCTCTG GATCACCCCT
     GGACTGGCAT GCTCTCCCAC TGTTACGACA ATAGTGAACG TTACCGAGAC CTAGTGGGGA

264  P   D   V   D   W   I   V   T   G   L   Q   S   I   N   T   H   Q   T   N   L
1921 TCCTGATGTG GACTGGATAG TCACTGGGCT GCAGTCCATC AACACTCACC AGACCAATCT
     AGGACTACAC CTGACCTATC AGTGACCCGA CGTCAGGTAG TTGTGAGTGG TCTGGTTAGA

284  N   W   T   N   V   H   A   I   N   L   T   L   V   N   V   T   S   E   D   N
1981 GAACTGGACC AATGTTCATG CCATCAACTT GACGCTGGTG AATGTGACGA GTGAGGACAA
     CTTGACCTGG TTACAAGTAC GGTAGTTGAA CTGCGACCAC TTACACTGCT CACTCCTGTT

304  G   F   T   L   T   C   I   A   E   N   V   V   G   M   S   N   A   S   V   A
2041 TGGCTTCACC CTGACGTGCA TTGCAGAGAA CGTGGTGGGC ATGAGCAATG CCAGTGTTGC
     ACCGAAGTGG GACTGCACGT AACGTCTCTT GCACCACCCG TACTCGTTAC GGTCACAACG
```

FIG._14C

```
324   L   T   V   Y   Y   P   P   R   V   V   S   L   E   E   P   E   L   R   L   E
2101  CCTCACTGTC TACTATCCCC CACGTGTGGT GAGCCTGGAG CTCGAGCCTGAGC TGCGCCTGGA
      GGAGTGACAG ATGATAGGGG GTGCACACCA CTCGGACTCG ACGCGGACCT

344   H   C   I   E   F   V   V   R   G   N   P   P   P   T   L   H   W   L   H   N
2161  GCACTGCATC GAGTTTGTGG TGCGTGGCAA CCCCCCACCA ACGCTGCACT GGCTGCACAA
      CGTGACGTAG CTCAAACACC ACGCACCGTT GGGGGGTGGT TGCGACGTGA CCGACGTGTT

364   G   Q   P   L   R   E   S   K   I   I   H   V   E   Y   Y   Q   E   G   E   I
2221  TGGGCAGCCT CTGCGGGAGT CCAAGATCAT CCATGTGGAA TACTACCAAG AGGGAGAGAT
      ACCCGTCGGA GACGCCCTCA GGTTCTAGTA GGTACACCTT ATGATGGTTC TCCCTCTCTA

384   S   E   G   C   L   L   F   N   K   P   T   H   Y   N   N   G   N   Y   T   L
2281  TTCCGAGGGC TGCCTGCTCT TCAACAAGCC CACCCACTAC AACAATGGCA ACTATACCCT
      AAGGCTCCCG ACGGACGAGA AGTTGTTCGG GTGGGTGATG TTGTTACCGT TGATATGGGA

404   I   A   K   N   P   L   G   T   A   N   Q   T   I   N   G   H   F   L   K   E
2341  CATTGCCAAA AACCCACTGG GCACAGCCAA CCAGACCATC AATGGCCACT TCCTCAAGGA
      GTAACGGTTT TTGGGTGACC CGTGTCGGTT GGTCTGGTAG TTACCGGTGA AGGAGTTCCT

^begin ecd insert                    ^end ecd insert
424   P   F   P   E   S   T   D   N   F   I   L   F   D   E   V   S   P   T   P   P
2401  GCCCTTTCCA GAGAGCACGG ATAACTTTAT CTTGTTTGAC GAAGTGAGTC CCACACCTCC
      CGGGAAAGGT CTCTCGTGCC TATTGAAATA GAACAAACTG CTTCACTCAG GGTGTGGAGG ^begin TM
444   I   T   V   T   H   K   P   E   E   D   T   F   G   V   S   I   A   V   G   L
2461  TATCACTGTG ACCCACAAAC CAGAAGAAGA CACTTTTGGG GTATCCATAG CAGTTGGACT
```

*FIG._14D*

```
                      ATAGTGACAC TGGGTGTTTG GTCTTCTTCT GTGAAAACCC CATAGGTATC GTCAACCTGA
                                                                          ^end TM
      464         A   A   F   A   C   V   L   L   V   V   L   F   V   M   I   N   K   Y   G   R
      2521        TGCTGCTTTT GCCTGTGTCC TGTTGGTGGT TCTCTTCGTC ATGATCAACA AATATGGTCG
                  ACGACGAAAA CGGACACAGG ACAACCACCA AGAGAAGCAG TACTAGTTGT TTATACCAGC 484         R   S   K   F   G   M   K   G   P   V   A   V   I   S   G   E   E   D   S   A
      2581        ACGGTCCAAA TTTGGAATGA AGGGTCCCGT GGCTGTCATC AGTGGTGAGG AGGACTCAGC
                  TGCCAGGTTT AAACCTTACT TCCCAGGGCA CCGACAGTAG TCACCACTCC TCCTGAGTCG 504         S   P   L   H   H   I   N   H   G   I   T   T   P   S   S   L   D   A   G   P
      2641        CAGCCCACTG CACCACATCA ACCACGGCAT CACCACGCCC TCGTCACTGG ATGCCGGGCC
                  GTCGGGTGAC GTGGTGTAGT TGGTGCCGTA GTGGTGCGGG AGCAGTGACC TACGGCCCGG 524         D   T   V   V   I   G   M   T   R   I   P   V   I   E   N   P   Q   Y   F   R
      2701        CGACACTGTG GTCATTGGCA TGACTCGCAT CCCTGTCATT GAGAACCCCC AGTACTTCCG
                  GCTGTGACAC CAGTAACCGT ACTGAGCGTA GGGACAGTAA CTCTTGGGGG TCATGAAGGC 544         Q   G   H   N   C   H   K   P   D   T   Y   V   Q   H   I   K   R   D   I
      2761        TCAGGGACAC AACTGCCACA AGCCGGACAC GTATGTGCAG CACATTAAGA GGAGAGACAT
                  AGTCCCCTGT TTGACGGTGT TCGGCCTGTG CATACACGTC GTGTAATTCT CCTCTCTGTA ^begin TK
      564         V   L   K   R   E   L   G   E   G   A   F   G   K   V   F   L   A   E   C   Y
      2821        CGTGCTGAAG CGAGAACTGG GTGAGGGAGC CTTTGGAAAG GTCTTCCTGG CCGAGTGCTA
                  GCACGACTTC GCTCTTGACC CACTCCCTCG GAAACCTTTC CAGAAGGACC GGCTCACGAT
```

*FIG._14E*

```
584  N   L   S      P   T   K   D      K   M   L      V   A   V      K   A   L   K      D   P   T
2881 CAACCTCAGC  CCGACCAAGG  ACAAGATGCT  TGTGGCTGTG  AAGGCCCTGA  AGGATCCCAC
     GTTGGAGTCG  GGCTGGTTCC  TGTTCTACGA  ACACCGACAC  TTCCGGGACT  TCCTAGGGTG

604  L   A   A      R   K   D   F      Q   R   E      A   E   L      L   T   N   L      Q   H   E
2941 CCTGGCTGCC  CGGAAGGATT  TCCAGAGGGA  GGCCGAGCTG  CTCACCAACC  TGCAGCATGA
     GGACCGACGG  GCCTTCCTAA  AGGTCTCCCT  CCGGCTCGAC  GAGTGGTTGG  ACGTCGTACT

624  H   I   V      K   F   Y   G      V   C   G      D   G   D      P   L   I   M      V   F   E
3001 GCACATTGTC  AAGTTCTATG  GAGTGTGCGG  CGATGGGGAC  CCCCTCATCA  TGGTCTTTGA
     CGTGTAACAG  TTCAAGATAC  CTCACACGCC  GCTACCCCTG  GGGGAGTAGT  ACCAGAAACT

644  Y   M   K      H   G   D   L      N   K   F      L   R   A      H   G   P   D      A   M   I
3061 ATACATGAAG  CATGGAGACC  TGAATAAGTT  CCTCAGGGCC  CATGGGCCAG  ATGCAATGAT
     TATGTACTTC  GTACCTCTGG  ACTTATTCAA  GGAGTCCCGG  GTACCCGGTC  TACGTTACTA

664  L   V   D      G   Q   P   R      Q   A   K      G   E   L      G   L   S   Q      M   L   H
3121 CCTTGTGGAT  GGACAGCCAC  GCCAGGCCAA  GGGTGAGCTG  GGGCTCTCCC  AAATGCTCCA
     GGAACACCTA  CCTGTCGGTG  CGGTCCGGTT  CCCACTCGAC  CCCGAGAGGG  TTTACGAGGT

684  I   A   S      Q   I   D   L      A   S   L      Y   L   A      S   Q   H   F      V   H   R
3181 CATTGCCAGT  CAGATCGCCT  CGGGTATGGT  GTACCTGGCC  TCCCAGCACT  TTGTGCACCG
     GTAACGGTCA  GTCTAGCGGA  GCCCATACCA  CATGGACCGG  AGGGTCGTGA  AACACGTGGC

704  D   L   A      T   R   N   C      L   V   G      A   N   L      L   V   K   I      G   D   F
3241 AGACCTGGCC  ACCAGGAACT  GCCTGGTTGG  AGCGAATCTG  CTAGTGAAGA  TTGGGGACTT
     TCTGGACCGG  TGGTCCTTGA  CGGACCAACC  TCGCTTAGAC  GATCACTTCT  AACCCTGAA
                                                    ^TK insert site
724  G   M   S      R   D   V   Y      S   T   D      Y   Y   R      V   G   G   H      T   M   L
```

FIG._14F

```
3301 CGGCATGTCC AGAGATGTCT ACAGCACGGA TTATTACAGG GTGGGAGGAC ACACCATGCT
     GCCGTACAGG TCTCTACAGA TGTCGTGCCT AATAATGTCC CACCCTCCTG TGTGGTACGA

744       P  I  R     W  M  P  P     E  S  I     M  Y  R     K  F  T  T     E  S  D
3361 CCCCATTCGC TGGATGCCTC CTGAAAGCAT CATGTACCGG AAGTTCACTA CAGAGAGTGA
     GGGGTAAGCG ACCTACGGAG GACTTTCGTA GTACATGGCC TTCAAGTGAT GTCTCTCACT

764     V  W  S     F  G  V  I     L  W  E     I  F  T     Y  G  K  Q     P  W  F
3421 TGTATGGAGC TTCGGGGTGA TCCTCTGGGA GATCTTCACC TATGGAAAGC AGCCATGGTT
     ACATACCTCG AAGCCCCACT AGGAGACCCT CTAGAAGTGG ATACCTTTCG TCGGTACCAA

784     Q  L  S     N  T  E  V     I  E  C     I  T  Q     G  R  V  L     E  R  P
3481 CCAACTCTCA AACACGGAGG TCATTGAGTG CATTACCCAA GGTCGTGTTT TGGAGCGGCC
     GGTTGAGAGT TTGTGCCTCC AGTAACTCAC GTAATGGGTT CCAGCACAAA ACCTCGCCGG

804     R  V  C     P  K  E  V     Y  D  V     M  L  G     C  W  Q  R     E  P  Q
3541 CCGAGTCTGC CCCAAAGAGG TGTACGATGT CATGCTGGGG TGCTGGCAGA GGGAACCACA
     GGCTCAGACG GGGTTTCTCC ACATGCTACA GTACGACCCC ACGACCGTCT CCCTTGGTGT

824     Q  R  L     N  I  K  E     I  Y  K     I  L  H     A  L  G  K     A  T  P
3601 GCAGCGGTTG AACATCAAGG AGATCTACAA AATCCTCCAT GCTTTGGGGA AGGCCACCCC
     CGTCGCCAAC TTGTAGTTCC TCTAGATGTT TTAGGAGGTA CGAAACCCCT TCCGGTGGGG
                                    ^stop
                                    R1 site removed with cut and fill^

844     I  Y  L     D  I  L  G     O
3661 AATCTACCTG GACATTCTTG GCTAGTGGTG GCTGGTGGTC ATGAATTAAT TCAATCGATG
     TTAGATGGAC CTGTAAGAAC CGATCACCAC CGACCACCAG TACTTAATTA AGTTAGCTAC
                                              ^sv40 early poly A
3721 GCCGCCATGG CCCAACTTGT TTATTGCAGC TTATAAATGGT TACAAATAAA GCAATAGCAT
     CGGCGGTACC GGGTTGAACA AATAACGTCG AATATTACCA ATGTTTATTT CGTTATCGTA
```

FIG._14G

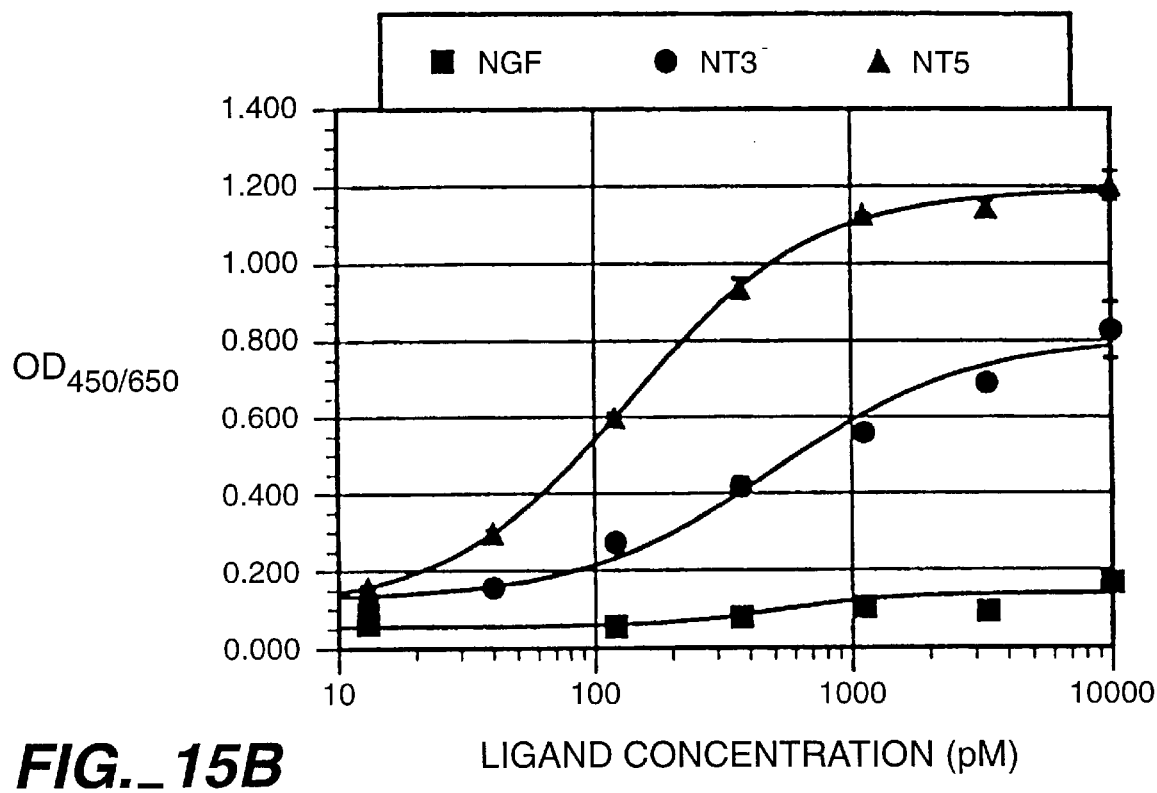
FIG._15B
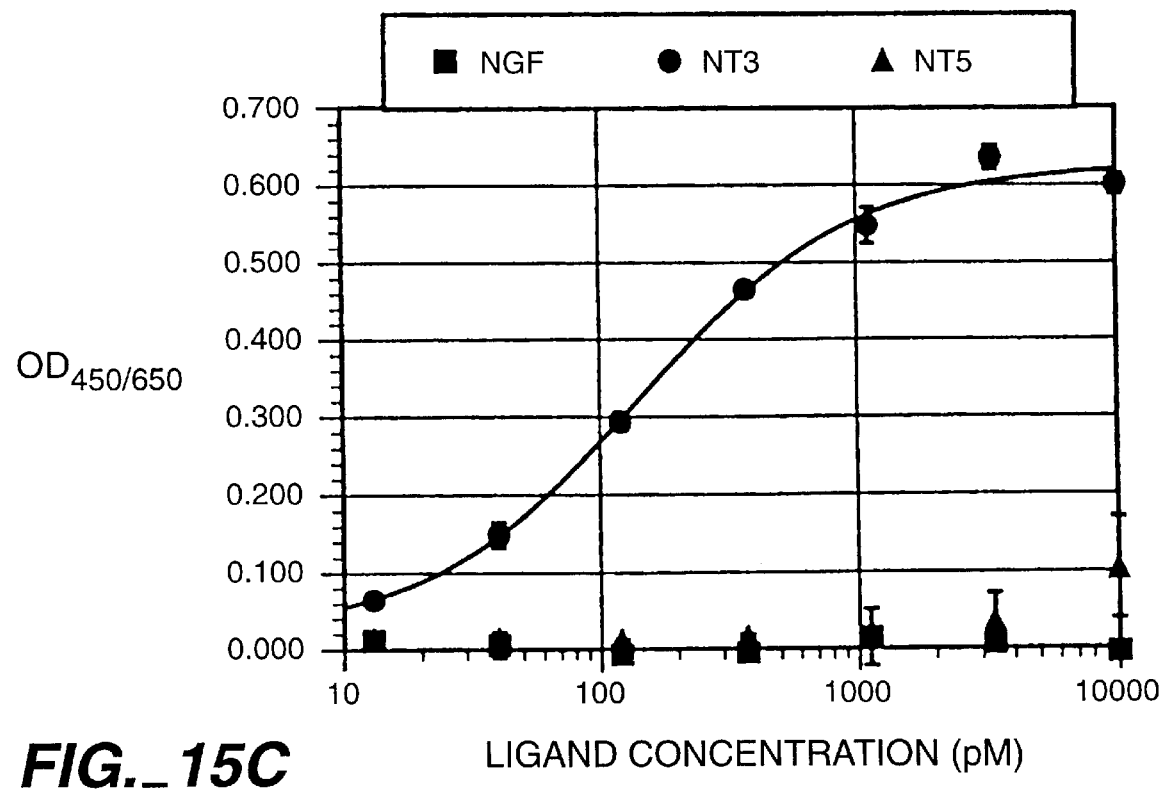
FIG._15C

FIG._16A

```
                                                                    aluI
                                                    sau3AI  pvuII
                                                    mboI/ndeII[dam-]
                                                      dpnI[dam+]
                                                       pvuI/bspCI
                                                 pleI dpnII[dam-]
                                                  hinfI  taqI[dam-]
                                         rmaI    mcrI    nspBII
                                          maeI   taqI[dam-]
         aluI
         sstI
         sacI
         hgiJII
         hgiAI/aspHI
         ecl136II
         bsp1286
         bsiHKAI
         bmyI
         banII
     taqI
  1  TTCGAGCTCG CCCGACATTG ATTATTGACT AGAGTCGATC GACAGCTGTG GAATGTGTGT CAGTTAGGGT
     AAGCTCGAGC GGGCTGTAAC TAATAACTGA TCTCAGCTAG CTGTCGACAC CTTACACACA GTCAATCCCA nlaIV                                          sfaNI            scrFI
                   scrFI                                         ppu10I           mvaI
                   mvaI                                          nsiI/avaIII      ecoRII
                   ecoRII                                        nlaIII           dsaV
                   dsaV                                           sphI            bstNI
                   bstNI                                          nspI            apyI
                   apyI[dcm+]                                     nspHI           sexAI
                   bsaJI
 71  GTGGAAAGTC CCCAGGCTCC CCAGCAGGCA GAAGTATGCA AAGCATGCAT CTCAATTAGT CAGCAACCAG
     CACCTTTCAG GGGTCCGAGG GGTCGTCCGT CTTCATACGT TTCGTACGTA GAGTTAATCA GTCGTTGGTC
```

FIG._16B

```
                                                                                    nlaIII
                                                                                    styI
                                          sfaNI                                     ncoI
                      nlaIV                                             bslI dsaI
                                      nsiI/avaIII ppuI01                acil bsaJI
             scrFI                    nlaIII        sphI
               mvaI                                 nspI
           ecoRII                                   nspHI
           dsaV
              bstNI
              apyI[dcm+]
              bsaJI
    [dcm+]
141 GTGTGGAAAG TCCCCAGGCT CCCCAGCAGG CAGAAGTATG CAAAGCATGC ATCTCAATTA GTCAGCAACC
    CACACCTTTC AGGGGTCCGA GGGGTCGTCC GTCTTCATAC GTTTCGTACG TAGAGTTAAT CAGTCGTTGG acil bsrI acil
              acil                      CGCCCAGTTC CGCCCATTCT CGCCCCCATG
                     acil      fokI                                    
                          acil                                         
211 ATAGTCCCGC CCCTAACTCC GCCCATCCCG CCCCTAACTC CGCCCAGTTC CGCCCATTCT CGCCCCCATG
    TATCAGGGCG GGGATTGAGG CGGGTAGGGC GGGGATTGAG GCGGGTCAAG GCGGGTAAGA GCGGGGGTAC fnu4HI
                                     bglI
                                     sfiI
                                     haeIII/palI
                                     mnlI  mnlI    ddeI
                     haeIII/palI bsaJI mnlI  aluI
                     mnlI bsaJI acil   haeIII/palI
                                                                                mnlI
281 GCTGACTAAT TTTTTTTATT TATGCAGAGG CCGAGGCCGC CTCGGCCCTC GAGCTATTCC AGAAGTAGTG
    CGACTGATTA AAAAAAATAA ATACGTCTCC GGCTCCGGCG GAGCCGGAGA CTCGATAAGG TCTTCATCAC
```

```
                                                                  haeIII/palI
                                                                  mcrI
                                                         aluI     eagI/xmaIII/eclXI
                                                         rmaI     eaeI
                                           haeIII/palI   maeI     cfrI
                                   avrII                 nheI     mspI
                            rmaI   blnI                  aluI     hpaII
                            styI   bsaJI
                            stuI
                     mnlI   haeI
              mnlI          mnlI  maeI
351 AGGAGGCTTT TTTGGAGGCC TAGGCTTTTG CAAAAAGCTA GCTTATCCGG
    TCCTCCGAAA AAACCTCCGG ATCCGAAAAC GTTTTTCGAT CGAATAGGCC tfiI
                         hinFI
    scrFI         aciI                                                              aciI
    nciI          thaI                                       maeII   rsaI
    mspI          fnuDII/mvnI                                maeIII  csp6I  scfI
    hpaII         bstUI
    dsaV          bsh1236I
    cauII
401 CCGGGAACGG TGCATTGGAA CGGGATTCC CCGTGCCAAG AGTGACGTAA GTACCGCCTA TAGAGCGATA
    GGCCCTTGCC ACGTAACCTT GGCCCTAAGG GGCACGGTTC TCACTGCATT CATGGCGGAT ATCTCGCTAT
                                                            ^splice donor fnu4HI
          bbvI
          nspBII                                                                    pflMI
    mnlI  aciI         nlaIII  taqI                                  sfaNI          bslI
471 AGAGGATTTT ATCCCCGCTG CCATCATGGT TCGACCATTG AACTGCATCG TCGCCGTGTC CCAAAATATG
    TCTCCTAAAA TAGGGGCGAC GGTAGTACCA AGCTGGTAAC TTGACGTAGC AGCGGCACAG GGTTTTATAC
                DHFR ATG^
```

```
                                          haeIII/palI
                                          haeI
                                   scrFI
                                   mvaI        bsrBI
                                   ecoRII
                                   dsaV
                                   bstNI  aciI                            rsaI
                            bsmAI  apyI[dcm+]            xmnI             csp6I
                            bsaI   bsaJI  mnlI  ddeI     asp700           scaI
541  GGGATTGGCA AGAACGGAGA CCTACCCTGG CCTCCGCTCA GGAACGAGTT CAAGTACTTC CAAAGAATGA
     CCCTAACCGT TCTTGCCTCT GGATGGGACC GGAGGCGAGT CCTTGCTCAA GTTCATGAAG GTTTCTTACT scrFI
                                                                   mvaI
                                                                   ecoRII
                                                                   dsaV
                                             tfiI                  bstNI
                                             hinfI                 apyI[dcm+]
        eco57I                         alwNI      hphI             sexAI         ddeI
        mboII
        earI/ksp632I
        mnlI
611  CCACAACCTC TTCAGTGGAA GGTAAACAGA ATCTGGTGAT TATGGGTAGG AAAACCTGGT TCTCCATTCC
     GGTGTTGGAG AAGTCACCTT CCATTTGTCT TAGACCACTA ATACCCATCC TTTTGGACCA AGAGGTAAGG tfiI     tru9I
        hinfI    mseI       ddeI
        mboII taqI  ahaIII/draI   aseI/asnI/vspI                   bslI    mnlI
681  TGAGAAGAAT CGACCTTTAA AGGACAGAAT TAATATAGTT CTCAGTAGAG AACTCAAAGA ACCACCACGA
     ACTCTTCTTA GCTGGAAATT TCCTGTCTTA ATTATATCAA GAGTCATCTC TTGAGTTTCT TGGTGGTGCT
```

FIG._16E

```
       sstI
       sacI
       hgiJII
       hgiAI/aspHI
       ecl136II
       bsp1286
       bsiHKAI
       bmyI                                          tru9I           mspI
       banII                                         aflII/bfrI      hpaII
       aluI              bstXI    fokI sfaNI mseI                    bsaWI
751 GGAGCTCATT TTCTTGCCAA AAGTTTGGAT GATGCCTTAA GACTTATTGA ACAACCGGAA TTGGCAAGTA
    CCTCGAGTAA AAGAACGGTT TTCAAACCTA CTACGGAATT CTGAATAACT TGTTGGCCTT AACCGTTCAT haeIII/palI
                                                                        haeI
                                                        scrFI       scrFI
                                                        mvaI        mvaI
                                                        ecoRII      ecoRII
                                                        dsaV   tfiI dsaV
                                                        bstNI  nlaIII     bstNI    ddeI
                        mnlI                            apyI[dcm+] hinfI apyI[dcm+]
    accI nlaIII
821 AAGTAGACAT GGTTTGGATA GTCGGAGGCA GTTCTGTTTA CCAGGAAGCC ATGAATCAAC CAGGCCACCT
    TTCATCTGTA CCAAACCTAT CAGCCTCCGT CAAGACAAAT GGTCCTTCGG TACTTAGTTG GTCCGGTGGA
```

FIG._16F

```
                                         nlaIII
                              sau3AI
                            mboI/ndeII[dam-]
                          dpnI[dam+]                                              maeII
                          dpnII[dam-]                                           aflIII
      pleI            maeIII alwI[dam-]    apoI    maeIII
      hinfI
891  TAGACTCTTT GTGACAAGGA TCATGCAGGA ATTGAAAGT GACACGTTTT TCCCAGAAAT TGATTTGGGG
     ATCTGAGAAA CACTGTTCCT AGTACGTCCT TAAACTTTCA CTGTGCAAAA AGGGTCTTTA ACTAAACCCC
                                hgaI
                              hinlI/acyI
                                ahaII/bsaHI
                          scrFI
                          mvaI          mnlI
                          ecoRII
                          dsaV
                          bstNI      ecoNI
                          apyI[dcm+]              mnlI
              mnlI        bsaJI       bslI ddeI
961  AAATATAAAC CTCTCCCAGA ATACCCAGGC GTCCTCTCTG
     TTTATATTTG GAGAGGGTCT TATGGGTCCG CAGGAGAGAC
```

FIG.—16G

```
     scrFI
     mvaI
     ecoRII
     dsaV
     bstNI
     apyI[dcm+]
     sau96I
     avaII
     asuI   mnlI         sfaNI                        accI        mboII                                                    sfaNI
1001 AGTCCAGGA GGAAAAAGGC ATCAAGTATA AGTTTGAAGT CTACGAGAAG AAAGACTAAC AGGAAGATGC
     TCCAGGTCCT CCTTTTTCCG TAGTTCATAT TCAAACTTCA GATGCTCTTC TTTCTGATTG TCCTTCTACG
                                                                       ^END DHFR nlaIII
                                                                     styI
                                                                     ncoI
                                                                     dsaI
                                                ppul0I               bsaJI
                            mnlI    aluI  nsiI/avaIII
1071 TTTCAAGTTC TCTGCTCCCC TCCTAAAGCT ATGCATTTTT ATAAGACCAT GGGACTTTTG
     AAAGTTCAAG AGACGAGGGG AGGATTTCGA TACGTAAAAA TATTCTGGTA CCCTGAAAAC
```

FIG._16H

```
             styI
             bsaJI
       sau3AI                    fnu4HI
       mboI/ndeII[dam-]          aciI
       dpnI[dam+]                thaI
       dpnII[dam-]               fnuDII/mvnI tru9I
       alwI[dam-]                bstUI       mseI
       bstYI/xhoII               bsh1236I    aseI/asnI/vspI
1131 CTGGCTTTAG ATCCCCCTTGG CTTCGTTAGA ACGCGGCTAC AATTAATACA TAACCTTATG TATCATACAC
     GACCGAAATC TAGGGGAACC GAAGCAATCT TGCGCCGATG TTAATTATGT ATTGGAATAC ATAGTATGTG
                                                                         sau96I
                                                                         avaII
                                                                         asuI
                                                                         scrFI
                                                                         mvaI
                                                                         ecoRII
                                                                         dsaV
                                                                         bstNI
                                                                         apyI[dcm+]
          maeIII                                                bslI bsaJI
          hphI   scfI   fokI
1201 ATACGATTTA GGTGACACTA TAGATAACAT CCACTTTGCC TTTCTCTCCA CAGGTGTCCA CTCCCAGGTC
     TATGCTAAAT CCACTGTGAT ATCTATTGTA GGTGAAACGG AAAGAGAGGT GTCCACAGGT GAGGGTCCAG
```

FIG._16I

```
                                                                scrFI
                                                                ncil
                                                                mspI
                                                                hpaII
                                                                dsaV
                                                                xmaI/pspAI
                                                                smaI
                                                                scrFI
                                                                ncil
                                                                dsaV
                                                                cauII
                                                                bsaJI
                                                                avaI
                                                         sau3AI
                                                         mboI/ndeII[dam-]
                                                         dpnI[dam+]
                                                         dpnII[dam-]
                                                  nlaIV cauII
                                            pleI  bstYI/xhoII
                                            hinfI       bamHI bsaJI
                               taqI  rmaI               alwI[dam-]
                               salI  maeI
             scfI              hincII/hindII alwI[dam-]
             aluI  pstI        accI  xbaI  mnlI bsaJI
       hindIII bspMI
       ddeI  bsgI
 mnlI
 bsaJI
1271 CAACTGCACC TCGGTTCTAA GCTTCTGCAG GTCGACTCTA GAGGATCCCC
     GTTGACGTGG AGCCAAGATT CGAAGACGTC CAGCTGAGAT CTCCTAGGGG
```

FIG._16J

```
                                          sau96I
                              acil      haeIII/palI
                              fnu4HI      asuI
                              bglI      nlaIII
                              sfiI      styI
                              eaeI      ncoI                                                   aluI
                              cfrI      dsaI                                              fnu4HI
     ecoRI       taqI haeIII/palI                                                    bbvI          maeIII
     apoI   claI/bsp106 bsaJI                                                                                     
1321 GGGGAATTCA ATCGATGGCC GCCATGGCCC AACTTGTTTA TTGCAGCTTA TAATGGTTAC AAATAAAGCA
     CCCCTTAAGT TAGCTACCGG CGGTACCGGG TTGAACAAAT AACGTCGAAT ATTACCAATG TTTATTTCGT
                                            ^sv40
                                                                            rmaI
             sfaNI                                                      bsmI maeI
             apoI
1391 ATAGCATCAC AAATTTCACA AATAAAGCAT TTTTTTCACT GCATTCTAGT TGTGGTTTGT CCAAACTCAT
     TATCGTAGTG TTTAAAGTGT TTATTTCGTA AAAAAAGTGA CGTAAGATCA ACACCAAACA GGTTTGAGTA
```

FIG._16K

```
                                              sau3AI
                                              mboI/ndeII[dam-]
                                              dpnI[dam+]
                                              dpnII[dam-]
                                              pvuI/bspCI
                                              mcrI
                                              taqI[dam-]   tru9I
                                              claI/bsp106[dam-]
                                              sau3AI       mseI
                                              mboI/ndeII[dam-]
                                              dpnI[dam+] xmnI
                                              dpnII[dam-]  aseI/asnI/vspI
                         nlaIII  alwI[dam-]  asp700
                                                                                                    rsaI
                                                                                                    csp6I
                                                                                                    nlaIV
                 haeIII/palI                                                                        kpnI
                 haeI                                                                               hgiCI
         styI                                                                                       banI
         ncoI                                                                              asp718   mnlI
  fnu4HI dsaI                                                                              acc65I   ddeI  aciI
  bbvI   bsaJI                                              sv40 origin^
  hinPI  nlaIII             mnlI            mnlI
  hhaI/cfoI
1461 CGGCGCAGCA CCATGGCCTG AAATAACCTC TGAAAGAGGA ACTTGGTTAG GTACCTTCTG AGGCGGAAAG
     GCCGCGTCGT GGTACCGGAC TTTATTGGAG ACTTTCTCCT TGAACCAATC CATGGAAGAC TCCGCCTTTC
1501 CAATGTATCT TATCATGTCT GGATCGATCG GGAATTAATT
     GTTACATAGA ATAGTACAGA CCTAGCTAGC CCTTAATTAA
```

FIG._16L

```
                                                                nlaIV
                                                                scrFI
                                                                mvaI
                                                                ecoRII
                                                                dsaV
                                                                bstNI
                                                                apyI[dcm+]
           aluI                                                 bsaJI
           pvuII
           nspBII
1571 AACCAGCTGT GGAATGTGTG TCAGTTAGGG TGTGGAAAGT CCCCAGGCTC CCCAGCAGGC AGAAGTATGC
     TTGGTCGACA CCTTACACAC AGTCAATCCC ACACCTTTCA GGGGTCCGAG GGGTCGTCCG TCTTCATACG nlaIV
                               scrFI     scrFI
           sfaNI               mvaI
           ppu10I              ecoRII    ecoRII
     nsiI/avaIII               dsaV      dsaV
         nlaIII                          bstNI            bstNI
           sphI                          apyI[dcm+]       apyI[dcm+]
           nspI                          sexAI            bsaJI
           nspHI
1641 AAAGCATGCA TCTCAATTAG TCAGCAACCA GGTGTGGAAA GTCCCCAGGC TCCCCAGCAG GCAGAAGTAT
     TTTCGTACGT AGAGTTAATC AGTCGTTGGT CCACACCTTT CAGGGGTCCG AGGGGTCGTC CGTCTTCATA sfaNI
           ppu10I
     nsiI/avaIII
         nlaIII
           sphI                                               aciI
           nspI                             aciI     aciI    fokI           aciI
           nspHI                            aciI
1711 GCAAAGCATG CATCTCAATT AGTCAGCAAC CATAGTCCCG CCCCTAACTC CGCCCATCCC GCCCCTAACT
     CGTTTCGTAC GTAGAGTTAA TCAGTCGTTG GTATCAGGGC GGGGATTGAG GCGGGTAGGG CGGGGATTGA
```

FIG._16M

```
                                     nlaIII
                                      styI
                                      ncoI
                               bslI dsaI                              styI
                               acil bsaJI                             bsaJI
          bsrI                                              mnlI      blnI
     asiI      aciI  CCGCCCAGTT TCCGCCCCAT GGCTGACTAA TTTTTTTTAT TTATGCAGAG   avrII
1781 CCGCCCAGTT TCCGCCCCAT GGCTGACTAA TTTTTTTTAT TTATGCAGAG                   haeIII/palI
     GGCGGGTCAA AGGCGGGGTA CCGACTGATT AAAAAAAATA AATACGTCTC                   stuI
                                                                              haeI
                fnu4HI                                              mnlI      mnlI
                bglI                                       mnlI
                sfiI
                haeIII/palI
           mnlI            ddeI
     haeIII/palI  bsaJI mnlI   aluI
       bsaJI aciI  haeIII/palI
1841 GCCGAGGCCG CCTCGGCCTC TGAGCTATTC CAGAAGTAGT GAGGAGGCTT TTTTGGAGGC
     CGGCTCCGGC GGAGCCGGAG ACTCGATAAG GTCTTCATCA CTCCTCCGAA AAAACCTCCG
```

FIG. 16N

```
                                                                                            hinPI
                                          aciI                                              hhaI/cfoI
                                          haeIII/palI                                       thaI
                                   mcrI   eagI/xmaIII/eclXI fnuDII/mvnI
                                                                   bstUI                              bspMI
                                   taqI eaeI                       hinPI                              scfI
                                   xhoI notI                       hhaI/cfoI tru9I                    pstI
                                   paeR7I cfrI    tru9I            ascI        ahaIII/draI
                                   avaI  fnu4HI  pacI                                         bsgI
                             mnlI  aciI  mseI tru9I bsh1236I mseI  mseI bssHII swaI           sse8387I
        rmaI   aluI maeIII bsrBI fnu4HI
        maeI
1901 CTAGGCTTTT GCAAAAAGCT GTTACCTCGA GCGGCCGCTT AATTAAGGCG CGCCATTTAA ATCCTGCAGG
     GATCCGAAAA CGTTTTTCGA CAATGGAGCT CGCCGGCGAA TTAATTCCGC GCGGTAAATT TAGGACGTCC
                ^start pUC118
                           ^linearization linker inserted into HpaI site scrFI
                                                                         mvaI
                                                                         ecoRII
                                                                         dsaV
                                       haeIII/palI                       bstNI
                                       eaeI                              apyI[dcm+]                 tru9I
maeIII                                 cfrI             maeIII           bsaJI    maeIII            mseI
        aluI   bsrI                    bsrI   maeII     bsrI    ACGTCGTGAC CTGGCGTTAC CCAACTTAAT
1971 TAACAGCTTG GCACTGGCCG TCGTTTTACA            TGtGAAAAACC
     ATTGTCGAAC CGTGACCGGC AGCAAAATGT           ACtCTTTTGG           TGCAGCACTG GACCGCAATG GGTTGAATTA
```

FIG._160

```
                                                              sau3AI
                                                     sau96I   mboI/ndeII[dam-]
                                            haeIII/palI
                                    asuI    dpnI[dam+]
                                            mnlI        dpnII[dam-]
                 aluI                       mboII  aciI pvuI/bspCI
                 pvuII                      earI/ksp632I mcrI
          fnu4HI nspBII
          bbvI  fokI
2041 CGCCTTGCAG CACATCCCCC CTTCGCCAGC TGGCGTAATA GCGAAGAGGC CCGCACCGAT
     GCGGAACGTC GTGTAGGGGG GAAGCGGTCG ACCGCATTAT CGCTTCTCCG GGCGTGGCTA
                                     hinPI
                                     hhaI/cfoI
                                     nlaIV
                                     narI
                                     kasI
                                     hinlI/acyI
                                     hgiCI
                                     haeII    aciI
                                     banI   sfaNI
                                     ahaII/bsaHI
                                                                         sfaNI
                         bglI
2101 CGCCCTTCCC AACAGTTGCG TAGCCTGAAT GGGCGAATGGC GCCTGATGCG GTATTTCTC CTTACGCATC
     GCGGGAAGGG TTGTCAACGC ATCGGACTTA CCCGCTTACCG CGGACTACGC CATAAAAGAG GAATGCGTAG
```

FIG._16P

```
                                                             hinPI
                                                             thaI
                                                             fnuDII/mvnI
                                                             bstUI scfI             hinPI
                                                             bsh1236I               hhaI/cfoI
                                         rsaI hhaI/cfoI      fnu4HI
                                         csp6I    bslI       aciI
         aciI       aciI    maeII    ATACGTCAAA GCAACCATAG TACGCGCCCT GTAGCGGCGC
2171 TGTGCGGGTAT TTCACACCGC ATACGTCAAA GCAACCATAG TACGCGCCCT GTAGCGGCGC
     ACACGCCATA AAGTGTGGCG TATGCAGTTT CGTTGGTATC ATGCGCGGGA CATCGCCGCG fnu4HI
            thaI        hinPI
            fnuDII/mvnI hhaI/cfoI
            bctUI       thaI
            hinPI aciI  fnuDII/mvnI
            hhaI/cfoI   bstUI
         tru9I aciI     bsh1236I          aciI
         mseI bsh1236I  maeIII bbvI maeIII
2231 ATTAAGCGCG GCGGGTGTGG TGGTTACGCG CAGCGTGACC GCTACACTTG
     TAATTCGCGC CGCCCACACC ACCAATGCGC GTCGCACTGG CGATGTGAAC
```

```
                                                                           nlaIV
                                                                           hgiJII
                                                                           bsp1286
                                          mspI                             bmyI
                                          hpaII                            banII
                                          naeI         aluI
                         mboII            maeII cfr10I
2301 CCTTTCGCTT TCTTCCCTTC CTTTCTCGCC ACGTTCGCCG GCTTTCCCCG TCAAGCTCTA AATCGGGGGC
     GGAAAGCGAA AGAAGGGAAG GAAAGAGCGG TGCAAGCGGC CGAAAGGGGC AGTTCGAGAT TTAGCCCCCG
```

FIG._16Q

```
                                                   mnlI
                                                   nlaIV
                                                   hgiCI
                                                   banI taqI                                 hphI
         nlaIV         GTTCCGATTT AGTGCTTTAC GGCACCTCGA CCCCAAAAAA CTTGATTTGG
2371 TCCCTTTAGG GTTCCGATTT AGTGCTTTAC GGCACCTCGA CCCCAAAAAA CTTGATTTGG
     AGGGAAATCC CAAGGCTAAA TCACGAAATG CCGTGGAGCT GGGGTTTTTT GAACTAAACC maeII    haeIII/palI                                    maeII pleI
            draIII   sau96I                                         drdI hinfI maeII
            bsaAI    asuI
2401 GTGATGGTTC ACGTAGTGGG CCATCGCCCT GATAGACGGT TTTTCGCCCT TTGACGTTGG AGTCCACGTT
     CACTACCAAG TGCATCACCC GGTAGCGGGA CTATCTGCCA AAAAGCGGGA AACTGCAACC TCAGGTGCAA bslI
        tru9I    pleI                                 bslI   avaI
        mseI     hinfI          bsrI
2501 CTTTAATAGT GGACTCTTGT TCCAAACTGG AACCTATCT CGGGCTATTC TTTTGATTTA
     GAAATTATCA CCTGAGAACA AGGTTTGACC TTGGGATAGA GCCCGATAAG AAAACTAAAT tru9I
                             tru9I                            mseI
                 haeIII/palI  mseI    aluI  mseI   apoI
2571 TAAGGGATTT TGCCGATTTC GGCCTATTGG TTAAAAAATG AGCTGATTTA ACAAAAATTT
     ATTCCCTAAA ACGGCTAAAG CCGGATAACC AATTTTTTAC TCGACTAAAT TGTTTTTAAA
```

FIG._16R

```
                                                         hgiAI/aspHI
                                                         bsp1286
                                                         bsiHKAI
     thaI                            maeII               bmyI   ddeI
     fnuDII/mvnI                     psp1406I            apaLI/snoI rsaI
     apoI                                                alw44I/snoI csp6I
     bstUI   tru9I              tru9I
     bsh1236I mseI       sspI   mseI
2631 AACGCGAATT TAACAAAAT ATTAACGTTT ACAATTTTAT GGTGCACTCT CAGTACAATC
     TTGCGCTTAA AATTGTTTTA TAATTGCAAA TGTTAAAATA CCACGTGAGA GTCATGTTAG hinPI
                                                    bsrI         fnu4HI
                                                    maeIII       nlaIII hhaI/cfoI
             fnu4HI   tru9I                         maeII        bsaAI tth111I/aspI bbvI
             sfaNI aciI    mseI        aciI         CGCTATCGCT ACGTGACTGG GTCATGGCTG CGCCCCGACA
2691 TGCTCTGATG CCGCATAGTT AAGCCAACTC CGCTATCGCT ACGTGACTGG GTCATGGCTG CGCCCCGACA
     ACGAGACTAC GGCGTATCAA TTCGGTTGAG GCGATAGCGA TGCACTGACC CAGTACCGAC GCGGGGCTGT hinPI                                    sfaNI
                     hhaI/cfoI                                mspI
                     thaI                                     hpaII
                     fnuDII/mvnI                              scrFI
                     bstUI                                    nciI
             nspBII bsh1236I                          dsaV fokI            maeIII
     aciI    aciI hgaI       drdI                    cauII     aciI       aluI
2761 CCCGCCAACA CCCGCTGACG CGCCCTGACG GCTTGTCTG CTCCCGGCAT CCGCTTACAG ACAAGCTGTG
     GGGCGGTTGT GGGCGACTGC GCGGGACTGC CCGAACAGAC GAGGGCCGTA GGCGAATGTC TGTTCGACAC
```

FIG._16S

```
                                                                                        thaI
                                                                                        fnuDII/mvnI
                                                                                        bstUI
                                                                                        bsh1236I
                                                                                        hinPI
                                                                                        hhaI/cfoI
                                                    hphI                                thaI mnlI
                                      mnlI         hphI                                 fnuDII/mvnI
         scrFI                                                                          bstUI
         nciI                                                                           bsh1236I
         mspI
         hpaII      nspI
         dsaV       nspHI
    esp3I     fnu4HI
    bsmAI     bbvI
    bslI cauII aluI nlaIII mnlI   hphI     hphI
2831 ACCGTCTCCG GGAGCTGCAT GTGTCAGAGG TTTTCACCGT CATCACCGAA ACGCGCGAGG CAGTATTCTT
     TGGCAGAGGC CCTCGACGTA CACAGTCTCC AAAAGTGGCA GTAGTGGCTT TGCGCGCTCC GTCATAAGAA mnlI
              haeIII/palI                          nlaIII
         mboII sau96I                    tru9I rcaI
         bpuAI asuI                      msel bspHI
         bbsI  eco0109I/draII
2901 GAAGACGAAA GGGCCTCGTG ATACGCCTAT TTTTATAGGT TAATGTCATG
     CTTCTGCTTT CCCGGAGCAC TATGCGGATA AAAATATCCA ATTACAGTAC aciI
                                                          thaI
                                                          fnuDII/mvnI
                                                          bstUI
                                                          bsh1236I
                            hinII/acyI                    hinPI
                            ahaII/bsaHI                   hhaI/cfoI
                            aatII
                      ddeI maeII
2951 ATAATAATGG TTTCTTAGAC GTCAGGTGGC ACTTTTCGGG GAAATGTGCG
     TATTATTACC AAAGAATCTG CAGTCCACCG TGAAAAGCCC CTTTACACGC
```

FIG._16T

```
                                                                bsmAI
                                                         rcaI
                                                  bsrBI  nlaIII
                                                     aciI bspHI
        nlaIV
3001 CGGAACCCCT ATTTGTTTAT TTTTCTAAAT ACATTCAAAT ATGTATCCGC TCATGAGACA ATAACCCTGA
     GCCTTGGGGA TAAACAAATA AAAAGATTTA TGTAAGTTTA TACATAGGCG AGTACTCTGT TATTGGGACT
                              mboII
                    sspI    earI/ksp632I
3071 TAAATGCTTC AATAATATTG AAAAAGGAAG AGTATGAGTA TTCAACATTT CCGTGTCGCC CTTATTCCCT
     ATTTACGAAG TTATTATAAC TTTTCCTTC  TCATACTCAT AAGTTGTAAA GGCACAGCGG GAATAAGGGA fnu4HI                                                             sfaNI
         aciI                                 hphI                hphI
3141 TTTTTGCGGC ATTTGCCTT  CCTGTTTTG  CTCACCCAGA AACGCTGGTG AAAGTAAAAG
     AAAAACGCCG TAAAACGGAA GGACAAAAAC GAGTGGGTCT TTGCGACCAC TTTCATTTTC hgiAI/aspHI
                    bsp1286
                    bsiHKAI                             sau3AI
            sau3AI                                    mboI/ndeII[dam-]
          mboI/ndeII[dam+]                             dpnI[dam+]
           dpnI[dam+]  bmyI                            dpnII[dam-]
           dpnII[dam-]                                  bstYI/xhoII
             mboII[dam-]    apaLI/snoI        taqI       alwI[dam-]  aciI
              eco57I       alw44I/snoI      maeIII      bsrI       nspBII
3201 ATGCTGAAGA TCAGTTGGGT GCACGAGTGG GTTACATCGA ACTGGATCTC AACAGCGGTA
     TACGACTTCT AGTCAACCCA CGTGCTCACC CAATGTAGCT TGACCTAGAG TTGTCGCCAT
```

FIG._16U

```
       sau3AI
       mboI/ndeII[dam-]              maeII
       dpnI[dam+]                    psp1406I                              hgiAI/aspHI
       dpnII[dam-]                   xmnI                                  bsp1286I  tru9I
       alwI[dam-]                    asp700                                bsiHKAI   mseI
       bstYI/xhoII      mboII                                              bmyI      ahaIII/draI
3261 AGATCCTTGA GAGTTTCGC CCCGAAGAAC GTTTTCCAAT GATGAGCACT TTTAAAGTTC
     TCTAGGAACT CTCAAAAGCG GGGCTTCTTG CAAAAGGTTA CTACTCGTGA AAATTTCAAG
                                          scrFI
                         aciI             nciI
                         thaI             mspI
                         fnuDII/mvnI      hpaII
                         bstUI            dsaV
                         bsh1236I         hinlI/acyI
                 hinPI                    hgaI cauII                         aciI
                 hhaI/cfoI                ahaII/bsaHI       bcgI mcrI        fnu4HI
3321 TGCTATGTGG CGCGGTATTA TCCCGTGATG ACGCCGGGCA AGAGCAACTC GGTCGCCGCA
     ACGATACACC GCGCCATAAT AGGGCACTAC TGCGGCCCGT TCTCGTTGAG CCAGCGGCGT
                                  rsaI
                                  csp6I bsrI
                                  scaI  hphI maeIII              sfaNI       fokI
           ddeI
3381 TACACTATTC TCAGAATGAC TTGGTTGAGT ACTCACCAGT CACAGAAAAG CATCTTACGG
     ATGTGATAAG AGTCTTACTG AACCAACTCA TGAGTGGTCA GTGTCTTTTC GTAGAATGCC
```

FIG._16V

```
                                                              haeIII/palI
                                                              eaeI
                                                              cfrI
                                                              fnu4HI
                      fnu4HI                                  aciI
                      bbvI           nlaIII
            nlaIII                   CATGAGTGAT AACACTGCGG CCAACTTACT
3441 ATGGCATGAC AGTAAGAGAA TTATGCAGTG CTGCCATAAC CATGAGTGAT AACACTGCGG CCAACTTACT
     TACCGTACTG TCATTCTCTT AATACGTCAC GACGGTATTG GTACTCACTA TTGTGACGCC GGTTGAATGA sau96I
               avaII                                                     nlaIII
               asuI                                                      sau3AI maeIII
         sau3AI                                                          mboI/ndeII[dam-]
         mboI/ndeII[dam-]                                                dpnI[dam+]
         dpnI[dam+]                                                      dpnII[dam-]
         dpnII[dam-]                                    nlaIII alwI[dam-]
         pvuI/bspCI
         mcrI  mnlI        aluI   aciI
3511 TCTGACAACG ATCGGAGGAC CGAAGGAGCT AACCGCTTTT TTGCACAACA TGGGGGATCA TGTAACTCGC
     AGACTGTTGC TAGCCTCCTG GCTTCCTCGA TTGGCGAAAA AACGTGTTGT ACCCCCTAGT ACATTGAGCG mspI
         sau3AI  nlaIV
         mboI/ndeII[dam-] aluI                                              fnu4HI
         dpnI[dam+]  hpaII                                        maeIII  sfaNI  bbvI
         dpnII[dam-] bsaWI
3581 CTTGATCGTT GGGAACCGGA GCTGAATGAA GCCATACCAA ACGACGAGCG TGACACCACG ATGCCAGCAG
     GAACTAGCAA CCCTTGGCCT CGACTTACTT CGGTATGGTT TGCTGCTCGC ACTGTGGTGC TACGGTCGTC
```

```
                                                 mspI
                                                 hpaII
                        hinPI                    scrFI
                        hhaI/cfoI                nciI
                        mstI                     alul  dsaV
                        aviII/fspI     bsrI      rmaI
              maeII                   tru9I      maeI  cauII
              psp1406I                mseI
3651 CAATGGCAAC AACGTTGCGC AAACTATTAA CTGGCGAACT ACTTACTCTA GCTTCCCGGC
     GTTACCGTTG TTGCAACGCG TTTGATAATT GACCGCTTGA TGAATGAGAT CGAAGGGCCG bglI
                                                           sau96I
                                           sau96I          haeIII/palI
                                           avaII           hinPI  asuI   mspI
      tru9I    fokI           aciI         asuI            hhaI/cfoI     hpaII
      mseI     bsrI                                                      
      aseI/asnI/vspI  mnlI                                               
3711 AACAATTAAT AGACTGGATG CTCCGCCTAT TTCAACGTCC TGGTGAAGAC GCGAGCCGGG AAGGCCGACC
     TTGTTAATTA TCTGACCTAC GAGGCGGATA AAGTTGCAGG ACCACTTCTG CGCTCGGCCC TTCCGGCTGG mspI                    thaI
                                 hpaII                   fnuDII/mvnI
                                 cfr10I                  bstUI
                                 nlaIV hphI     bsmAI aciI           fnu4HI
                       gsuI/bpmI                bsaI bsh1236I        bbvI
3781 CTGGTTTATT GCTGATAAAT CTGGAGCCGG TGAGCGTGGG TCTCGCGGTA TCATTGCAGC
     GACCAAATAA CGACTATTTA GACCTCGGCC ACTCGCACCC AGAGCGCCAT AGTAACGTCG
```

```
     sau96I
      asuI
      nlaIV                                                               pleI
      bsrI haeIII/palI  mnlI                                  eam1105I    hinfI
3841 ACTGGGGCCA GATGGTAAGC CCTCCCGTAT CGTAGTTATC TACACGACGG GGAGTCAGGC
     TGACCCCGGT CTACCATTCG GGAGGGCATA GCATCAATAG ATGTGCTGCC CCTCAGTCCG ddeI
                            sau3AI            nlaIV
                            mboI/ndeII[dam-]
                            dpnI[dam+]        hgiCI         tru9I
             fokI           dpnII[dam-]       banI mnlI     mseI
3901 AACTATGGAT GAACGAAATA GACAGATCGC TGAGATAGGT GCCTCACTGA TTAAGCATTG
     TTGATACCTA CTTGCTTTAT CTGTCTAGCG ACTCTATCCA CGGAGTGACT AATTCGTAAC tru9I
                                                      mseI             tru9I
                                                      ahaIII/draI      mseI
     maeIII                                                   TTCATTTTA
3961 GTAACTGTCA GACCAAGTTT ACTCATATAT ACTTTAGATT GATTAAAAAC AAGTAAAAAT
     CATTGACAGT CTGGTTCAAA TGAGTATATA TGAAATCTAA CTAAATTTTG AAGTAAAAAT
                rmaI      sau3AI
                sau3AI hphI mboI/ndeII[dam-]
                mboI/ndeII[dam-]
                dpnI[dam+]     dpnI[dam+]
                dpnII[dam-]    dpnII[dam-]
     tru9I bstYI/xholI         alwI[dam-]
     mseI  alwI[dam-]          bstYI/xhoII
     ahaIII/draI maeI  mboII[dam-]

nlaIII      maeII
                                                              rcaI        tru9I
                                                              bspHI       mseI
4021 ATTTAAAAGG ATCTAGGTGA AGATCCTTTT TGATAAATCTC ATGACCAAAA TCCCTTAACG TGAGTTTTCG
     TAAATTTTCC TAGATCCACT TCTAGGAAAA ACTATTAGAG TACTGGTTTT AGGGAATTGC ACTCAAAGC
```

FIG._16Y

```
                 hgaI
           ddeI
                                                    sau3AI
                                                    mboI/ndeII[dam-]
                                                    dpnI[dam+]    sau3AI
                                                    dpnII[dam-]   mboI/ndeII[dam-]
                                                    bstYI/xhoII   dpnI[dam+]
                                        sau3AI     alwI[dam-]     dpnII[dam-]
                                        mboI/ndeII[dam-]          alwI[dam-]
                                        dpnI[dam+] mboII[dam-]
                                        dpnII[dam-]               bstYI/xhoII
4091 TTCCACTGAG CGTCAGACCC CGTAGAAAAG ATCAAAGGAT CTTCTTGAGA TCCTTTTTTT
     AAGGTGACTC GCAGTCTGGG GCATCTTTTC TAGTTTCCTA GAAGAACTCT AGGAAAAAAA thaI
     fnuDII/mvnI
     bstUI
     bsh1236I
     hinPI       fnu4HI                                acil
     hhaI/cfoI   bbvI                                  nspBII
4151 CTGCGCGTAA TCTGCTGCTT GCAAACAAAA AAACCACCGC TACCAGCGGT GGTTTGTTTG
     GACGCGCATT AGACGACGAA CGTTTGTTTT TTTGGTGGCG ATGGTCGCCA CCAAACAAAC sau3AI
             mboI/ndeII[dam-]
             dpnI[dam+]
             dpnII[dam-]
             alwI[dam-]
     mspI                                                  hinPI
     hpaII     aluI                      bsrI              hhaI/cfoI
                     maeIII   eco57I                       
4211 CCGGATCAAG AGCTACCAAC TCTTTTTCCG AAGGTAACTG GCTTCAGCAG AGGCAGATA CCAAATACTG
     GGCCTAGTTC TCGATGGTTG AGAAAAAGGC TTCCATTGAC CGAAGTCGTC TCGCGTCTAT GGTTTATGAC
```

FIG._16Z-1

```
             rmaI             haeIII/palI
             maeI       bslI    haeI            scfI       aciI       mnlI
4281   TCCTTCTAGT GTAGCCGTAG TTAGGCCACC ACTTCAAGAA CTCTGTAGCA CCGCCTACAT ACCTCGCTCT
       AGGAAGATCA CATCGGCATC AATCCGGTGG TGAAGTTCTT GAGACATCGT GGCGGATGTA TGAGCGAGA scrFI
                                                            nciI
                                 fnu4HI                     mspI
                                  bbvI                      hpaII
                    alwNI     fnu4HI                        dsaV       pleI
              bsrI  fnu4HI     bbvI   bsrI                  cauII      hinfI
             maeIII  bbvI
4351   GCTAATCCTG TTACCAGTGG CTGCTGCCAG TGGCGATAAG TCGTGTCTTA CCGGGTTGGA CTCAAGACGA
       CGATTAGGAC AATGGTCACC GACGACGGTC ACCGCTATTC AGCACAGAAT GGCCCAACCT GAGTTCTGCT hgiAI/aspHI
                         nspBII                  bsp1286
                         fnu4HI                  bsiHKAI
                  mspI    bbvI mcrI              bmyI
                  hpaII  hinPI aciI              apaLI/snoI
                  bsaWI  hhaI/cfoI               alw44I/snoI  aluI
                 maeIII
4421   TAGTTACCGG ATAAGGCGCA GCGGTCGGGC TGAACGGGGG GTTCGTGCAC ACAGCCCAGC TTGGAGCGAA
       ATCAATGGCC TATTCCGCGT CGCCAGCCCG ACTTGCCCCC CAAGCACGTG TGTCGGGTCG AACCTCGCTT hinPI
                                                            hhaI/cfoI
                    ddeI            scfI                    haeII
4491   CGACCTACAC CGAACTGAGA TACCTACAGC GTGAGCATTG AGAAAGCGCC ACGCTTCCCG AAGGGAGAAA
       GCTGGATGTG GCTTGACTCT ATGGATGTCG CACTCGTAAC TCTTTCGCGG TGCGAAGGGC TTCCCTCTTT
```

FIG._16Z-2

```
                                                                              scrFI
                                                                              mvaI
                                                                              ecoRII   mvaI
                                                                              dsaV     ecoRII
                                                                              bstNI
                                                          hinPI mnlI          bsaJI
                  mspI                                    hhaI/cfoI  aluI apyI[dcm+]
                  hpaII
            bslI        fnu4HI
       aciI bsaWI       aciI
4561  GGCGGACAGG TATCCGGTAA GCGGCAGGGT CGGAACAGGA GAGGCACGA GGGAGCTTCC AGGGGGAAAC
      CCGCCTGTCC ATAGGCCATT CGCCGTCCCA GCCTTGTCCT CTCGCGTGCT CCCTCGAAGG TCCCCCTTTG
       scrFI
                                                                      sfaNI
       dsaV                                    mnlI drdI hgaI  taqI
       bstNI
       apyI[dcm+]
4631  GCCTGGTATC TTTATAGTCC TGTCGGGTTT CGCCACCTCT GACTTGAGCG TCGATTTTTG TGATGCTCGT
      CGGACCATAG AAATATCAGG ACAGCCCAAA GCGGTGGAGA CTGAACTCGC AGCTAAAAAC ACTACGAGCA
                                                haeIII/palI
                                                fnu4HI
                                                aciI
                                                thaI bslI
                                                fnuDII/mvnI
                                                bstUI
            nlaIV                               bsh1236I
            aciI
4701  CAGGGGGGCG GAGCCTATGG AAAAACGCCA GCAACGCGGC
      GTCCCCCCGC CTCGGATACC TTTTTGCGGT CGTTGCGCCG
```

FIG._16Z-3

```
                haeIII/palI
      scrFI
      mvaI bslI
      ecoRII
      dsaV
      bstNI                                                                                      tfiI
      apyI[dcm+]        haeIII/palI    nspI                                                     hinfI
      nlaIV  haeI      haeI           nspI    nspHI
                                              aflIII                              nlaIII
4741 CTTTTTACGG TCCTGGCCT TTTGCTGGCC TTTTGCTCAC ATGTTCTTTC CTGCGTTATC CCCTGATTCT
     GAAAAATGCC AGGACCGGA AAACGACCGG AAACGAGTG TACAAGAAAG GACGCAATAG GGGACTAAGA fnu4HI
                                                                bbvI
                                                      bsrBI    aciI
                                               aluI   aciI    fnu4HI      mcrI
4811 GTGGATAACC GTATTACCGC CTTTGAGTGA GCTGATACCG CTCGCCGCAG CCGAACGACC
     CACCTATTGG CATAATGGCG GAAACTCACT CGACTATGGC GAGCGGCGTC GGCTTGCTGG hinPI
                                                     haeII
     fnu4HI                                          sapI hhaI/cfoI
     bbvI pleI                                       mboII                                mnlI
     hinPI hinfI                           mnlI aciI          earI/ksp632I         aciI
     hhaI/cfoI
4871 GAGCGCAGCG AGTCAGTGAG CGAGGAAGCG CGAGGAAGCG GAAGAGCGCC CAATACGCAA ACCGCCTCTC
     CTCGCGTCGC TCAGTCACTC GCTCCTTCGC CTTCTCGCGG GTTATGCGTT TGGCGGAGAG
```

FIG._16Z-4

```
            thaI
            fnuDII/mvnI
            bstUI
            bsh1236I
            hinPI
            hhaI/cfoI
            thaI
            fnuDII/mvnI
            bstUI
            bsh1236I haeIII/palI        truI9I   aluI
       bslI   eaeI  tfiI asel/asnI/vspI          pvuII                          bsrI      aciI
       aciI   cfrI  hinfI  mseI  nspBII                                                        
4931 CCCGGCGGTT GGCCGATTCA TTAATCCAGC TGGCACGACA GGTTTCCCGA CTGGAAAGCG
     GGGCCGCCAA CCGGCTAAGT AATTAGGTCG ACCGTGCTGT CCAAAGGGCT GACCTTTCGC scrFI
                                                                                         mvaI
                                                                                         ecoRII
                                                                                         dsaV
                                                                               nlaIV     bstNI
                                                                               hgiCI     apyI[dcm+]
                              tru9I                                            banI      bsaJI
                              mseI        maeIII              mnlI
                 hinPI  hhaI/cfoI  aseI/asnI/vspI
4991 GGCAGTGAGC GCAACGCAAT TAATGTGAGT TACCTCACTC ATTAGGCACC CCAGGCTTTA CACTTTATGC
     CCGTCACTCG CGTTGCGTTA ATTACACTCA ATGGAGTGAG TAATCCGTGG GGTCCGAAAT GTGAAATACG
```

FIG._16Z-5

```
          mspI                         aciI                    aluI      nlaIII
            hpaII              bsrBI                                        
5061 TTCCGGCTCG TATGTTGTGT GGAATTGTGA GCGGATAACA ATTTCACACA GGAAACAGCT ATGACCATGA
     AAGGCCGAGC ATACAACACA CCTTAACACT CGCCTATTGT TAAAGTGTGT CCTTTGTCGA TACTGGTACT tru9I
            mseI
             aseI/asnI/vspI
              xmnI
               asp700
5131 TTACGAATTA A
     AATGCTTAAT T >length: 5141
```

KINASE RECEPTOR ACTIVATION ASSAY

CROSS REFERENCES

This application is a continuation of co-pending U.S. application Ser. No. 08/286,305 filed Aug. 5, 1994, which application is a continuation-in-part of co-pending U.S. application Ser. No. 08/170,558 filed Dec. 20, 1993, which application is a continuation of U.S. application Ser. No. 08/157,563 filed Nov. 23, 1993 (abandoned), which applications are incorporated herein by reference and to which applications priority is claimed under 35 USC § 120.

BACKGROUND OF THE INVENTION

1. Field of the Invention

This invention relates to a kinase receptor activation (KIRA) assay. In particular, the invention relates to an assay for measuring autophosphorylation of the kinase domain of a receptor protein tyrosine kinase (rPTK) using a kinase receptor activation, enzyme-linked immunosorbent assay (KIRA ELISA).

2. Description of Related Art

One mechanism for signal transduction in animals involves protein phosphorylation. Protein phosphorylation involves the action of protein kinase, an enzyme that transfers a phosphate group from a phosphate donor onto an acceptor amino acid in a substrate protein. Protein phosphatases provide a means for reversing the signal when the stimulus is removed.

Protein kinases have multiple substrates, and classification of the protein kinases is based on the acceptor amino acid specificity. The two most well characterized protein kinases are the protein kinases with a protein alcohol group as acceptor called protein serine/threonine kinases and the protein kinases with a protein phenolic group as acceptor called protein tyrosine kinases (Hunter, *Methods in Enzymology* 200:3–9[1991]).

The most well known type of signal-transducing protein kinases are growth factor receptor protein tyrosine kinases (rPTKs). rPTKs usually comprise a large, glycosylated, extracellular ligand binding domain (ECD) and an intracellular domain (ICD) which contains a tyrosine kinase catalytic domain. A single hydrophobic transmembrane (TM) domain connects the ECD and ICD. Examples of rPTKs include the insulin receptor, epidermal growth factor receptor (EGF-R), platelet-derived growth factor receptor (PDGF-R), insulin-like growth factor 1 receptor (IGF-1-R), and the HER2 receptor, to name a few. See, for example, Ullrich and Schlessinger *Cell* 61:203–212 (1990) and Fantl et al., *Annu. Rev. Biochem.* 62:453–481 (1993). rPTKs can phosphorylate exogenous protein substrates and intrinsic tyrosine residues via their catalytic tyrosine kinase domain. The intrinsic tyrosine residues normally reside in the ICD of the rPTK (see FIG. 1 herein). Activation of the intracellular kinase domain of rPTKs appears to be mediated by receptor oligomerization which results from the conformational alteration of the ECD upon ligand binding thereto. See Ullrich and Schlessinger, supra.

Various assays have been developed which measure tyrosine kinase activity. Some of these assays measure the ability of a tyrosine kinase enzyme to phosphorylate a synthetic substrate polypeptide. For example, an assay has been developed which measures growth factor-stimulated tyrosine kinase activity by measuring the ability of the kinase to catalyze the transfer of the γ-phosphate of ATP to a suitable acceptor substrate. See Pike, L., *Methods of Enzymology* 146:353–362 (1987) and Hunter, *Journal of Biological Chemistry* 257(9):4843–4848 (1982), for example. In this assay, the use of [γ-$^{32}$P]ATP permits the radioactive labeling of the phosphorylated substrate, which is a synthetic tyrosine-containing peptide. Others have described protein kinase assays wherein incorporation of $^{32}$P into a tyrosine kinase receptor, such as the EGF receptor (see Donato et al., *Cell Growth Differ.* 3:259–268 [1992]), insulin receptor (see Kasuga etal, *Journal of Biological Chemistry* 257(17):9891–9884[1982] and Kasuga et al., *Methods in Enzymology* 109:609–621 [1985]), and liver growth hormone receptor (see Wang et al., *Journal of Biological Chemistry* 267(24):17390–17396[1992]), is measured.

The discovery of anti-phosphotyrosine antibodies has provided a non-radioactive, alternative means for measuring phosphorylation of tyrosine residues. For example, White and Backer (*Methods in Enzymology* 201:65–67 [1991]) mention polyclonal antibodies which selectively bind to phosphotyrosine and are considered to be useful for studying rPTKs. An anti-phosphotyrosine monoclonal antibody was used in one of the assays referred to in Madden et al (*Anal Biochem* 199:210–215 [1991]), which measured phosphatase activity toward the insulin receptor. Anti-phosphotyrosine antibodies were also used by Cleaveland et al., in their protein tyrosine kinase ELISA assay. See Cleaveland et al., *Analytical Biochemistry* 190:249–253 (1990). The method of Cleaveland et al., utilizes purified high-activity oncogene tyrosine kinases, v-src and v-fps, and measures the ability of these tyrosine kinases to phosphorylate synthetic polymeric substrates which are coated on an ELISA microtiter plate. The phosphotyrosine produced by src-induced phosphorylation of the polymeric substrate is then quantitated by addition of an anti-phosphotyrosine antibody, the presence of which is detected using a second rabbit anti-mouse antibody which is linked to a reporter enzyme, horseradish peroxidase (HRPO). A similar ELISA assay has been developed by Lazaro et al., which is used for detection of a protein tyrosine kinase. See Lazaro et al., *Analytical Biochemistry* 192:257–261 (1991). Like the assay of Cleaveland et al., this assay also measures the ability of a protein tyrosine kinase to phosphorylate a synthetic substrate which is bound to microELISA wells.

A direct way to assess specific activation of rPTKs is by analysis of receptor autophosphorylation. See, e.g., Hunter and Cooper *Ann Rev Biochem* 54:897–930 (1985) and Ullrich and Schlessinger, *Cell* 61:203–212 (1990). Using this direct approach, Knutson and Buck disclose assays for measuring autophosphorylation of the insulin receptor under in situ or in vitro conditions (*Archives of Biochemistry and Biophysics* 285(2):197–204 [1991]). In the in situ assay, monolayer cultures of embryonic mouse 3T3-C2 fibroblasts (having the endogenous insulin receptor) are incubated with insulin in large cell culture dishes. Following incubation, the insulin receptor is extracted from the membranes. To achieve extraction of the insulin receptor, the cell monolayers are scraped into a buffer containing protease inhibitors and the cells are then disrupted in a homogenizer. The cellular homogenate is subsequently subjected to centrifugation for 60 min., and the pellet which forms is extracted into buffer containing detergent. Following a further centrifugation step, the supernatant (containing the insulin receptor) is incubated with an anti-insulin receptor antibody. Then, the receptor-antibody complex is incubated with protein A-agarose and unoccupied protein A sites are blocked with normal rabbit IgG. The agarose beads are then centrifuged, the supernatants aspirated and the pellets are re-suspended in buffer containing the radiolabelled antiphosphotyrosine antibody, The amount of bound iodinated anti-phosphotyrosine antibody is consequently measured.

Klein and his colleagues discuss an assay for measuring insulin activation of the insulin receptor (Klein etal., *Diabetes* 42:883–890 [1993]). In this assay, aliquots of a heterogeneous population of mononuclear blood cells (including T cells, B cells, macrophages etc) having the insulin receptor are exposed to insulin in centrifuge tubes. The cells are then lysed in detergent using a motordriven homogenizer and the lysates are concentrated two-to four-fold using vacuum centrifugation. Sometimes, the insulin receptor is also partially purified using wheat germ agglutin agarose. The supernatants which form following centrifugation, are then transferred to anti-insulin receptor-coated microtiter plates. Insulin (8.7nM) as well as kinase and phosphatase inhibitors are present during receptor immobilization in order to optimize the percentage of receptors captured to the microtiter plates. Activation of the insulin receptor is then measured by transphosphorylation of the substrate Poly-Glu,Tyr with $^{32}$P labeled ATP. The supernatants are then spotted onto absorbent paper and the paper is washed with cold TCA to remove unbound $^{32}$P-ATP. Remaining $^{32}$P-labeled Poly-Glu,Tyr on the washed absorbent paper is subsequently counted by scintillation counting.

Hagino et al. were also interested in studying the insulin receptor in patients (Hagino et al, *Diabetes* 43:274–280 [1994]). As a first step in the assay, Hagino et al. stimulate a primary cell suspension, which is not particularly homogeneous with respect to cell type. In particular, heparinized blood (1ml washed twice with medium and resuspended in 1 ml of medium containing bovine serum albumin, BSA) is exposed to varying concentrations of insulin. The autophosphorylation reaction is stopped, the cells centrifuged for 30 min, the supernatant is discarded and the erythrocyte ghosts thus obtained are resuspended in buffer and centrifuged again. The pellet thereby obtained is adjusted to 500 $\mu$l and solubilized in detergent. The solubilized materials are then centrifuged and the resulting supernatant is subjected to sandwich ELISA (using anti-insulin receptor antibodies to capture the insulin receptor) to determine the extent of insulin receptor autophosphorylation.

Several others have used an enzyme-conjugated form of the anti-phosphotyrosine antibody in Western blot analyses which measure receptor autophosphorylation. Briefly, Western blotting generally involves electrophoresing activated rPTK on polyacrylamide gel. The rPTK is then transferred to nitrocellulose and immunoblotted with the anti-phosphotyrosine antibody which is labelled to enable detection. See, for example, Wang, *Molecular and Cellular Biology* 5(12):3640–3643 (1985); Glenney et al., *Journal of Immunological Methods* 109:277–285 (1988); Kamps, *Methods in Enzymology* 201:101–110 (1991); Kozma et al., *Methods in Enzymology* 201:28–43 (1991); Holmes et al., *Science* 256:1205–10 (1992); and Corfas et al., *PNAS, USA* 90:1624–1628 (1993). However, with Western blot analysis, accurate quantitation can be very tedious. Furthermore, this technique tends to be time-consuming and generally does not allow high sample throughput.

It is an object of the instant invention to provide a sensitive, reliable assay that measures receptor protein tyrosine kinase (rPTK) autophosphorylation. The assay is desirably useful for qualitatively and quantitatively measuring kinase activation as well as facilitating identification and characterization of potential agonists and antagonists for a selected rPTK. It is a further object of the invention to provide an assay which enables ligand-receptor interactions to be studied for any selected rPTK.

This assay must have a capacity for high throughput, that is, the ability to reliably evaluate large numbers of samples in a relatively short period of time (e.g., in one day). The assay ideally does not use radioactive materials and is also amenable to automation.

It is a further object, in at least one embodiment of the invention, to provide a generic assay which enables a rPTK of interest to be studied, regardless of whether or not a receptor-specific capture agent having the desired characteristics is available. Furthermore, it is an object of the invention to provide an assay which substantially represents the activity of the tyrosine kinase receptor in situ. This is desirable insofar as it reduces the possibility that altered interactions between the receptor and the ligand may occur as a consequence of the receptor not being membrane-bound. Furthermore, if the receptor is a multimeric complex, this assay enables the correctly assembled receptor to be studied.

These and other objects will be apparent to the ordinary artisan upon consideration of the specification as a whole.

SUMMARY OF THE INVENTION

Accordingly, the invention provides an assay for measuring activation (i.e., autophosphorylation) of a tyrosine kinase receptor of interest.

The assay can be divided into two major stages, each of which is generally performed in separate assay plates. The first stage of the assay involves activating the receptor and is termed the kinase receptor activation (KIRA) stage of the assay. The second stage of the assay involves measuring receptor activation. Conveniently, this is achieved using an enzyme-linked immunosorbent assay (ELISA) to measure receptor activation.

The KIRA stage of the assay involves activating a tyrosine kinase receptor which is located in the cell membrane of an eukaryotic cell such that the extracellular domain of the receptor faces the external milieu of the cell, the transmembrane domain is located in the cell membrane and the kinase domain is located intracellularly. This stage of the overall assay involves steps (a) to (c) below:

(a) The first solid phase (e.g., a well of a first assay plate) is coated with a substantially homogeneous population of cells (usually a mammalian cell line) so that the cells adhere to the solid phase. Often, the cells are adherent and thereby adhere naturally to the first solid phase. In one embodiment of the invention, the cells have an endogenous tyrosine kinase receptor presented in the cell membrane as discussed above. In an alternative embodiment, the cells have been transformed with DNA encoding a tyrosine kinase receptor or a "receptor construct" defined further below, which DNA is expressed by the cells such that the receptor or receptor construct is suitably positioned in the cell membranes thereof.

The receptor construct comprises a fusion of a kinase receptor and a flag polypeptide. The flag polypeptide is recognized by the capture agent, often a capture antibody, in the ELISA part of the assay. Use of a receptor construct as disclosed herein is particularly advantageous since it provides a "generic" assay wherein autophosphorylation of any tyrosine kinase receptor can be measured, regardless of whether or not a receptor-specific capture agent having the required characteristics is available. Often, the tyrosine kinase receptor is a fusion protein comprising the ECD of a selected tyrosine kinase and the catalytic ICD (and possibly the transmembrane domain) of another well characterized tyrosine kinase (e.g., the Rse receptor).

(b) An analyte is then added to the wells having the adhering cells, such that the tyrosine kinase receptor is exposed to (or contacted with) the analyte. This assay enables identification of agonist and antagonist ligands for the tyrosine kinase receptor of interest. In order to detect the presence of an antagonist ligand which blocks binding and/or activation of the receptor by an agonist ligand, the adhering cells are exposed to the suspected antagonist ligand first and then to the agonist ligand (or to a mixture of the agonist and antagonist) so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands.

(c) Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. Thus, this assay provides a significant improvement over assays described by Knutson and Buck, supra, Klein et al., supra, and Hagino et al., supra, insofar as it is surprisingly unnecessary to concentrate the cell lysate prior to the ELISA. Furthermore, unlike the other assays, in the instant assay the cells can be lysed in lysis buffer using gentle agitation without the need for homogenizing, centrifuging or clarifying the cells. The cell lysate thus prepared is then ready to be subjected to the ELISA stage of the assay. It has been discovered that, surprisingly, the first assay plate can be stored at freezing temperatures (i.e., at about −20 to −70° C.) for significant periods of time (at least 6 months) before the ELISA stage of the assay. This is a significant finding insofar as the KIRA and ELISA stages of the assay can be performed on separate days.

The ELISA component of the assay comprises steps (d) to (h), described below.

(d) As a first step, the second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used.

(e) The cell lysate obtained in step (c) of the above-mentioned KIRA stage of the assay is exposed to, or contacted with, the adhering capture agent so that the receptor or receptor construct adheres to (or is captured in) the second solid phase. Unlike the assay of Klein et al., the instant assay does not require the ligand for the receptor as well as kinase inhibitors to be present to achieve suitable immobilization of the receptor or receptor construct to the second solid phase.

(f) A washing step is then carried out, so as to remove unbound cell lysate, leaving the captured receptor or receptor construct.

(g) The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule.

(h) Finally, binding of the anti-phosphotyrosine antibody to the captured receptor or receptor construct is measured, e.g., by a color change in the color reagent.

The invention also pertains to a Rse.flag reagent which is particularly useful for use in the KIRA ELISA assay. The Rse.flag reagent is a polypeptide comprising a fusion of a flag polypeptide (usually the gD flag described herein) to the carboxyl terminus of the intracellular domain of the Rse rPTK. Generally, the transmembrane domain of Rse and the extracellular domain of another rPTK of interest are also present in the fusion polypeptide reagent. The nucleic acid encoding this reagent and a cell transformed therewith are also claimed.

In yet a further aspect, the invention relates to a kit which can be used in the KIRA ELISA disclosed above which comprises an anti-flag polypeptide capture agent (e.g. a capture antibody) which is usually bound to the second solid phase as described herein. Thus, the kit generally provides an ELISA microtiter plate having an anti-flag polypeptide capture anti-body adhering to a well thereof. Optionally, the kit also provides an anti-phosphotyrosine antibody which is often labelled, or reagents for labelling the anti-phosphotyrosine antibody are supplied with the kit. Sometimes, a homogeneous population of cells which have been transformed with a receptor construct as described herein are also provided with the kit. The kit also suitably includes instructions for carrying out the KIRA ELISA.

BRIEF DESCRIPTION OF THE DRAWINGS

FIGS. 1A–1C are diagrammatic representations of Rse.gD (FIG. 1A), Receptor ECD/Rse.gD chimera (FIG. 1B) and a CHO cell transformed with the Receptor ECD/IRse.gD chimera (FIG. 1C).

FIGS. 2A–2C depict an alignment of the amino acid sequence (SEQ ID NO: 1) and nucleotide sequence (SEQ ID NO: 2) of Rse.gD. The residues of the signal sequence are indicated with an (*), the transmembrane domain of Rse is boxed and the ECD and ICD of Rse are also delineated. The residues of the gD flag sequence are underlined.

FIG. 3 is a flow diagram of an exemplary strategy for selecting a suitable capture agent for use in the assay.

FIG. 4 is a flow diagram of an exemplary strategy for selecting a transformed cell suitable for use in the assay, where the cell has a receptor construct with an amino-terminal flag polypeptide located in the cell membrane thereof.

FIG. 5 is a flow diagram of an exemplary strategy for selecting a transformed cell suitable for use in the assay, where the cell has a receptor construct with a carboxyl-terminal flag polypeptide located in the cell membrane thereof.

FIGS. 6A–6B is a flow chart and cartoon illustrating the KIRA ELISA assay for the HER2 receptor described in Example 1.

FIG. 7 depicts a p185$^{HER2}$/HRGβ1$_{177-244}$ KIRA ELISA standard curve obtained using the assay described in Example 1. To obtain the standard curve, MCF-7 cells (2×10⁵) were stimulated with 3000, 1000, 333, 111, 37, 12, 4, or 0 pM HRGβ1$_{177-244}$, as determined by quantitative amino acid analysis (q.a.a.a.). Each calibrator concentration was run in triplicate. The values derived from 10 such standard curves were averaged (total n=30) and are presented as mean ABS$_{450/650}$±sd vs. HRGβ1$_{177-244}$ concentration.

FIG. 8 depicts heregulin specificity of p185$^{HER2}$/HRG KIRA ELISA of Example 1. In the assay, MCF-7 cells (2×10⁵) were stimulated with either HRGβ1$_{177-244}$ (■) at 3000, 1000, 333, 333, 111, 37, 12, 4 or 0 pM or IGF-1(▲) EGF (□), VEGF (●) or insulin (♦) at 30000, 10000, 3333, 1111, 370, 120, 40 or 0 pM. For all concentrations of ligands, n=3 and data are presented as average ABS$_{450/650}$±sd vs. ligand concentration.

FIGS. 9A–9B is a flow chart and cartoon illustrating the KIRA ELISA assay for the Rse receptor described in Example 2.

FIG. 10 depicts a Rse KIRA ELISA standard curve obtained using the assay described in Example 2. To obtain the standard curve, CHO cells transformed with the Rse.gD construct were stimulated with 1:100, 1:200, 1:400, 1:800, 1:1600, 1:3200 or 0 diluted, anti-Rse agonist antibody. Each calibrator concentration was run in triplicate. The values are presented as mean ABS$_{450/650}$± sd vs. 1/dilution agonist antibody.

FIGS. 11A–11B is a flow chart and cartoon illustrating the KIRA ELISA assay for the trk receptors (i.e., trk A, trk B, and trk C) described in Example 3.

FIGS. 12A–12C depict an alignment of the amino acid acid sequence (SEQ ID NO: 3) and nucleotide sequence (SEQ ID NO: 4) of gD.trk A used in the assay described in Example 3. The residues of the signal sequence are indicated with an (*), the residues of the gD flag sequence are underlined, the residues of the transmembrane domain of trk A are in bold and the ECD and ICD thereof are also delineated.

FIGS. 13A–13C depict an alignment of the amino acid sequence (SEQ ID NO: 5) and nucleotide sequence (SEQ ID NO: 6) of gD.trk B used in the assay described in Example 3. The residues of the signal sequence are indicated with an (*), the residues of the gD flag sequence are underlined, the residues of the transmembrane domain of trk B are in bold and the ECD and ICD thereof are also delineated.

FIGS. 14A–14C depict an alignment of the amino acid sequence (SEQ ID NO: 7) and nucleotide sequence (SEQ ID NO: 8) of gD.trk C used in the assay described in Example 3. The residues of the signal sequence are indicated with an (* ), the residues of the gD flag sequence are underlined, the residues of the transmembrane domain of trk C are in bold and the ECD and ICD thereof are also delineated.

FIGS. 15A–15C depict standard curves for trk A, B and C, respectively, which were obtained using the assay described in Example 3. To obtain the standard curves, CHO cells transformed with the gD.trk constructs were stimulated with 3000, 1000, 333, 111, 37, 12, 4 or 0 pM of ligand, i.e. nerve growth factor (NGF, ■), neurotrophin 3(NT3, ●) or neurotrophin 5(NT5, ▲). The values are presented as mean ABS$_{450/650}$±sd vs. ligand concentration.

FIGS. 16A–16Z-5 depict the nucleotide sequence (SEQ ID NO: 9) of the pSVI17.ID.LL expression vector used for expression of Rse.gD in Example 2.

DETAILED DESCRIPTION OF THE PREFERRED EMBODIMENTS

I. Abbreviations and Definitions

"rPTK" means a receptor protein tyrosine kinase.

"ECD", "TM domain" and "ICD" refer to the extracellular domain, transmembrane domain and intracellular domain of a rPTK, respectively.

"Kinase Receptor Activation" or "KIRA" when used throughout this application refers to the first stage of the instantly claimed assay wherein a cell-bound rPTK is exposed to a potential agonist/antagonist ligand which may (or may not) induce phosphorylation of tyrosine residues in the intracellular domain of the rPTK. The KIRA is generally carried out in the "first assay plate" as defined herein.

"Enzyme-Linked Immunosorbent Assay" or "ELISA" refers to the second stage of the instantly claimed assay and involves measuring tyrosine phosphorylation of the rPTK. The ELISA is normally carried out in the "second assay plate" as disclosed in this application. The ELISA is a "sandwich ELISA" insofar as it involves capturing the rPTK or receptor construct to the second solid phase (usually the well of an ELISA microtiter plate). ELISA assays generally involve the preparation of enzyme-antibody conjugates. The conjugated enzyme cleaves a substrate to generate a colored reaction product that can be detected spectrophotometrically. In this assay, the absorbance of the colored solution in individual microtiter wells is proportional to the amount of phosphotyrosines. A review of ELISA is found in *Current Protocols in Molecular Biology*, Vol. 2, chapter 11 (1991). While the term "ELISA"is used to describe the second stage of the instant assay, it is only a preferred embodiment of the invention, since, as disclosed herein, techniques other than enzymatic detection are available for measuring binding of the anti-phosphotyrosine antibody to the activated receptor.

The terms "receptor", "kinase receptor", "tyrosine kinase", "tyrosine kinase receptor", "receptor protein tyrosine kinase" and "rPTK" are used interchangeably herein and refer to a protein having at least one phosphate accepting phenolic group. The protein is usually a receptor insofar as it has a ligand-binding ECD, TM domain and ICD. The ICD usually comprises a catalytic kinase domain and has one or more phosphate accepting tyrosine residues. See FIGS. 1A and 1B, for example. Examples of tyrosine kinase receptors include the insulin receptor, insulin related receptor, epidermal growth factor receptor (EGF-R), platelet-derived growth factor receptors A and B (PDGF-R-A and PDGF-R-B), insulin-like growth factor 1 receptor (IGF-1-R), macrophage colony-stimulating factor receptor (M-CSF-R), HER2/neulc-erbB-2 receptor, HER3/c-erbB-3 receptor, Xmrk receptor, IRR receptor, fibroblast growth factor (FGF) receptors bek and fig, c-kit receptor, Flk/kDR receptor, Rse receptor, the Eph, Elk, Eck, Eek, Erk, Cek4/Mek4/HEK and Cek5 receptors, Axl receptor, hepatocyte growth factor receptor (HGF-R), Flt1 VEGF receptor, SAL-S1 receptor, HpTK 5 receptor, trkA receptor, trkB receptor, and trkC receptor. See, for example, Ullrich and Schlessinger *Cell* 81:203–212 (1990); Fantl et al., *Annu. Rev. Biochem.* 62:453–481 (1993); Mark et al., *Journal of Biological Chemistry* 269(14):10720–10728 (1994); and WO 93/15201.

The terms mentioned above encompass chimeric "receptor" molecules which comprise at least the extracellular domain of a selected tyrosine kinase and the intracellular domain, and, optionally, the transmembrane domain of another tyrosine kinase. Of course, the tyrosine kinase of interest can provide the transmembrane domain and/or intracellular domain. The terms also encompass amino acid sequence variants and covalent derivatives of the various rPTKs provided they still display tyrosine kinase phosphorylation activity in the KIRA ELISA. Therefore, the variants will general have conservative amino acid alterations. The individual domains of the tyrosine kinase can be delineated based on sequence homology to known tyrosine kinases and hydrophobicity plots. For example, the hydrophobic transmembrane domain can be readily determined and the ECD and ICD are usually amino-terminal and carboxyl terminal to the transmembrane domain, respectively. Conveniently, the transmembrane domain and ICD of the Rse receptor can be fused to the ECD of a tyrosine kinase of interest, thereby forming a chimeric receptor which is encompassed by the terms denoting a receptor as mentioned above.

In the preferred embodiment, the rPTK is selected from the group consisting of HER2 receptor (Ullrich and Schlessinger, supra), Rse receptor (Mark et al., supre and SEQ ID NO: 1), trk A receptor (SEQ ID NO: 3), trk B receptor (SEQ ID NO: 5) and trk C receptor (SEQ ID NO: 7).

By "autophosphorylation" is meant activation of the catalytic kinase domain of the rPTK, whereby at least one intrinsic tyrosine residue is phosphorylated. Generally, autophosphorylation will result when an agonist molecule binds to the extracellular domain of the kinase receptor. Without being limited to any particular mechanism of action, it is thought that binding of the agonist molecule may result in oligomerization of the kinase receptor which causes activation of the catalytic kinase domain.

By "solid phase" is meant a non-aqueous matrix to which the cells (in the KIRA stage of the assay) or the capture agent (in the ELISA stage of the assay) can adhere. Usually, the solid phase comprises the well of an assay plate but the invention is by no means limited to this embodiment. For example, the solid phase can comprise a discontinuous solid phase of discrete particles. The particles can be porous and formed from a number of different materials, e.g., polysaccharides (e.g. agarose), polyacrylamides, polystyrene, polyvinylalcohol, silicones and glasses. For examples of suitable particulate solid phases, see U.S. Pat. No. 4,275, 149.

By "well" is meant a recess or holding space in which an aqueous sample can be placed. The well is provided in an "assay plate". The invention usually employs a "first assay plate" which is formed from a material (e.g. polystyrene) which optimizes adherence of cells (having the receptor or receptor construct) thereto. Generally, the individual wells of the first assay plate will have a high surface area to volume ratio and therefore a suitable shape is a flat bottom well (where the cells are adherent). The "second assay plate" is generally formed from a material (e.g. polystyrene) which optimizes adherence of the capture agent thereto. The second assay plate may have the same general construction and/or characteristics as the first assay plate. However, separate plates are used for the KIRA stage of the assay and the ELISA stage of the assay.

In the preferred embodiment of the invention, both the first assay plate and the second assay plate are "microtiter" plates. The term "microtiter" plate when used herein refers to an assay plate having between about 30 to 200 individual wells, usually 96 wells. Often, the individual wells of the microtiter plate will hold a maximum volume of about 250μl. Conveniently, the first assay plate is a 96 well polystyrene or plastic, cell culture microtiter plate (such as that sold by Becton Dickinson Labware, Lincoln Park, N.J.), which allows for automation. Often, about 50 μl to 300 μl, more preferably 100 μto 200 μl, of an aqueous sample comprising cell culture media with the cells suspended therein will be added to each well of the first assay plate in the KIRA stage of the assay. It is desirable to seed between about $1=10^4$ to $3=10^5$ cells per well. More preferably, $5 =10^5$ cells per well are seeded. Usually, the second assay plate will comprise a polystyrene microtiter ELISA plate such as that sold by Nunc Maxisorp, Inter Med, Denmark.

The term "homogeneous population of cells" refers to a substantially homogeneous population of cells wherein at least about 80%, and preferably about 90%, of the cells in the population are of the same cell type. Therefore, it is convenient to use a cell line. The cell line is a eukaryotic cell line, normally an animal cell line and desirably a mammalian cell line.

The cells have, or are transformed to produce, the selected receptor or a receptor construct. For example, where the kinase receptor is known to be present in a certain cell line (e.g., the HER2 receptor in the MCF-7 cell line) no transformation step is required. Conversely, it may be necessary to transform a cell with a nucleic acid encoding the receptor, where the cell does not make the receptor, or does not have suitable numbers of the receptor in the cell membrane thereof. Accordingly, the cell is transformed with a nucleic acid encoding the receptor (or receptor construct) and the nucleic acid is expressed so that the ECD of the receptor faces the external milieu of the cell, the transmembrane domain is located in the cell membrane and the kinase domain is located intracellularly.

Where the assay relies on activating the endogenous rPTK, a cell line is selected which is known to produce the rPTK of interest, provided sufficient levels of the rPTK are present in the cell membrane thereof to enable detection. As a general proposition, a minimum number of about $1=10_4$ receptors/cell is required. For example, the MCF-7 cell line (ATCC-HTB 22) which produces the HER2 receptor was shown to be useful in the assay. There are $5 \times 10^4$ HER2 receptors/MCF-7 cell. Examples of other cell lines and their respective rPTKs include, embryonic mouse 3T3-C2 fibroblast cell line and the insulin receptor, and Hep 3B (ATCC#HB 8064) cell line and the Rse receptor. However, the degree of expression of the rPTK nucleic acid in the cell line is not so high that it results in constitutive phosphorylation of the rPTK. For example, the SK-BR-3 cell line (ATCC HTB30), which has $3=10^6$ HER2 receptors/cell, was found to be unsuitable for use in the assay disclosed herein. Therefore, it may be useful to use a cell line which has less than about $3=10^6$ receptors/cell, depending on the type of receptor. The number of receptors/cell can be measured using Scatchard analysis, for example (Scatchard, *Ann. NY Acad. Sci.* 51:660–672 [1949]; and Goodwin et at., *Cell* 73:447–456 [1993]). However, selection of a cell line having a suitable number of receptors/cell is possible using the techniques described herein.

The term "adherent" when used herein to describe the cell, refers to a cell which naturally adheres to the first solid phase (often the well of the first assay plate), thereby forming a fairly uniform coating of the cells on the inside surface of the well. The uniform coating of cells generally forms following incubation of the cells in the wells of the first assay plate for about 8–16 hours. After incubation, non-adhering cells and cell culture medium are decanted off the first assay plate. Incubation is usually carried out at a temperature which is optimal for cell growth, i.e. about 37° C. Examples of adherent cell lines include CHO cells (Urlaub and Chasin, *Proc. Natl. Acad. Sci. USA* 77:4216 [1980]), MCF-7 cells (ATCC HB 22), 293 cells (Graham et al., *J. Gen Virol.* 36:59 [1977]). Swiss albino 3T3 fibroblast cell line (ATCC No. CCL 92) and U937 macrophage cell line (ATCC No. CRL 1593).

A "flag polypeptide" comprises a short polypeptide which has enough residues to provide an epitope (preferably a linear epitope) against which a "capture agent" thereagainst can be made, yet is short enough such that it does not interfere with activity of the rPTK. The flag polypeptide is also sufficiently unique so that the capture agent thereagainst does not bind to other reagents in the assay. Selection of a "unique" flag polypeptide sequence can be accomplished by comparing the sequence of a proposed flag polypeptide against other known sequences in Genbank or EMBL, for example. Suitable flag polypeptides generally have at least 6 amino acid residues and usually between about 8–80 amino acid residues (preferably between about 9–30 amino acid residues).

By "receptor construct" is meant a polypeptide which comprises a fusion of a kinase receptor and a flag polypeptide as defined above. The flag polypeptide is provided at a location in the receptor construct such that: a) the flag polypeptide does not interfere with ligand binding to the receptor; b) the flag polypeptide does not interfere with autophosphorylation of the receptor and c) the flag polypeptide is presented in a suitable configuration so that it can bind to the capture agent in the ELISA stage of the assay. Often, the polypeptide flag will be present at the N-terminus of the receptor construct. See, for example, Example 3 which refers to the gD.trk constructs. Alternatively, the flag polypeptide may be present at the C-terminus of the receptor construct. See, for example, Example 2 which refers to the Rse.gD construct. See also FIGS. 1A–1C. The Rse construct disclosed herein is particularly useful, since the ICD (and optionally the transmembrane domain) thereof can be fused to the ECD of a kinase receptor of interest, thereby obviating the need to establish where the flag polypeptide should be located with respect to the kinase receptor of interest.

"Rse.gD" refers to a receptor construct which is the Rse receptor protein tyrosine kinase with the Herpes Simplex virus glycoprotein D (gD) flag polypeptide fused to the COOH-terminus thereof.

"Rse.flag reagent" refers to a polypeptide which comprises the ICD of the Rse receptor fused at its COOH-terminus to a flag polypeptide (normally the gD flag polypeptide). Sometimes, the TM domain of Rse and the ECD of a rPTK of interest will also be present in the Rse.gD. reagent. "Receptor ECD/Rse.gD Chimera" refers to a fusion of the ECD of a rPTK of interest to the TM and ICD domains of Rse which are fused COOH-terminally to the gD flag polypeptide.

"gD.trkA", "gD.trkB" and "gD.trkC" refer to each of the trk receptors (A–C) having the gD flag polypeptide fused to the amino-termini thereof.

By "capture agent" is meant a compound or agent which is able to adhere to the second solid phase, as herein defined, and which is selective for a rPTK or receptor construct. Thus, the capture agent captures the receptor or receptor construct to the wells of the second assay plate. Usually, the capture agent binds selectively to the flag polypeptide which has been fused to the receptor of interest. Binding of the capture agent is not affected by the presence or absence of ligand bound to the receptor and does not induce receptor activation upon capture. Furthermore, the capture agent does not sterically block access to the phosphorylated tyrosine(s) by the anti-phosphotyrosine antibody. Means for selecting suitable capture agents are described herein. Generally, the capture agent will comprise an antibody (e.g., an affinity purified polyclonal antibody or a monoclonal antibody), but other selective agents, such as streptavidin which binds selectively to the "strep-tag" polypeptide can also be used (see Schmidt et al., Protein Engineering 6(1):109–122 [1993]). Streptavidin can be purchased commercially from Zymed Laboratories, S. San Francisco, Calif., for example. Alternatively, the capture agent can comprise protein A (which binds specifically to immunoglobulins). In this embodiment of the invention, the activated receptor or receptor-construct present in the cell lysate is incubated with an antibody which binds specifically thereto, thereby forming a receptor-antibody complex. This complex can be captured by protein A by virtue of its specific binding to the antibody present in the complex. Protein A can be purchased commercially from Pharmacia Biotech, Inc., Piscataway, N.J. for example. A strategy for selecting a suitable capture agent is depicted in FIG. 3 and will be described in more detail later herein.

In the most preferred embodiment, the capture agent is a monoclonal antibody which binds specifically to a flag polypeptide (which is present in the receptor construct). Examples of suitable flag polypeptides and their respective capture antibodies include the flu HA flag and its antibody 12CA5, (Field et al., Mol. Cell. Biol. 8:2159–2165 [1988]); the c-myc flag and the 8F9, 3C7, 6E10, G4, B7 and 9E10 antibodies thereto (Evan et al., Molecular and Cellular Biology 5(12):3610–3616 [1985]); as well as the Herpes Simplex virus glycoprotein D (gD) flag and the 5B6 antibody thereto (Paborsky et al., Protein Engineering 3(6):547–553 [1990] and Mark et al., Journal of Biological Chemistry 269(14):10720–10728 [1994]). Other flag polypeptides have been disclosed. Examples include the Flag-peptide (Hopp et al., BioTechnology 6:1204–1210 [1988]); the KT3 epitope peptide (Martin et al, Science 255:192–194 [1992]); an α-tubulin epitope peptide (Skinner et al., J. Biol. Chem 266:15163–15166 [1991]); and the T7 gene 10 protein peptide tag (Lutz-Freyermuth et al., Proc. Natl. Acad. Sci. USA 87:6393–6397 [1990]). Once the flag polypeptide has been selected as discussed above, a capture antibody thereto can be generated using the techniques disclosed herein.

The term "analyte" refers to a compound or composition to be studied, usually to investigate its ability to activate (or prevent activation of) the tyrosine kinase receptor of interest. The analyte can comprise a bodily fluid (such as plasma or amniotic fluid) or a composition known to contain, or suspected of containing, a ligand for the tyrosine kinase receptor. The analyte can also comprise a cell which has a ligand to the rPTK of interest.

"Ligand" when used herein refers to a molecule which is able to bind to the ECD of the tyrosine kinase of interest or to a known agonist for the tyrosine kinase of interest. The ligand will usually be an agonist or antagonist for the tyrosine kinase.

By "agonist" is meant a molecule which is able activate the intracellular kinase domain of the tyrosine kinase upon binding to the ECD. Often, the agonist will comprise a growth factor (i.e., a polypeptide that is able to stimulate cell division). Exemplary growth factors include heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), fibroblast growth factor (FGF), transforming growth factors alpha and beta (TGF-α and TGF-β), hepatocyte growth factor (HGF), and nerve growth factor (NGF). Alternatively, the agonist can be an antibody against the rPTK (see, e.g., Yarden, Proc. Natl. Acad. Sci. USA 87:2569–2573 [1990]). However, other non-protein agonists such as small organic molecules are also encompassed by the invention.

By "antagonist" is meant a molecule which blocks agonist action. Usually, the antagonist will either: (a) bind to the rPTK and thereby block binding and/or activation of the rPTK by an agonist thereto (the antagonist may bind to the ECD of the rPTK, but this is not necessarily the case) or (b) bind to the agonist and thus prevent activation of the rPTK by the agonist. This assay facilitates the detection of both types of antagonist. The antagonist may, for example, comprise a peptide fragment comprising the receptor binding domain of the endogenous agonist ligand for the receptor. The antagonist may also be an antibody which is directed against the ECD of the rPTK, or against a known agonist for the rPTK. However, other non-protein molecules are also encompassed by this term.

The term "antibody" is used in the broadest sense and specifically covers monoclonal antibodies and antibody compositions with polyepitopic specificity (i.e. polyclonal antibodies). The polyclonal antibodies are preferably "affinity purified" antibodies. The term "affinity purified" means that the antibodies have been purified using the antigen (e.g. the rPTK or fragment thereof or the flag polypeptide) to selectively purify the polyclonal antibodies. Affinity purification can be achieved by immobilizing the antigen on an affinity column (e.g. an agarose column) and passing the polyclonal antibodies through the column. The affinity purified antibodies can be subsequently eluted from the column by changing the elution conditions or by adding a chaotropic agent, for example. For a review of affinity purification techniques with respect to antibodies, see *Current Protocols in Immunology*, Ed. Coligen et al., Wiley publishers, Vols. 1 and 2, for example.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of a selected antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. U.S. Pat. No. 4,816,567 and Mage & Lamoyi, in *Monoclonal Antibody Production Techniques and Applications*, pp.79–97 (Marcel Dekker, Inc., New York (1987)].

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256:495 (1975), or may be made by recombinant DNA methods (U.S. Pat. No. 4,816,567). The "monoclonal antibodies" may can also be isolated from phage antibody libraries using the techniques described in Clackson et al., *Nature*, 352:624–628 (1991) and Marks etal., *J. Mol. Biol.*, 222:581–597 (1991), for example.

The term "anti-phosphotyrosine antibody" refers to a molecule, usually an antibody, which binds selectively to phosphorylated tyrosine residues in the kinase domain of a rPTK. The antibody can be polyclonal, but is desirably a monoclonal antibody. Anti-phosphotyrosine polyclonal antibodies can be made using the techniques disclosed in White and Backer, *Methods in Enzymology* 201:65–67 [1991] and monoclonal anti-phosphotyrosine antibodies can be obtained commercially from Upstate Biologicals, Inc. (UBI, Lake Placid, N.Y.), for example.

The word "label" when used herein refers to a detectable compound or composition which is conjugated directly or indirectly with a molecule (such as the anti-phosphotyrosine antibody). The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or anti-phosphotyrosine antibody) is removed therefrom. To reduce background noise, it is convenient to include a detergent (e.g. Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) may be required.

By "block buffer" is meant an aqueous, pH buffered solution containing at least one blocking compound which is able to bind to exposed surfaces of the second solid phase which are not coated with capture agent. The blocking compound is normally a protein such as bovine serum albumin (BSA), gelatin, casein or milk powder and does not cross-react with any of the reagents in the assay (e.g., the anti-phosphotyrosine antibodies and detection reagents). The block buffer is generally provided at a pH between about 7 to 7.5 and suitable buffering agents include phosphate and TRIS.

By "lysis buffer" is meant an aqueous, pH buffered solution comprising a solubilizing detergent, one or more protease inhibitors and at least one phosphatase inhibitor (such as sodium orthovanadate). The term "solubilizing detergent" refers to a water miscible, non-ionic detergent which lyses cell membranes of eukaryotic cells but does not denature or activate the receptor or receptor construct. Examples of suitable non-ionic detergents include Triton-X 100, Tween 20, CHAPS and Nonidet P-40 (NP40) available from Calbiochem, La Jolla, Calif. for example. Many other non-ionic detergents are available in the art. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin and benzamidine. Preservatives (e.g., thimerosal) and one or more compounds which maintain the isotonicity of the solution (e.g., sodium chloride [NaCl] or sucrose) and a buffer (e.g., Tris or PBS) are usually also present. Generally, the pH of the lysis buffer is in the range about 7 to 7.5.

Usually, following addition of the lysis buffer to the first assay plate, the first assay plate is "gently agitated" and this expression refers to the act of physically shaking the first assay plate (normally using a circular motion) at a substantially low velocity. Gentle agitation does not involve mechanically disrupting the cells (e.g. by homogenizing or centrifuging the cells). Exemplary shaking velocities are in the order of 200 to 500 rpm, preferably 300 to 400 rpm in a Bellco orbital shaker, for example.

II. Modes for Practicing the Invention

1. Kinase Receptor Activation - KIRA

The first stage of the assay involves phosphorylation of the kinase domain of a kinase receptor, wherein the receptor is present in the cell membrane of a eukaryotic cell. The receptor may be an endogenous receptor or nucleic acid encoding the receptor may be transformed into the cell. In one embodiment of the invention, nucleic acid encoding a receptor construct is transformed into the cell. Exemplary techniques for transforming the cell with either the receptor or the receptor construct nucleic acid follow.

A. Transformation of the cells

The instant invention provides a substantial improvement over soluble kinase receptor assays insofar as it is considered to more accurately reflect the activity of the receptor in situ. It has been discovered that it is possible to transform eukaryotic cells with a receptor construct (comprising the kinase receptor and either an amino- or carboxyl-terminal flag polypeptide) so that the receptor construct assembles itself appropriately in the cell membrane and still retains tyrosine kinase activity which can be detected in the ELISA stage of the assay. This provides a generic assay for measuring tyrosine kinase activity of any tyrosine kinase of interest.

If a suitable capture agent as described herein is available for a selected rPTK, cells can be transformed with the nucleic acid encoding the receptor alone, without the flag polypeptide. Alternatively, if cells are available which produce the receptor (e.g., MCF-7 cells which produce the HER2 receptor), it is not necessary to transform the cells for use in the assay.

In order to transform the cells with the nucleic acid encoding the rPTK or receptor construct, nucleic acid encoding the rPTK and, optionally, the flag polypeptide, is isolated. This can be achieved by screening a cDNA or genomic library known to contain the DNA encoding the rPTK or flag polypeptide of interest with a selected labelled probe (e.g., an antibody or oligonucleotide- probe) for the rPTK or flag polypeptide, using standard procedures as described in chapters 10–12 of Sambrook et al., *Molecular Cloning: A Laboratory Manual* (New York: Cold Spring Harbor Laboratory Press, 1989), for example. Alternatively, the nucleic acid encoding the flag polypeptide can be made synthetically using an oligo-synthesizing machine (Applied Biosystems, Calif.). An alternative means to isolate the nucleic acid encoding the rPTK or flag polypeptide is to use PCR methodology as described in section 14 of Sambrook et al., supra. Isolation of only the ECD of the rPTK of interest is required, since this nucleic acid can be fused to the nucleic acid encoding the TM and ICD of the Rseflag polypeptide construct disclosed herein. See FIGS. 1A–1C and SEQ ID NOS: 1 and 2. If necessary however, conventional primer extension procedures as described in section 7.79 of Sambrook et al., supra, can be used to detect precursors and processing intermediates of mRNA that may not have been reverse-transcribed into cDNA.

A preferred method of practicing this invention is to use carefully selected oligonucleotide sequences to screen cDNA libraries from various tissues, preferably mammalian cell lines having the rPTK of interest. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}P$-labeled ATP with polynucleotide kinase, as is well known in the art, to radiolabel the oligonucleotide. However, other methods may be used to label the oligonucleotide, including, but not limited to, biotinylation or enzyme labeling.

In order to provide nucleic acid encoding a receptor construct, nucleic acid encoding the rPTK is fused at its 3' end to nucleic acid encoding the N-terminus of the flag polypeptide. Alternatively, the nucleic acid encoding the rPTK will be fused at its 5' end to nucleic acid encoding the carboxyl terminus of the flag polypeptide. Thus, the flag polypeptide is provided at either the carboxyl- or amino-terminus of the receptor construct. Examples of suitable flag polypeptides are provided above. Selection of other suitable flag polypeptides is possible using the techniques described herein.

In order to generate fusions between the Rse.flag reagent and a rPTK of interest, the nucleic acid encoding the ECD of the rPTK of interest is fused at its 3' end to the nucleic acid encoding the amino terminus of the Rse.flag reagent.

The nucleic acid (e.g., cDNA or genomic DNA) encoding the rPTK or receptor construct is then inserted into a replicable vector for further cloning (amplification of the DNA) or for expression. Many vectors are available to the skilled practitioner but must be compatible with the cell which is to be used in the assay. The vector will have vector components the presence of which will depend on various factors. Such components include, for example, a signal sequence, an origin of replication, one or more marker genes, an enhancer element, a promoter, and a transcription termination sequence. Selection of these vector components shall be described below.

Incorporation of a signal sequence into the expression vector is required since the rPTK or receptor construct must be transported to the cell membrane where it is positioned such that the ECD faces the external milieu of the cell. Therefore, a signal sequence suitable for positioning the rPTK or receptor construct in such a manner is used. The signal sequence is generally a component of the vector, or it may be a part of the rPTK or receptor construct DNA that is inserted into the vector. If a heterologous signal sequence is used, it is from those that are recognized and processed (i.e., cleaved by a signal peptidase) by the host cell.

For yeast secretion the native signal sequence may be substituted by, e.g., the yeast invertase leader, alpha factor leader (including Saccharomyces and Kluyveromyces α-factor leaders, the latter described in U.S. Pat. No. 5,010, 182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cells expression of the DNA encoding the native signal sequence (e.g., the rPTK presequence that normally directs secretion of rPTK from mammalian cells in vivo) is satisfactory, although other mammalian signal sequences may be suitable, such as signal sequences from other animal rPTKs, and signal sequences from secreted polypeptides of the same or related species, as well as viral secretory leaders, for example, the herpes simplex gD signal.

The DNA for such precursor region is ligated in reading frame to DNA encoding the rPTK or receptor construct.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. The 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transformed into another organism for expression. For example, a vector is cloned in *E. coli* and then the same vector is transformed into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transformation of Bacillus with this vector results in homologous recombination with the genome and insertion of rPTK or receptor construct DNA. However, the recovery of genomic DNA encoding the rPTK or receptor construct is more complex than that of an exogenously replicated vector because restriction enzyme digestion is required to excise the rPTK or receptor construct DNA.

Expression and cloning vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene express the DNA encoding a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al, *Science* 209:1422 [1980]) or hygromycin (Sugden et al., *Mol. Cell. Biol.* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the rPTK or receptor construct nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the rPTK or receptor construct. Amplification is the process by which genes in greater demand for the production of a protein critical for growth are reiterated in tandem within the chromosomes of successive generations of recombinant cells. Increased quantities of rPTK or receptor construct are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the rPTK or receptor construct. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the rPTK or receptor construct, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7(Stinchcomb et al, *Nature* 282:39 [1979]; Kingsman et al., *Gene* 7:141 [1979]; or Tschemper et al., *Gene* 10:157 [1980]). The trp1 gene provides a selection marker for a mutant strain of yeast lacking the ability to grow in tryptophan, for example, ATCC No.44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet*, 12:185 (1987). More recently, an expression system for large-scale production of recombinant calf chymosin was reported for K. lactis. Van den Berg, *Bio/Technology* 8:135 (1990). Stable multicopy expression vectors for secretion of mature recombinant human serum albumin by industrial strains of Kluyveromyces have also been disclosed. Fleer et al., *Bio/Technology* 9:968–975 (1991).

Expression and cloning vectors usually contain a promoter that is recognized by the host organism and is operably linked to the rPTK or receptor construct nucleic acid. Promoters are untranslated sequences located upstream (5') to the start codon of a structural gene (generally within about 100 to 1000 bp) that control the transcription and translation of particular nucleic acid sequence, such as the rPTK nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to rPTK or receptor construct-encoding DNA by removing the promoter from the source DNA by restriction enzyme digestion and inserting the isolated promoter sequence into the vector. Both the native rPTK promoter sequence and many heterologous promoters may be used to direct amplification and/or expression of the rPTK or receptor construct DNA. The promoter will be one which results in the accumulation of suitable numbers of receptor or receptor construct in the cell membrane of the transformed cell (i.e. so that autophosphorylation of the receptor is detectable in the ELISA but constitutive phosphorylation does not occur). Selection of a suitable promoter to achieve this is possible following the guidelines herein for selecting cells for use in the KIRA ELISA.

Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Reg.*, 7:149 [1968]; and Holland, *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al, EP 73,657A. Yeast enhancers also are advantageously used with yeast promoters.

rPTK or receptor construct transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the rPTK or receptor construct sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209:1422–1427 (1980); Pavlakis et al., *Proc. Nati. Acad. Sci. USA* 78:7398–7402 (1981). The immediate early promotor of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc. Natl. Acad. Sci. USA* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the rPTK or receptor construct by higher eukaryotes may be increased, if increased numbers of the rPTK or receptor construct per cell are required to facilitate detection in the ELISA stage of the assay. This may be achieved by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78:993 [1981]) and 3' (Lusky et al., *Mol. Cell Bio.* 3:1108 [1983]) to the transcription unit, within an intron (Banerji et al., *Cell* 33:729 [1983]), as well as within the coding sequence itself (Osborne et a., *Mol. Cell Bio.* 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the rPTK or receptor construct-encoding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the rPTK or receptor construct.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al, *Methods in Enzymology* 65:499 (1980).

Other methods, vectors, and host cells suitable for adaptation to the synthesis of the rPTK or receptor construct in recombinant vertebrate cell culture are described in Gething et al, *Nature* 293:620–625 (1981); Mantei et al, *Nature*

281:40–46 (1979); Levinson et al.; EP 117,060; and EP 117,058. A particularly useful plasmid for mammalian cell culture expression of rPTK or receptor construct DNA is pRK5 (EP 307,247) or pSVI6B (PCT pub. no. WO 91/08291 published Jun. 13, 1991).

Examples of suitable eukaryotic cell lines for transformation include *Saccharomyces cerevisiae*, Schizosaccharomyces pombe (Beach and Nurse, *Nature* 290:140 [1981]; EP 139,383 published May. 2, 1985); Kluyveromyces hosts (U.S. Pat. No. 4,943,529; Fleer et al, *Bio/Technology* 9:968–975 [1991]) and Aspergillus hosts such as *A. nidulans* (Ballance et al., *Biochem. Biophys. Res. Commun.* 112:284–289 [1983]; Tilburn et al., *Gene* 26:205–221 [1983]; Yelton et al., *Proc. Natl. Acad. Sci. USA* 81:1470–1474 [1984]) and A. niger (Kelly and Hynes, *EMBO J.* 4:475–479 [1985]), among lower eukaryotic host microorganisms.

Examples of useful animal host cell lines for transformation include monkey kidney CV1 line transformed by SV40 (COS-7, ATCC CRL 1651); human embryonic kidney line (293 or 293 cells subcloned for growth in suspension culture, Graham et al, *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. USA* 77:4216 [1980]); mouse sertoli cells (TM4, Mather, *Biol. Reporod.* 23:243–251 [1980]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 [1982]); MRC 5 cells; FS4 cells; and a human hepatoma line (Hep G2).

Host cells are transformed with the above-described expression or cloning vectors of this invention and cultured in conventional nutrient media modified as appropriate for inducing promoters, selecting transformants, or amplifying the genes encoding the desired sequences. Transformation means introducing DNA into an organism so that the DNA is replicable, either as an extrachromosomal element or as a chromosomal integrant. Depending on the host cell used, transformation is done using standard techniques appropriate to such cells. Successful transformation is generally recognized when any indication of the operation of this vector occurs within the host cell.

For mammalian cells, the calcium phosphate precipitation method of Graham and Van der Eb, *Virology* 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.* 130:946 (1977) and Hsiao et al., *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185:527–537 (1990), and Mansour et al., *Nature* 336:348–352 (1988).

The mammalian host cells used to produce the rPTK or receptor construct may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* 58:44 (1979), Barnes and Sato, *Anal. Biochem.* 102:255 (1980), U.S. Pat. Nos. 4,767,704; 4,657,866; 4,927, 762; or 4,560,655; WO 90/03430; WO 87/00195; U.S. Pat. Re. No. 30,985; or U.S. Pat. No. 5,122,469, the disclosures of each of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed., IRL Press, 1991.

Gene amplification and/or expression may be measured in a sample directly, for example, by conventional Southern blotting, Northern blotting to quantitate the transcription of mRNA (Thomas, *Proc. Natl. Acad. Sci. USA* 77:5201–5205 [1980]), dot blotting (DNA analysis), or in situ hybridization, using an appropriately labeled probe, based on the sequences provided herein. Various labels may be employed, most commonly radioisotopes, particularly $^{32}$P However, other techniques may also be employed, such as using biotin-modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining to quantitate directly the expression of gene product.

B. Selecting cells for use in the assay

As mentioned above, the cells to be subjected to the assay can be (a) cells having an endogenous receptor, (b) cells which have been transformed with a rPTK, or (c) cells transformed with a receptor construct. The suitability of the cells for use in the assay is investigated.

Cells having the endogenous rPTK can be subjected to a test-run KIRA ELISA using a known ligand to the PTK (e.g. an agonist antibody) and a control (e.g. the diluent for the agonist antibody). A range of ligand concentrations such as those used herein (see Examples 1, 2 and 3) will be used to determine whether sufficient numbers of the receptor are present in the cells being tested. In order to discover whether a cell line is unsuitable because the receptor is constitutively phosphorylated, the cell line can be subjected to the KIRA ELISA disclosed herein, wherein it is exposed to both positive and negative controls (e.g. a known agonist ligand in cell culture media as described herein as a positive control and the cell culture media without the agonist ligand as the negative control). If phosphorylation of the receptor is detected for both positive and negative controls, this may be indicative that constitutive phosphorylation of the receptor is occurring. However, it is possible that a constituent of the serum in the cell culture media is activating the receptor. Thus, the cells can be "starved" in serum-free media for about 2–12 hours (depending on cell survival) and then the assay is repeated using the positive and negative controls. If activation is detected for both controls, the cell line may be considered unsuitable and another cell line can be tested.

If the cell line is transformed with the receptor (without the flag polypeptide) a strategy similar to that depicted in FIG. 4 can be used to discover whether or not the cell line is suitable for use in the assay. As a first step, successful transformation and expression of the nucleic acid encoding the rPTK is determined (see FIG. 4, step b). In order to identify whether the ECD of the rPTK is present on the surface of the cells, flow cytometric analysis can be performed using an antibody to the ECD of the receptor. The antibody can be made using the techniques for generating antibodies discussed herein. Flow cytometric analysis can be carried out using the techniques described in *Current Protocols in Immunology*, Ed. Coligen et al., Wiley publishers, Vols. 1 and 2, for example. Briefly, flow cytometric analysis involves incubating intact cells (having the receptor) with antibodies to the ECD thereof, followed by washing. The antibody-bound cells are then incubated with species specific anti-antibody antibodies conjugated to a fluorochrome. Following washing, the labeled cells are analyzed by fluorescence-activated flow cytometry to detect whether the ECD is present on the surface of the cells.

In the following step, i.e. FIG. 4, step (c), the ability of the cell-bound receptor to be activated is tested. In order to determine this, the transformed cells are exposed to a known agonist to the receptor (e.g. the endogenous ligand or an agonist antibody for the receptor). Following exposure, the cells are lysed in a suitable buffer (e.g. sodium dodecylbenzenesulfonate in phosphate buffered saline; SDS in PBS) and subjected to Western blotting with anti-phosphotyrosine antibodies as described in Wang, *Molecular and Cellular Biology* 5(12):3640–3643(1985); Glenney et al., *Journal of Immunological Methods* 109:277–285 (1988); Kamps, *Methods in Enzymology* 201:101–110 (1991); Kozma et al., *Methods in Enzymology* 201:28–43 (1991); Holmes et al., *Science* 256:1205–10 (1992); or Corfas et al., *PNAS. USA* 90:1624–1628 (1993), for example.

Assuming the Western blotting step indicates that the rPTK can be activated, a KIRA ELISA test run can be performed, see FIG. 4 step (d), to further establish whether or not the transformed cell line can be used in the assay.

In the preferred embodiment of the invention, the KIRA ELISA is a "generic" assay insofar as any rPTK of interest can be studied regardless of the availability of receptor-specific reagents (i.e., capture agent). This embodiment employs a receptor construct having a flag polypeptide at either the amino or carboxyl terminus of the receptor.

If the flag polypeptide is provided at the $NH_2$-terminus (see, e.g., the gD.trk A, B and C receptor constructs disclosed in Example 3), the procedure for selecting a transformed cell line for use in the assay summarized in FIG. 4 can be performed. In this embodiment, the cells are transformed with the flag polypeptide-receptor construct as described earlier herein. See step (a). In step (b), successful transformation of the receptor and flag polypeptide (i.e. the receptor construct) is confirmed. In order to study this, two-dimensional flow cytometric analysis can be performed using antibodies to both the flag polypeptide and the ECD of the receptor. Techniques for two-dimensional flow cytometric analysis are disclosed in *Current Protocols in Immunology*, supra. Assuming successful transformation of the receptor construct is demonstrated, steps (c) and (d) of FIG. 4 are then performed. See the discussion above, for an explanation of steps (c) to (d) of FIG. 4.

A technique for identification of cells which have been successfully transformed with the receptor construct having a C-terminal flag polypeptide and which cells are also suitable for use in the assay is illustrated in FIG. 5. Following cell transformation [step (a)], successful transformation of the receptor is determined by flow cytometric analysis using an antibody directed against the ECD of the receptor of interest, for example. Flow cytometric analysis can be performed substantially as described above. This forms step (b) of the procedure outlined in FIG. 5.

Following step (b), successful transformation of the entire receptor construct (including the COOH-terminal flag polypeptide) is analyzed in step (c). This can be achieved by lysing the cells (using techniques for lysing cells disclosed herein) and immunoprecipitating the membrane extract with an antibody against the receptor of interest. This immunoprecipitated membrane extract is then subjected to Western blot analysis with antibodies specific for the flag polypeptide. Alternatively, rPTK-specific ELISA analysis of anti-flag polypeptide captured membrane lysate can be carried out. Briefly, this involves coating ELISA wells with appropriate flag specific capture agent. The wells are blocked, washed, and the lysate is then incubated in the wells. Unbound receptor construct is removed by washing. The wells are then reacted with receptor-specific antibody or antibodies, either directly or indirectly conjugated to HRPO. The wells are washed and the HRPO is then exposed to the chromogenic substrate (e.g., TMB).

Steps (d) and (e), i.e., detecting receptor activation and KIRA ELISA test run, are essentially the same as those steps described above.

Once useful cells are identified, they are subjected to the KIRA stage of the instantly claimed assay.

C. Coating the first solid phase with the cells

The first solid phase (e.g. a well of a first assay plate) is coated with cells having the endogenous receptor or cells which have been transformed pursuant to the preceding sections.

Preferably, an adherent cell line is chosen, so that the cells naturally adhere to the first solid phase. However, use of an adherent cell line is not essential. For example, non-adherent cells (e.g. red blood cells) can be added to round bottomed wells of an assay plate such as that sold by Becton Dickinson Labware, Lincoln Park, N.J. for example. The assay plate is then placed in a plate carrier and centrifuged so as to create a pellet of cells adhering to the base of the wells. The cell culture supernatants are removed using a pipette. Thus, use of an adherent cell is clearly advantageous over non-adherent cells since it reduces variability in the assay (i.e, the cells in the pellet of the round bottom wells may be taken up with the supernatant when the alternative method is used).

The cells to be added to the wells of the first assay plate may be maintained in tissue culture flasks and utilized when cells densities of about 70–90% confluency are achieved. Then, generally between about $1 \times 10^4$ to $3 \times 10^5$ (and preferably $5 \times 10^4$ to $1 \times 10^5$) cells are seeded per flat-bottom well, using a pipette, for example. It has been found that, contrary to expectations, addition of cell concentrations mentioned above is sufficient to enable activation of the rPTK to be measured in the ELISA stage of the assay, without the need to concentrate or clarify the cells or cell lysate prior thereto. Often, the cells are diluted in culture medium prior to seeding them in the wells of the microtiter plate to achieve the desired cell densities.

Usually, the cells are cultured in the microtiter plates for a sufficient period of time to optimize adherence to the wells thereof, but not too long such that the cells begin to deteriorate. Thus, incubation for about 8 to 16 hours at a temperature which is the physiological optimum for the cells (usually about 37° C.) is preferred. Suitable media for culturing the cells are described in Section 1A above. Culturing in 5% $CO_2$ is recommended.

Following incubation overnight, the well supernatants are decanted and excess supernatant may be further removed by lightly tamping the microtiter plates with an absorbent substrate, e.g., a paper towel, but a sponge works equally well. Thus, a substantially homogeneous layer of adhering cells remains on the internal surfaces of the individual wells of the microtiter plate. These adhering cells are then exposed to the analyte.

D. Preparation and addition of the analyte

As mentioned above, the analyte may comprise an agonist ligand (or suspected agonist) or an antagonist (or suspected antagonist) for the rPTK of interest. The ligand may be an endogenous polypeptide, or a synthetic molecule, such as an inorganic or organic molecule. Usually, the ligand is a polypeptide. This assay is useful for screening molecules which activate (or antagonize activation) of the tyrosine kinase receptor of interest. Thus, the assay can be used for developing therapeutically effective molecules.

Where the ligand is an agonist, the molecule can comprise the native growth factor e.g., heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), transforming growth factors alpha and beta (TGF-α and TGF-β), hepatocyte growth factor (HGF), fibroblast growth factor (FGF) and nerve growth factor (NGF). Many of these growth factors are available commercially. Alternatively, the growth factor can be made by peptide synthesis or recombinant techniques which are described herein. Synthetic small molecule agonists can similarly be generated by those skilled in the art using conventional chemical synthesis techniques.

Where the ligand is present in a biological fluid, the analyte can be prepared using techniques which are well known in the art. Body fluid such as blood or amniotic fluid may be used directly, however concentration may be required. If the analyte to be tested comprises a particular tissue, the cells thereof can be grown in cell culture and the supernatant can be tested for secreted ligand.

Often, the ligand is diluted in an aqueous diluent (such as cell culture media) so that a standard curve can be generated. However, the ligand may be present in a cell or a cell component (e.g., the cell membrane). In particular, it has been found that the assay can be used to detect the presence of a ligand in the cell membrane of a selected cell line. This is clearly useful for discovering a novel endogenous ligand for a known rPTK.

The ligand composition is added to each well which contains the adhering cells using a pipette, for example. At least one control well (e.g. to which the aqueous diluent for the ligand is added) is included in the assay.

The adhering cells are usually stimulated for a sufficient period of time to optimize the signal, but not too long such that the signal decreases as a consequence of dephosphorylation of the rPTK by endogenous phosphatases. A suitable stimulation period is between about 10 to 60 minutes, preferably about 30 minutes at a physiologically optimal temperature for the cells (usually about 37° C.).

Following activation, well supernatants are decanted and the plates can then be lightly tamped with an absorbent substrate to remove excess supernatant.

The assay can be used to detect antagonist ligands for the rPTK of interest. Antagonists generally fall into two categories (a) ones which bind to the rPTK and thereby block binding and/or activation of the rPTK by an agonist thereto (the antagonist may bind to the ECD, but this is not necessarily the case) and (b) those which bind to the agonist and thus prevent activation of the rPTK by the agonist.

In order to detect antagonist molecules from category (a) above, the cells are exposed to the suspected antagonist ligand substantially as mentioned above. Following exposure to the antagonist, the well supernatants are decanted and the plates are lightly tamped. Then, a known agonist (e.g., the endogenous growth factor) is added to the washed cells essentially as discussed in the preceding paragraphs, following which, the well supernatants are decanted and plates are lightly tamped. Alternatively, a composition comprising both the antagonist and agonist can be added to the adhering cells substantially as discussed above. Ability of the suspected antagonist to block binding and/or activation of the rPTK can subsequently be measured by ELISA as discussed below.

To detect antagonist molecules from category (b) above, a known agonist is pre-incubated with the suspected antagonist prior to the KIRA stage of the assay. This incubation is carried out for a sufficient period of time to enable a complex of the antagonist-agonist to form; from 30 min. to 12 hours, for example. This complex is then subjected to the assay with the non-complexed agonist and antagonist used as controls.

Following exposure to the agonist (and optionally the antagonist) ligand, the cells are lysed, as discussed below.

E. Solubilizing the cells

In this step of the assay, the cells are lysed so as to solubilize the rPTK such that it remains activated (i.e., the tyrosine residues remain phosphorylated) for the ELISA stage of the assay. Thus, the cells are lysed using a lysis buffer as described above which serves to solubilize the rPTK or receptor construct, yet does not dephosphorylate or denature the rPTK.

Where microtiter plates are used as mentioned above, about 75 to 200 μl of lysis buffer is added to each well. The plates can then be agitated gently using a plate shaker (e.g., such as that sold by Bellco Instruments, Vineland, N.J.) for about 1 to 2 hours. Shaking can be carried out at room temperature.

2. Enzyme-Linked Immunosorbent Assay - ELISA

The second stage of the assay involves a sandwich ELISA performed in the second assay plate. In order to carry out the ELISA, a capture agent is prepared.

A. Preparation of the capture agent

As mentioned above, the capture agent often comprises a polyclonal antibody (usually an affinity purified polyclonal antibody) or monoclonal antibody. Other capture agents are envisaged and are discussed in the definitions section above. The capture agent either binds specifically to the kinase receptor, or to the flag polypeptide (i.e. the antigen).

Polyclonal antibodies to the antigen (either the receptor or the flag polypeptide) generally are raised in animals by multiple subcutaneous (sc) or intraperitoneal (ip) injections of the antigen or an antigenic fragment thereof (often the ECD of the rPTK) and an adjuvant. It may be useful to conjugate the antigen or a fragment containing the target amino acid sequence to a protein that is immunogenic in the species to be immunized (e.g., keyhole limpet hemocyanin), using a bifunctional or derivatizing agent.

The route and schedule for administration of immunogen to the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. 7 to 14 days later animals are bled and the serum is assayed for anti-antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies can be prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones producing the desired antibody. The hybridoma technique described originally by Kohler and Milstein, *Eur. J. Immunol.* 6:511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are then sterile filtered. Where the antibody is a polyclonal antibody, it is generally affinity purified using an affinity column generated from the antigen of interest so as to provide a substantially specific capture antibody. Affinity chromatography is usually preceded by other purification techniques, such as liquid chromatography.

In a further embodiment, antibodies or antibody fragments can be isolated from antibody phage libraries generated via the techniques described in McCafferty et al, *Nature*, 348:552–554 (1990), using the flag polypeptide, rPTK, or a fragment thereof, to select for a suitable antibody or antibody fragment. Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Technol.* 10:779–783 [1992]), as well as combinatorial infection and in vivo recombination as a strategy for constructing very large phage libraries (Waterhouse et al., *Nuc. Acids Res.*, 21:2265–2266 [1993]). Thus, these techniques are viable alternatives to traditional monoclonal antibody hybridoma techniques for isolation of "monoclonal" antibodies which are encompassed by the present invention.

DNA encoding the monoclonal antibodies of the invention is readily isolated and sequenced using conventional procedures le.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al, *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-rPTK or anti-flag polypeptide monoclonal antibody herein. Thus, the antibody may be made by recombinant DNA methods (Cabilly et al., U.S. Pat. No. 4,816,567).

Binding of the capture agent is not affected by the presence or absence of a ligand bound to the receptor and the capture agent does not sterically block access to the phosphorylated tyrosine(s) by the anti-phosphotyrosine antibody. Furthermore, the capture agent does not, of course, activate the receptor of interest. In order to screen for an antibody having these characteristics, the procedure outlined in FIG. 3 can be carried out.

First, once the capture agent (e.g. an antibody or streptavidin) has been chosen, binding to either the receptor or the flag polypeptide (where a receptor construct is to be used in the assay) is confirmed. This can be determined by flow cytometric analysis, immunoprecipitation or antigen-coat ELISA, for example. Flow cytometric analysis has been described above. Immunoprecipitation usually involves lysing the cells (having the receptor or receptor construct) in non-ionic detergent (e.g. 0.5% Triton X-100) in a suitable buffer (e.g. PBS) and the cell lysates thus obtained are then incubated with the potential anti-receptor or anti-flag polypeptide capture agent. The immune complexes are precipitated with either (a) anti-capture agent antibodies in the presence of polyethylene glycol (PEG) which enhances precipitation of the immune complex or with (b) insoluble (e.g. agarose bound) protein A or protein G. The immunoprecipitated material is then analyzed by polyacrylamide gel electrophoresis (PAGE). For antigen-coat ELISA, ELISA wells are coated overnight with either the purified receptor, purified flag polypeptide or purified receptor construct. The coated wells are then exposed to the potential capture agent and screened with HRPO-conjugated species specific anti-capture agent antibody.

The ability of the capture agent to bind to the receptor or flag polypeptide in the presence of a ligand to the receptor is also confirmed. This can be analyzed by incubating the receptor or receptor construct with a known ligand for the receptor (e.g. the endogenous growth factor or an agonist antibody thereto). Flow cytometric analysis, immunoprecipitation or antigen-coat ELISA can then be performed substantially as described above to investigate binding of the capture agent.

Assuming the capture agent is suitable as determined by the preceding two steps, it is then shown that the capture agent does not induce receptor activation (i.e. autophosphorylation) either before or after cell lysis. Thus, the cell-bound receptor or receptor construct is exposed to either the potential capture agent or a negative control (e.g. a control antibody which does not activate the receptor). Following cell lysis, the receptor or receptor construct can be subjected to Western blot analysis using labeled anti-phosphotyrosine antibodies. See, e.g., Glenney et al., *Journal of Immunological Methods* 109:277–285 (1988); Kamps, *Methods in Enzymology* 201:101–110 (1991); Kozma et al., *Methods in Enzymology* 201:28–43 (1991); or Holmes et al., *Science* 256:1205–10 (1992). To establish whether the capture agent induces receptor activation following cell lysis, a trial run of the KIRA ELISA (with both the capture agent and a negative control as discussed above) can be performed.

Finally, the ability of an anti-phosphotyrosine antibody (e.g. biotinylated antiphosphotyrosine antibody) to bind the activated receptor in the presence of the potential capture agent is confirmed by a trial run in the KIRA ELISA disclosed herein.

Assuming the capture agent meets all the criteria specified above, it has good potential for use in the KIRA ELISA.

Once a suitable capture agent has been prepared, the second solid phase is coated therewith. Between about 0.1 to 10 $\mu$g/ml of capture agent can be added to each well of the second assay plate using a pipene, for example. The capture agent is often provided in a buffer at a high pH (e.g., between about 7.5 to 9.61 so that it has an increased overall charge and therefore displays enhanced binding to the second assay plate. Usually, the capture agent will be incubated in the wells for between about 8 to 72 hours to enable a sufficient coating of the capture agent to form on the inside walls of the wells. This incubation is generally carried out at low temperatures (e.g., between about 3–8° C.) to avoid or reduce degradation of the capture agent.

Following incubation, the wells of the plate are decanted and tamped lightly with an absorbent substrate. Non-specific binding is then blocked. In order to achieve this, a block buffer, is added to the wells. For example, a block buffer containing bovine serum albumin (BSA) such as that sold by Intergen Company, Purchase, NY, is suitable. It has been found that addition of between about 100 to 200 $\mu$l of block buffer to each well followed by gentle agitation at room temperature for between about 1–2 hours is sufficient to block non-specific binding. It is also possible to add the block buffer directly to the cell lysate obtained in the previous step rather than to the second assay plate.

Following this, the capture agent-coated plates are washed several times (usually between about 3–8 times) with a wash buffer. The wash buffer can comprise phosphate buffered saline (PBS) at pH 7.0 to 7.5, for example. However, other wash buffers are available which can also be used. Conveniently, an automated plate washer, such as the ScanWasher 300 (Skatron Instruments, Inc., Sterling, Va.) can be used for this, and other, washing steps of the assay.

B. Measuring tyrosine phosphorylation

The activated, solubilized rPTK (or receptor construct) is then added to the wells having the capture agent adhering thereto. As a general proposition, about 80% of cell lysate obtained as mentioned under Section 1E above can be added to each well (i.e., about 60 to 160 $\mu$l depending on the original volume of the wells). The lysate is incubated with the capture agent for an adequate period of time to enable the rPTK to be captured in the wells, e.g., from 1 to 3 hours. Incubation can be carried out at room temperature.

Unbound cell lysate is then removed by washing with wash buffer. Following this washing step, an amount of the anti-phosphotyrosine antibody which is equal to, or less than, the amount of block buffer added previously, is added to each well. For example, about 50 to 200 $\mu$l of an anti-phosphotyrosine antibody preparation having between about 0.3 to 0.5 $\mu$g/ml of antibody in a suitable buffer (e.g., PBS with a detergent such as those included in the lysis buffer) is added to the well. This is followed by a washing step to remove unbound anti-phosphotyrosine antibody.

Tyrosine phosphorylation is then quantified by the amount of anti-phosphotyrosine antibody binding to the second solid phase. Many systems for detecting the presence of an antibody are available to those skilled in the art. Some examples follow.

Generally, the anti-phosphotyrosine antibody will be labelled either directly or indirectly with a detectable label. Numerous labels are available which can be generally grouped into the following categories:

(a) Radioisotopes, such as $^{35}$S, $^{14}$C, $^{125}$I, $^{3}$H, and $^{131}$I . The antibody can be labeled with the radioisotope using the techniques described in *Current Protocols in Immunology*, supra, for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of *Enzyme-Antibody* Conjugates for use in Enzyme Immunoassay, in *Methods in Enzym.* (ed J. Langone & H. Van Vunakis), Academic press, New York, 73:147–166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]).

(ii) alkaline phosphatase (AP) with para-Nitrophenyl phosphate as chromogenic substrate.

(iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. See, *Current Protocols in Immunology*, supra, for a review of techniques involving biotin-avidin conjugation. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-phosphotyrosine antibody need not be labeled, and the presence thereof can be detected using a labeled anti-antiphosphotyrosine antibody (e.g. anti-mouse anti-phosphotyrosine antibody conjugated with HRPO).

In the preferred embodiment, the anti-phosphotyrosine antibody is labeled with an enzymatic label which catalyzes a color change of a substrate (such as tetramethyl benzimidine [TMB], or orthaphenylene diamine [OPD]). Thus, the use of radioactive materials is avoided. A color change of the reagent can be determined spectrophotometrically at a suitable wavelength (e.g. 450 nm for TMB and 490 nm for OPD, with a reference wavelength of 650 nm).

3. Kits

As a matter of convenience, the reagents can be provided in a kit, i.e., a packaged combination of reagents, for combination with the analyte in assaying the ability of the analyte to activate or prevent activation of a rPTK of interest. The components of the kit will be provided in predetermined ratios. Thus, a kit will comprise the specific second solid phase for the assay as well as the anti-flag polypeptide capture agent either packaged separately or captured to the second solid phase (e.g. a microtiter plate). Usually, other reagents, such as the anti-phosphotyrosine antibody labelled directly or indirectly with an enzymatic label will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. a block buffer and a lysis buffer) and the like. Conveniently, the kit can also supply the homogeneous population of cells which have been transformed with the receptor construct. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the KIRA ELISA.

4. Uses for the Assay

This application provides two assays which are useful for reliable, sensitive and quantitative detection of kinase activation. The first assay can be used where a kinase receptor-specific capture antibody having the desired characteristics herein described is available or has been prepared. The second assay is a generic assay which enables activation of any kinase receptor to be measured via the use of a flag polypeptide and a capture agent which binds specificity thereto.

These assays are useful for identifying novel agonists/antagonists for a selected kinase receptor. Also, the assay provides a means for studying ligand-receptor interactions (i.e., mechanism studies). Also the presence of an endogenous receptor in a selected cell line can be quantified using the assay. The assays are further useful for identifying the presence of a ligand for a selected kinase receptor in a biological sample and, e.g., establishing whether a growth factor has been isolated following a purification procedure. It is desirable to have an assay for measuring the ability of these growth factors to activate their respective receptors.

The assay also has clinical applications for detecting the presence of a ligand for a selected rPTK (e.g. the insulin receptor) in a biological sample taken from a human and thus patients having elevated or depressed levels of the ligand can be identified. This is particularly desirable where elevated or depressed levels of the ligand cause a pathological condition. Accordingly, candidates for administration of the selected ligand (e.g. insulin) can be identified through this diagnostic method. It is possible, using the assay disclosed herein, to assay the pK of agonists or antagonists administered to a patient. This assay also facilitates the detection of shed receptor in a biological sample.

Below are examples of specific embodiments for carrying out the present invention. The examples are offered for illustrative purposes only, and are not intended to limit the scope of the present invention in any way.

EXAMPLE 1

KIRA ELISA of the HER2 Receptor

The assay system described in this example was developed to measure the extent of autophosphorylation as a result of the interactions between the HER2 receptor and its specific activator, heregulin (HRG). The overexpression of p185$^{HER2}$ has been correlated with poor clinical outcome in a number of epithelial-derived cancers. Heregulin and its rodent homologue, neu differentiation factor (NDF), were originally purified based on their ability to stimulate the autophosphorylation of a 185 kDa protein in the breast carcinoma cell lines MCF-7 and MDA)453, respectively. In this embodiment of the invention, the cell line expressing the tyrosine kinase receptor DNA (either endogenous or transformed) is adherent and there is an antibody (e.g. monoclonal or affinity purified polyclonal) capable of specifically binding the receptor such that it neither stimulates autophosphorylation in the absence of ligand nor suffers impaired binding due to the presence of bound ligand. Standard curve preparations and many samples may easily be run simultaneously in replicate and at several dilutions using this assay, readily allowing quantitation of ligand activity in a large number of unknown samples.

(i) Capture agent preparation

Polyclonal anti-HER2 antibody was isolated from pooled immune sera from New Zealand White rabbits immunized with the extracellular domain of the HER2 molecule (Fendly et al., *Journal of Biological Response Modifiers* 9:449–455 [1990]). The rHER2 ECD specific antibodies were affinity purified using an FPLC (Pharmacia Biotech, Inc, Piscataway, N.J.) with an affinity column generated from rHER2 ECD conjugated to Avidgel F (Bioprobe International, Inc, Tustin, Calif.). The resulting purified antibody stock was 0.829 mg/ml in phosphate buffered saline (PBS), pH 7.4, and was stored as 0.5 ml aliquots at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligand

The recombinant truncated form of β1heregulin (MW= 7.88 Kd) corresponding to residues 177–244 (HRGβ1$_{177-244}$) was produced in *E. coli* and purified to homogeneity as described in Holmes et al., *Science*, 256:1205–1210 (1992) and was stored at 4° C. as an 89.7 μM stock solution in 50 mM Tris/HCl, pH 7.5.

(iv) Adherent Cells

MCF-7 (ATCC-HTB 22), an adherent cell line isolated from a human breast adenocarcinoma, was obtained from American Type Culture Collection (ATCC, Rockville, Md.). MCF-7 cells have been shown to produce measurable levels of surface p185$^{HER2}$ by both FACS and ELISA analysis. The cells were maintained in 150 cm² tissue culture flasks (Corning Inc, Corning, N.Y.) and utilized when at cell densities of 60% to 75% confluency. For the assay, 2×10⁵ cells were seeded per well in flat-bottom microtiter plates (Falcon 3072, Becton Dickinson Labware, Lincoln Park, N.J.) cultured overnight at 37° C. in 5% CO$_2$. Cells were grown in F12/DMEM 50:50 Gibco as a custom formulation (Gibco/BRL, Life Technologies, Grand Island, N.Y.). The medium was supplemented with 10% FBS (HyClone, Logan, Utah), 25 mM HEPES (Gibco) and 2 mM L-glutamine (Gibco).

(v) KIRA ELISA

MCF-7 cells (2×10⁵) in 100 μl media were added to each well in a flat-bottom-96 well culture plate and cultured overnight at 37° C. in 5% CO$_2$. The following morning the well supernatants were decanted, and the plates were lightly tamped on a paper towel. 50 μl of media containing either experimental samples or the recombinant HRGβ1$_{177-244}$ standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate (Na$_3$VO$_4$, Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the affinity-purified polyclonal anti-HER2 ECD (1.0 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-HER2 ECD coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized p185$^{HER2}$ from the cell-culture microtiter well was transferred (85 μl/well) to anti-rHER2 ECD coated and blocked ELISA well and was incubated for 2 h at room temperature with gentle agitation. The unbound receptor was removed by washing with wash buffer and 100 μl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0 M H$_3$PO$_4$. The absorbance at 450 nm was read with a reference wavelength of 650 nm (ABS$_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 7 was generated by stimulating MCF-7 cells with 3000, 1000, 333, 111, 37, 12, 4, or 0 pM HRGβ1$_{177-244}$ and presented as pM HRGβ1$_{177-244}$ vs. mean ABS$_{450/650}$ ±sd using the DeltaSoft program. Sample concentrations were obtained by interpolation of their absorbance on the standard curve and are expressed in terms of pM HRGβ1$_{177-244}$ activity.

When the data were fitted to a 4-parameter nonlinear least squares equation, they resulted in a correlation coefficient of 0.9998. For the data shown in FIG. 7, the EC$_{50}$ of receptor activation by HRGβ1$_{177-244}$ was 373 pM. To demonstrate the highly reproducible nature of the p185$^{HER2}$ KIRA ELISA, seven standard curves were generated over the period of one month and the EC$_{50}$'s are averaged. This gives an EC$_{50}$ ave for HRGβ1$_{177-244}$ of 360±40 pM (average±SD).

(vi) Intra- and inter-assay precision and assay specificity

The intra-assay variability was determined by performing the p185$^{HER2}$ KIRA ELISA on three separate days. For each test, the standard curve is run in triplicate. Controls with HRGβ1$_{177-244}$ corresponding to high (1000 pM), mid (200 pM) and low (40 pM) were assayed in 24 replicates. The ABS$_{450/650}$ of the individual test samples were converted to pM HRGβ1$_{177-244}$ activity and the 24 converted values for each test concentration were averaged. The data are expressed as averaged value and % coefficient of variation (% cv; [(intra-assay standard deviation/intra-assay averaged calculated value)×100]. See Table 1A below.

TABLE 1

Intra- and Inter-assay Variation

A. Intra-assay Precision (n-24 per test)

| | High Value[a] | | Mid Value | | Low Value | |
|---|---|---|---|---|---|---|
| | Average Value (pM) | % cv[b] | Average Value (pM) | % cv | Average Value (pM) | % cv |
| Test#1 | 1256 | 19.5% | 209 | 10.8% | 33 | 12.3% |
| Test#2 | 1078 | 10.0% | 196 | 5.1% | 38 | 7.5% |
| Test#3 | 999 | 14.3% | 196 | 6.3% | 35 | 11.3% |

B. Inter-assay Precision (n = 3)

| Average Value (pM) | % cv[c] | Average Value (pM) | % cv | Average Value (pM) | % cv |
|---|---|---|---|---|---|
| 1100 | 4.3% | 200 | 6.3% | 34 | 9.0% |

[a]Expected high value: 1000 pM; mid value: 200 pM; low value: 40 pM
[b]Intra-assay % cv determined as intra-assay sd/intra-assay average × 100
[c]Inter-asay % cv determined as inter-assay sd/inter-assay average × 100

The intra-assay variability of the KIRA ELISA was within acceptable limits despite the fact that the assay actually consists of both bioassay and ELISA components. The coefficients of variance (%) for the highest values were under 20% and for the mid and low values were at or under 10%.

The inter-assay variability was determined by averaging the values from upper-most three adjacent wells (of the 24 wells run) for a given sample concentration from each run. The three separate averages for each test concentration were then averaged. The data were expressed as averaged value and % cv [(inter-assay standard deviation/inter-assay averaged value) ×100]. See Table 1B. above. The inter-assay variability of the KIRA ELISA was within acceptable limits.

In order to confirm the specificity of the assay, MCF-7 cells were stimulated with either HRGβ1$_{177-244}$ at 3000, 1000, 333, 111, 37, 12, 4 or 0 pM or insulin-like growth factor-1 (IGF-1), epidermal growth factor (EGF), vascular endothelial growth factor (VEGF), or insulin at 30000, 10000, 3333, 1111, 370, 120, 40 or 0 pM. The p185$^{HER2}$ KIRA ELISA was then performed as described above. The results are depicted in FIG. 8.

The p185$^{HER2}$ KIRA ELISA was clearly specific for heregulin. While HRGβ1$_{177-244}$ induced normal receptor stimulation and autophosphorylation, the closely related EGF gives only a slight stimulation (OD$_{450/650}$=0.239) at the highest concentration tested (100 nM). Since EGF-R is produced in MCF-7 cells, this signal is likely due to EGF receptor transphosphorylation of p185$^{HER2}$. Neither insulin-like growth factor-1 (IGF-1), vascular endothelial growth factor (VEGF) nor insulin have any detectable effect on the MCF-7 p185$^{HER2}$ KIRA ELISA, the latter despite the fact that MCF-7 cells produce active insulin receptors.

The results presented in this example demonstrate that the KIRA ELISA is a useful method for assaying ligand activation of a kinase receptor, e.g., heregulin activation of the p185$^{HER2}$ receptor. Levels of receptor activation in terms of tyrosine phosphorylation are easily quantified and an EC$_{50}$ for a given ligand is readily determined. One potential use for this assay would be to screen compounds for receptor agonist or antagonist activities. The potential throughput for this assay greatly surpasses that of Western blot analysis. Since the cell-culture portion of the assay is conducted in 96-well plates, many samples may be run in replicate at different dilutions at one time in a one-day assay.

EXAMPLE 2

KIRA ELISA of the Rse Receptor

Mark et al., *Journal of Biological Chemistry* 269(14) :10720–10728 (1994) describe isolation of the Rse receptor protein tyrosine kinase from human and murine tissues. This Rse receptor with a carboxyl-terminal flag polypeptide (i.e. Rse.gD) was subjected to the KIRA ELISA described herein. The experimental procedure is outlined below.

(i) Capture agent preparation

Monoclonal anti-gD (clone 5B6) was produced against a peptide from Herpes simples virus glycoprotein D (Paborsky et al., *Protein Engineering* 3(6):547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligand

Since the endogenous ligand for the Rse receptor was not available, an agonist antibody for the Rse receptor was prepared which forms the ligand for the KIRA ELISA described in this Example. To generate the agonist antibody, a Rse.IgG chimera was generated. Briefly, the coding sequence of the ECD of Rse was fused to that of the human IgG-y1 heavy chain in a multi-step process. PCR was used to generate a fragment with a unique BstEll site 3' to the coding sequences of the Rse amino acid 428. The PCR product was joined to the human IgG-y$_1$ heavy chain cDNA through a unique BstEII site in that construct (Mark et al.,*J. Cell. Biol.,* 267: 26166–26171 [1992]). The resulting construct (termed pRK.bpTK3.IgG.fusion) contained the coding sequences for amino acids 375–428 of Rse joined to those encoding human IgG-y$_1$ heavy chain. The remaining portion of the Rse ECD (amino acids 1-374) was then added by linkage through the Bam HI site in pRK.bpTK3.IgG.fusion to yield pRK.Rse.IgG.

To generate stable cell populations expressing Rse.IgG, the cDNA encoding Rse.IgG was subcloned into the episomal CMV-driven expression plasmid pCIS.EBON, a pRK5 derivative disclosed in Cachianes et al., *Bio. Techniques*, 15: 225–259 (1993). Human fetal kidney 293 cells (obtained from ATCC, 12301 Parklawn Drive, Rockville, Md., USA) were transfected by the calcium phosphate technique. Cell monolayers were incubated for four hours in the presence of the DNA precipitate, glycerol shocked, and cultured in F12:DMEM (1:1) containing 2 mM glutamine, 10% fetal bovine serum, penicillin and streptomycin. After 48 hours, populations were replated in media containing G418 to select for a stable population of cells. Conditioned media was collected from cells expressing Rse.IgG nucleic acid that have been cultured in serum-free media for 72 hours in the absence of G418.

Rse.IgG was purified by affinity chromatography on a protein A column using procedures as described by Chamow, S.M., et al., *Biochemistry*, 29:9885–9891 (1990) with the following minor modifications. Conditioned media collected from cells expressing the Rse.IgG was adjusted to 0.1M citrate pH 6.0 and loaded directly onto a protein A column (Repligen). The column was washed with 0.1M citrate, pH 6.0, and was eluted with 3M $MgCl_2$ with 10% glycerol. Fractions were pooled and desalted on a PD-10 column, dialyzed and concentrated against PBS. Protein concentrations were determined by an ELISA against human IgG (Fc). The protein was analyzed for purity by Coomassie staining of PAGE gels.

Polyclonal antibodies were generated in New Zealand white rabbits against the Rse.IgG formed as described above. 4 μg of Rse.IgG in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93, 3–12 [1983]). For subsequent boosts, the protein was injected into subcutaneous and intramuscular sites. 1.3 μg protein/kg body weight was injected every 3 weeks with bleeds taken 1 and 2 weeks following each boost. The polyclonal antisera generated was then precipitated in 50% ammonium sulphate.

The resultant, purified polyclonal antisera is called "19B" herein. To confirm the ability of the 19B antisera to induce autophosphorylation of the Rse receptor, serum starved 3T3.gD.R11 cells (transformed with nucleic acid encoding the Rse receptor with an amino terminal gD flag polypeptide [ie. gD.Rse] using the techniques described in Mark et al., *Journal of Biological Chemistry* 269(14):10720–10728 [1994]) or NIH3T3 cells were exposed to pre-immune serum or 19B polyclonal antisera at a 1:200 dilution for 10 minutes. The gD.Rse protein was immunoprecipitated from extracts using the anti-gD monoclonal antibody 5B6. Proteins were fractionated on 7% SDS-PAGE under reducing conditions and transferred to nitrocellulose. Phosphorylation of Rse was detected with labelled anti-phosphotyrosine antibody. Treatment of the 3T3.gD.R11 cells with 19B antisera stimulated the phosphorylation of the 140kD gD.Rse protein. This increase was not observed in cells treated with pre-immune sera.

The purified 19B polyclonal antisera was stored at 4° C. as an 2.8 mg/ml stock solution in PBS, pH 7.5.

(iv) Preparation of Rse.gD nucleic acid

Synthetic double stranded oligonucleotides were used to reconstitute the coding sequence for the C-terminal 10 amino acids (880–890) of human Rse and add an additional 21 amino acids containing an epitope for the antibody 5B6 and a stop codon. The final sequence of the synthetic portion of the fusion gene was: coding strand:
5'-TGCAGCAAGGGCTACTGCCACACTCGAGCTGCG CAGATGCTAGCCTCAAGATGGCTGATCCAA ATC-GATTCCGCGGCAAAGATCTTCCGGTCCTGT AGAAGCT-3'(SEQ ID NO:10) noncoding (anti-sense) strand:
5'-AGCTTCTACAGGACCGGAAGATCUTGCCGCGG AATCGATIIGGATCAGCCATCTTGAGGCTAGC ATCTGCGCAGCTCGAGTGTGGCAGTAGCCCT TGCTGCA-3'(SEQ ID NO:11).

The synthetic DNA was ligated with the cDNA encoding amino acids 1–880 of human Rse at the PstI site beginning at nucleotide 2644 of the published human Rse cDNA sequence (Mark et al., *Journal of Biological Chemistry* 269(14):10720–10728 [1994]) and HindIII sites in the polylinker of the expression vector pSV17.ID.LL (See FIG. 16; SEQ ID NO:9) to create the expression plasmid pSV.ID.Rse.gD. Briefly, the expression plasmid comprises a dicistronic primary transcript which contains sequence encoding DHFR bounded by 5' splice donor and 3' splice acceptor intron splice sites, followed by sequence that encodes the Rse.gD. The full length (non-spliced) message contains DHFR as the first open reading frame and therefore generates DHFR protein to allow selection of stable transformants.

(v) Cell transformation dp12.CHO cells (EP 307,247 published Mar. 15, 1989) were electroporated with 20 μgs of pSV.ID.Rse.gD which had been linearized at a unique NotI site in the plasmid backbone. The DNA was ethanol precipitated after phenol/chloroform extraction and was resuspended in 20 μl 1/10 Tris EDTA. Then, 10 μg of DNA was incubated with $10^7$ CHO.dp 12 cells in 1 ml of PBS on ice for 10 min. before electroporation at 400 volts and 330 μf. Cells were returned to ice for 10 min. before being plated into non-selective medium. After 24 hours cells were fed nucleoside-free medium to select for stable DHFR+clones.

(vi) Selection of transformed cells for use in the KIRA ELISA

To identify a cell line that expresses Rse.gD nucleic acid, candidate clones were screened by fluorescence activated cell sorting (FACS) analysis using the polyclonal antiserum 19B generated as described above, which recognizes epitopes in the extracellular domain of Rse. See FIG. 5, step (b).

To confirm that clones that scored positive in the FACS assay express full-length Rse.gD nucleic acid, cell lysates were prepared (Lokker et al., *EMBO J*, 11:2503–2510 [1992]) and solubilized Rse.gD was immunoprecipitated with the 19B antisera. The immunoprecipitated proteins were fractionated under reducing conditions using 7% PAGE, blotted onto nitrocellulose and then probed with the anti-gD 5B6 antibody which was detected with a horseradish peroxidase conjugated anti-mouse IgG antibody. See FIG. 5, step (c). The ability of Rse.gD in cell clones to be activated to undergo autophosphorylation in response to the 19B agonistic antibody was determined. Briefly, serum starved dp.CHO cells transformed with Rse.gD nucleic acid as described above were exposed to pre-immune or 19B antisera at a 1:200 dilution for 10 min. The Rse.gD protein was immunoprecipitated from extracts using the anti-gD 5B6 monoclonal antibody. Proteins were fractionated on 7% SDS-PAGE under reducing conditions and transferred to nitrocellulose. Phosphorylation of Rse was detected with labelled antiphosphotyrosine antibody. See FIG. 5, step (d).

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA

Rse.gD transformed dp12.CHO cells (EP 307,247 published Mar. 15, 1989) were seeded ($5 \times 10^4$ per well) in the wells of a flat-bottom-96 wel culture plate in 100 $\mu$l media and cultured overnight at 37° C. in 5% $CO_2$. The following morning the well supernatants were decanted, and the plates were lightly tamped on a paper towel. 100 $\mu$l of media containing either experimental samples or 1:100, 1:200, 1:400, 1:800, 1:1600, 1:3200 or 0 diluted, anti-Rse agonist polyclonal antibody (19B pAb) was then added to each well. The cells were stimulated at 37° C. for 30 min., the well supernatants were decanted, and the plates were once again lightly tamped on a paper towel. To lyse the cells and solubilize the receptors, 100 $\mu$l of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, OH), 1 mM 4-(2-aminoethyl)-benzenesulfonyl fluoride hydrochloride (AEBSF; ICN Biochemicals), 50 $\mu$M leupeptin (ICN Biochemicals), and 2 mM sodium orthovanadate ($Na_3VO_4$; Sigma Chemical Co, St. Louis, Mo.), pH 7.5. The plate was then agitated gently on a plate shaker (BelIco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 $\mu$g/ml in 50 mM carbonate buffer, pH 9.6, 100 $\mu$l/well) was decanted, tamped on a paper towel and blocked with 150 $\mu$l/well of Block Buffer [PBS containing 0.5% BSA (Intergen Company, Purchase, NY) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized Rse.gD from the cell-culture microtiter well was transferred (85 $\mu$l/well) to anti-gD 5B6 coated and blocked ELISA well and was incubated for 2 h at room temperature with gentle agitation. The unbound Rse.gD was removed by washing with wash buffer and 100 $\mu$l of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml was added to each well. After incubation for 2 h at room temperature the plate was washed and 100 $\mu$l of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 $\mu$l freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 $\mu$l/well 1.0M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 10 was generated by stimulating Rse.gD transformed CHO cells with 1:100, 1:200, 1:400, 1:800, 1:1600, 1:3200 or 0 diluted, anti-Rse agonist antibody (19B) and presented as 1/dilution anti-Rse agonist antibody (19B) vs. mean $ABS_{450/650} \pm sd$ using the DeltaSoft program.

The results presented in this example demonstrate that the KIRA ELISA is a useful method for assaying ligand activation of a receptor construct having a carboxyl terminal flag polypeptide, e.g., activation of Rse.gD. Levels of receptor activation in terms of tyrosine phosphorylation are easily quantified and an $EC_{50}$ for a given ligand (e.g. an agonist antibody for the receptor) is readily determined.

EXAMPLE 3

KIRA ELISA of the trk A, B and C Receptors

Neurotrophins belong to a family of small, basic proteins which play a crucial role in the development and maintenance of the nervous system. The first identified and probably best understood member of this family is nerve growth factor (NGF). See U.S. Pat. No. 5,169,762, issued Dec. 8, 1992. Recently, sequentially related but distinct polypeptides with similar functions to NGF have been identified. For example, brain-derived neurotrophic factor (BDNF), now also referred to as neurotrophin-2 (NT2), was cloned and sequenced by Leibrock et al. (*Nature,* 341:149–152 [1989]). Several groups identified a neurotrophic factor originally called neuronal factor (NF), and now referred to as neurotrophin-3 (NT3). (Ernfors et al., *Proc. Natl. Acad. Sci. USA,* 87: 5454–5458 [1990]; Hohn et al., *Nature,* 344: 339 [1990]; Maisonpierre et al., *Science,* 247: 1446 [1990]; Rosenthal et al., Neuron, 4: 767 [1990]; Jones and Reichardt, *Proc. Natl. Acad. Sci. USA,* 87: 8060–8064 [1990]; Kaisho et al., *FEBS Lett.,* 266: 187 [1990]). Neurotrophins-4 and -5 (NT4 and NT5) have been recently added to the family (Hallbook et al., *Neuron,* 6: 845–858 [1991]; Berkmeier et al., *Neuron,* 7: 857–866 [1991]; Ip et al., *Proc. Natl. Acad. Sci. USA,* 89: 3060–3064 [1992]).

Neurotrophins, similarly to other polypeptide growth factors, affect their target cells through interactions with cell surface rPTKs (called Trk receptors). The first member of the trk receptor family, trkA, was initially identified as the result of an oncogenic transformation caused by the translocation of tropomyosin sequences onto its catalytic domain. Later work identified trkA as a signal transducing receptor for NGF. Subsequently, two other related receptors, mouse and rat trkB (Klein et al., *EMBO J.,* 8: 3701–3709 [1989]; Middlemas et al., *Mol. Cell. Biol.,* 11: 143–153 [1991]; EP 455,460 published Nov. 6, 1991) and porcine, mouse and rat trkC (Lamballe et al., *Cell,* 66: 967–979 [1991]; EP 522,530 published 13 Jan. 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain). Human trk A, B and C receptor sequences are disclosed in U.S. Pat. application Ser. No. 08/215,139, filed Mar. 18, 1994, specifically incorporated herein by reference.

The following KIRA ELISA was performed using trk A, B and C receptor constructs having amino-terminal flag polypeptides.

41

(i) Capture agent preparation

Monoclonal anti-gD (clone 5B6) was produced against a peptide from Herpes simples virus glycoprotein D as discussed above in Example 2. The purified stock preparation was adjusted to 3.0 mg/ml in phosphate buffered saline (PBS), pH 7.4 and 1.0 ml aliquots were stored at −20° C.

(ii) Anti-phoshotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligands

Nerve growth factor (NGF), neurotrophin 3 (NT3), and neurotrophin 5 (NT5) were prepared by recombinant techniques using the sequence data provided for each of these proteins in the above-mentioned references. The purified NGF, NT3 and NT5 were stored at 4° C. as stock solutions (180 $\mu$M, 8.8 $\mu$M and 26.9 $\mu$M, respectively) in PBS, pH 7.5.

(iv) Preparation of gD.trk nucleic acid

In order to express the various trk receptors with gD flags (i.e. gD.trk constructs), DNA constructs were made which encoded the signal and epitope of gD (see Paborsky et al., supra) fused to the amino terminus of the various trk receptors. These were made by inserting the trk receptor and gD sequences into pRK5 or pRK7 (Suva et al., *Science*, 237: 893–896 [1987]) using standard molecular biology techniques, to generate the constructs shown in FIGS. 12–14. In addition to the gD.trk constructs, constructs were also made to express gD tagged trk.IgG fusion proteins (i.e., gD.trk.IgG). DNA constructs encoding the chimeras of trk extracellular domain and IgG-1 Fc domains were made with the Fc region clones of human IgG-1 (Ashkenazi et al., *Immunoadhesins Intern. Rev. Immunol.*, 10: 219–227 [1993]). More specifically, the source of the IgG-1 encoding sequence was the CD4-IgG-1 expression plasmid pRKCD4$_2$Fc$_1$ (Capon et al., *Nature*, 334: 525 [1989]; Byrn et al, *Nature*, 344: 667 [1990]) containing a cDNA sequence encoding a hybrid polypeptide consisting of residues 1–180 of the mature human CD4 protein fused to human IgG-1 sequences beginning at aspartic acid 216 (taking amino acid 114 as the first residue of the heavy chain constant region; Kabat et al, *Sequences of Proteins of Immunological Interest* 4th ed. [1987]), which is the first residue of the IgG-1 hinge after the cysteine residue involved in heavy-light chain bonding, and ending with residues 441 to include the CH2 and CH3 Fc domains of IgG-1. The CD4-encoding sequence was deleted from the expression plasmid pRKCD4$_2$Fc$_1$ and the vector was fused to DNA encoding the trk receptors, with the splice between aspartate 216 of the IgG-1 and valine 402 of trkA, threonine 422 of trkB, or threonine 413 of trkC. The gD tag was added to the amino terminus of each trk.lgG in the same way as for the gD.trk constructs.

(v) Cell transformation

Human embryonic kidney 293 cells (obtained from ATCC, Rockville, Md.) were transiently transfected with the nucleic acid encoding gD.trk.lgG using a calcium phosphate protocol (Gorman, *DNA Cloning: A Practical Approach* [Glover, D., ed.] Vol II: 143–190, IRL Press, Washington DC). After twelve hours, the transformed cells were rinsed three times with serum free F12/DMEM 50:50 media (Gibco) and then serum free media was added for a 48 hour collection.

Cell lines stably expressing each of the gD.trk constructs were made by co-transfecting dp 12.CHO cells (EP 307,247

42 published Mar. 15, 1989) with the pRK plasmids encoding the gD tagged trk receptors and a plasmid encoding DHFR, again using calcium phosphate mediated transfection.

The media mentioned above (having the gD.trk.IgG) was used without further purification in binding assays to assess the effects of the presence of the gD flag polypeptide on neurotrophin binding to the gD.trk.IgG polypeptides. DNA encoding untagged trk.IgG polypeptide was run in parallel as a control. trk.IgG and gD tagged trk.IgG containing cell supernatants were prepared as described and used in competitive displacement assays with the appropriate iodinated neurotrophin. NGF is used as ligand for trkA, NT5 is used as ligand for trkB, and NT3 is used as a ligand for trkC. A summary of the results obtained is shown in the following table.

TABLE 2

| | Binding of Neurotrophins to trk.IgG | |
|---|---|---|
| | IC50 without gD | IC50 with gD |
| trkA | 68.4 +/− 11.9 pM | 68.8 +/− 3.0 pM |
| trkB | 31.1 +/− 15.6 pM | 12.1 +/− 18 pM |
| trkC | 31.1 +/− 1.1 pM | 30.2 +/− 0.7 pM |

(vi) Selection of transformed cells for use in the KIRA ELISA

It was apparent from the preceding experiment that there was no observable change in the affinity of interaction of neurotrophins with their receptor due to the presence of the gD flag polypeptide on the amino terminus. Based on this result, cells were transformed with the gD.trk constructs for use in the KIRA ELISA using the techniques described in the previous section.

After two days, dp 12.CHO cells (EP 307,247 published Mar. 15, 1989) transformed with gD.trk constructs were selected for by growth in media without GHT, and after two weeks, growing cells were sorted by FACS analysis using the 5B6 monoclonal to select cells expressing the gD flag polypeptide on their surface. gD positive cells were cloned by plating at limiting dilution and resultant colonies were then rescreened by FACS analysis (using the anti-gD 5B6 monoclonal antibody), neurotrophin binding (as discussed above), tyrosine phosphorylation indicated by Western blot using an anti-phosphotyrosine antibody, gD expression by Western blot using th anti-gD 5B6 antibody, and immunocytochemistry using the 5B6 antibody. Clones which were positive were then recloned by limiting dilution and were subjected to the KIRA ELISA as described below.

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA gD.trk transformed dp 12.CHO cells (EP 307,247 published Mar. 15, 1989) were seeded (5×10$^4$ per well) in a flat-bottom-96 well culture plate in 100 $\mu$l media and cultured overnight at 37° C. in 5% CO$_2$, The following morning the well supernatants were decanted, and the plates were lightly tamped on a paper towel. 100 $\mu$l of media containing either experimental samples or the recombinant purified NGF, NT3, or NT5 standards (3000,1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate ($Na_3VO_4$; Sigma Chemical Co, St. Louis, Mo.). pH 7.5. The plate was then agitated gently on a plate shaker (Belico Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-gd 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized gD.trk from the cell-culture microtiter well was transferred (85 μl/well) to anti-gD 5B6 coated and blocked ELISA well and was incubated for 2 h at room temperature with gentle agitation. The unbound gD.trk was removed by washing with wash buffer and 100 μl of biotinylated 4G10 (anti-phosphotyrosine) diluted 1:2000 in dilution buffer (PBS containing 0.5 % BSA, 0.05% Tween-20, 5 mM EDTA, and 0.01% thimerosal), i.e., 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine; 2-component substrate kit; Kirkegeard and Perry, Gaithersburg, Md.) was added to each well. The reaction was allowed to proceed for 10 minutes, after which the color development was stopped by the addition of 100 μl/well 1.0M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curves shown in FIGS. 15A–15C were generated by stimulating gD.trk transformed CHO cells with 3000, 1000, 333, 111, 37, 12, 4, and 0 pM NGF, NT3 or NT5 and were presented as pM neurotrophin vs. mean $ABS_{450/650}$ ±sd using the DeltaSoft program. Sample concentrations were obtained by interpolation of their absorbance on the standard curve and are expressed in terms of pM neurotrophin activity.

The results presented in this example demonstrate that the KIRA ELISA is a useful method for assaying ligand activation of a receptor construct having an amino terminal flag polypeptide, e.g., activation of gD.trk receptor constructs. Levels of receptor activation in terms of tyrosine phosphorylation are easily quantified and an $EC_{50}$ for a given ligand is readily determined.

---

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 911 amino acids
        (B) TYPE: amino acid
        (D) TOPOLOGY: linear (xi) SEQUENCE DESCRIPTION: SEQ ID NO:1:

```
Met Ala Leu Arg Arg Ser Met Gly Arg Pro Gly Leu Pro Pro Leu
 1               5                  10                  15

Pro Leu Pro Pro Pro Arg Leu Gly Leu Leu Leu Ala Ala Leu
                20                  25                  30

Ala Ser Leu Leu Leu Pro Glu Ser Ala Ala Gly Leu Lys Leu
                35                  40                  45

Met Gly Ala Pro Val Lys Leu Thr Val Ser Gln Gly Gln Pro Val
                50                  55                  60

Lys Leu Asn Cys Ser Val Glu Gly Met Glu Glu Pro Asp Ile Gln
                65                  70                  75

Trp Val Lys Asp Gly Ala Val Val Gln Asn Leu Asp Gln Leu Tyr
                80                  85                  90

Ile Pro Val Ser Glu Gln His Trp Ile Gly Phe Leu Ser Leu Lys
                95                 100                 105

Ser Val Glu Arg Ser Asp Ala Gly Arg Tyr Trp Cys Gln Val Glu
```

-continued

```
                 110                 115                 120
Asp Gly Gly Glu Thr Glu Ile Ser Gln Pro Val Trp Leu Thr Val
                 125                 130                 135
Glu Gly Val Pro Phe Phe Thr Val Glu Pro Lys Asp Leu Ala Val
                 140                 145                 150
Pro Pro Asn Ala Pro Phe Gln Leu Ser Cys Glu Ala Val Gly Pro
                 155                 160                 165
Pro Glu Pro Val Thr Ile Val Trp Trp Arg Gly Thr Thr Lys Ile
                 170                 175                 180
Gly Gly Pro Ala Pro Ser Pro Ser Val Leu Asn Val Thr Gly Val
                 185                 190                 195
Thr Gln Ser Thr Met Phe Ser Cys Glu Ala His Asn Leu Lys Gly
                 200                 205                 210
Leu Ala Ser Ser Arg Thr Ala Thr Val His Leu Gln Ala Leu Pro
                 215                 220                 225
Ala Ala Pro Phe Asn Ile Thr Val Thr Lys Leu Ser Ser Ser Asn
                 230                 235                 240
Ala Ser Val Ala Trp Met Pro Gly Ala Asp Gly Arg Ala Leu Leu
                 245                 250                 255
Gln Ser Cys Thr Val Gln Val Thr Gln Ala Pro Gly Gly Trp Glu
                 260                 265                 270
Val Leu Ala Val Val Pro Val Pro Phe Thr Cys Leu Leu
                 275                 280                 285
Arg Asp Leu Val Pro Ala Thr Asn Tyr Ser Leu Arg Val Arg Cys
                 290                 295                 300
Ala Asn Ala Leu Gly Pro Ser Pro Tyr Ala Asp Trp Val Pro Phe
                 305                 310                 315
Gln Thr Lys Gly Leu Ala Pro Ala Ser Ala Pro Gln Asn Leu His
                 320                 325                 330
Ala Ile Arg Thr Asp Ser Gly Leu Ile Leu Glu Trp Glu Glu Val
                 335                 340                 345
Ile Pro Glu Ala Pro Leu Glu Gly Pro Leu Gly Pro Tyr Lys Leu
                 350                 355                 360
Ser Trp Val Gln Asp Asn Gly Thr Gln Asp Glu Leu Thr Val Glu
                 365                 370                 375
Gly Thr Arg Ala Asn Leu Thr Gly Trp Asp Pro Gln Lys Asp Leu
                 380                 385                 390
Ile Val Arg Val Cys Val Ser Asn Ala Val Gly Cys Gly Pro Trp
                 395                 400                 405
Ser Gln Pro Leu Val Val Ser Ser His Asp Arg Ala Gly Gln Gln
                 410                 415                 420
Gly Pro Pro His Ser Arg Thr Ser Trp Val Pro Val Val Leu Gly
                 425                 430                 435
Val Leu Thr Ala Leu Val Thr Ala Ala Leu Ala Leu Ile Leu
                 440                 445                 450
Leu Arg Lys Arg Arg Lys Glu Thr Arg Phe Gly Gln Ala Phe Asp
                 455                 460                 465
Ser Val Met Ala Arg Gly Glu Pro Val His Phe Arg Ala Ala
                 470                 475                 480
Arg Ser Phe Asn Arg Glu Arg Pro Glu Arg Ile Glu Ala Thr Leu
                 485                 490                 495
Asp Ser Leu Gly Ile Ser Asp Glu Leu Lys Glu Lys Leu Glu Asp
                 500                 505                 510
```

-continued

```
Val Leu Ile Pro Glu Gln Gln Phe Thr Leu Gly Arg Met Leu Gly
            515                 520                 525

Lys Gly Glu Phe Gly Ser Val Arg Glu Ala Gln Leu Lys Gln Glu
            530                 535                 540

Asp Gly Ser Phe Val Lys Val Ala Val Lys Met Leu Lys Ala Asp
            545                 550                 555

Ile Ile Ala Ser Ser Asp Ile Glu Glu Phe Leu Arg Glu Ala Ala
            560                 565                 570

Cys Met Lys Glu Phe Asp His Pro His Val Ala Lys Leu Val Gly
            575                 580                 585

Val Ser Leu Arg Ser Arg Ala Lys Gly Arg Leu Pro Ile Pro Met
            590                 595                 600

Val Ile Leu Pro Phe Met Lys His Gly Asp Leu His Ala Phe Leu
            605                 610                 615

Leu Ala Ser Arg Ile Gly Glu Asn Pro Phe Asn Leu Pro Leu Gln
            620                 625                 630

Thr Leu Ile Arg Phe Met Val Asp Ile Ala Cys Gly Met Glu Tyr
            635                 640                 645

Leu Ser Ser Arg Asn Phe Ile His Arg Asp Leu Ala Ala Arg Asn
            650                 655                 660

Cys Met Leu Ala Glu Asp Met Thr Val Cys Val Ala Asp Phe Gly
            665                 670                 675

Leu Ser Arg Lys Ile Tyr Ser Gly Asp Tyr Tyr Arg Gln Gly Cys
            680                 685                 690

Ala Ser Lys Leu Pro Val Lys Trp Leu Ala Leu Glu Ser Leu Ala
            695                 700                 705

Asp Asn Leu Tyr Thr Val Gln Ser Asp Val Trp Ala Phe Gly Val
            710                 715                 720

Thr Met Trp Glu Ile Met Thr Arg Gly Gln Thr Pro Tyr Ala Gly
            725                 730                 735

Ile Glu Asn Ala Glu Ile Tyr Asn Tyr Leu Ile Gly Gly Asn Arg
            740                 745                 750

Leu Lys Gln Pro Pro Glu Cys Met Glu Asp Val Tyr Asp Leu Met
            755                 760                 765

Tyr Gln Cys Trp Ser Ala Asp Pro Lys Gln Arg Pro Ser Phe Thr
            770                 775                 780

Cys Leu Arg Met Glu Leu Glu Asn Ile Leu Gly Gln Leu Ser Val
            785                 790                 795

Leu Ser Ala Ser Gln Asp Pro Leu Tyr Ile Asn Ile Glu Arg Ala
            800                 805                 810

Glu Glu Pro Thr Ala Gly Gly Ser Leu Glu Leu Pro Gly Arg Asp
            815                 820                 825

Gln Pro Tyr Ser Gly Ala Gly Asp Gly Ser Gly Met Gly Ala Val
            830                 835                 840

Gly Gly Thr Pro Ser Asp Cys Arg Tyr Ile Leu Thr Pro Gly Gly
            845                 850                 855

Leu Ala Glu Gln Pro Gly Gln Ala Glu His Gln Pro Glu Ser Pro
            860                 865                 870

Leu Asn Glu Thr Gln Arg Leu Leu Leu Leu Gln Gln Gly Leu Leu
            875                 880                 885

Pro His Ser Ser Cys Ala Asp Ala Ser Leu Lys Met Ala Asp Pro
            890                 895                 900

Asn Arg Phe Arg Gly Lys Asp Leu Pro Val Leu
            905                 910 911
```

(2) INFORMATION FOR SEQ ID NO:2:

(i) SEQUENCE CHARACTERISTICS:
        (A) LENGTH: 2742 bases
        (B) TYPE: nucleic acid
        (C) STRANDEDNESS: single
        (D) TOPOLOGY: linear (xi) SEQUENCE DESCRIPTION: SEQ ID NO:2:

```
ATGGCGCTGA GGCGGAGCAT GGGGCGGCCG GGGCTCCCGC CGCTGCCGCT            50

GCCGCCGCCA CCGCGGCTCG GGCTGCTGCT GGCGGCTCTG GCTTCTCTGC           100

TGCTCCCGGA GTCCGCCGCC GCAGGTCTGA AGCTCATGGG AGCCCCGGTG           150

AAGCTGACAG TGTCTCAGGG GCAGCCGGTG AAGCTCAACT GCAGTGTGGA           200

GGGGATGGAG GAGCCTGACA TCCAGTGGGT GAAGGATGGG GCTGTGGTCC           250

AGAACTTGGA CCAGTTGTAC ATCCCAGTCA GCGAGCAGCA CTGGATCGGC           300

TTCCTCAGCC TGAAGTCAGT GGAGCGCTCT GACGCCGGCC GGTACTGGTG           350

CCAGGTGGAG GATGGGGGTG AAACCGAGAT CTCCCAGCCA GTGTGGCTCA           400

CGGTAGAAGG TGTGCCATTT TTCACAGTGG AGCCAAAAGA TCTGGCAGTG           450

CCACCCAATG CCCCTTTCCA ACTGTCTTGT GAGGCTGTGG GTCCCCCTGA           500

ACCTGTTACC ATTGTCTGGT GGAGAGGAAC TACGAAGATC GGGGGACCCG           550

CTCCCTCTCC ATCTGTTTTA AATGTAACAG GGTGACCCA GAGCACCATG            600

TTTTCCTGTG AAGCTCACAA CCTAAAAGGC CTGGCCTCTT CTCGCACAGC           650

CACTGTTCAC CTTCAAGCAC TGCCTGCAGC CCCCTTCAAC ATCACCGTGA           700

CAAAGCTTTC CAGCAGCAAC GCTAGTGTGG CCTGGATGCC AGGTGCTGAT           750

GGCCGAGCTC TGCTACAGTC CTGTACAGTT CAGGTGACAC AGGCCCCAGG           800

AGGCTGGGAA GTCCTGGCTG TTGTGGTCCC TGTGCCCCCC TTTACCTGCC           850

TGCTCCGGGA CCTGGTGCCT GCCACCAACT ACAGCCTCAG GGTGCGCTGT           900

GCCAATGCCT TGGGGCCCTC TCCCTATGCT GACTGGGTGC CCTTTCAGAC           950

CAAGGGTCTA GCCCCAGCCA GCGCTCCCCA AAACCTCCAT GCCATCCGCA          1000

CAGATTCAGG CCTCATCTTG GAGTGGGAAG AAGTGATCCC CGAGGCCCCT          1050

TTGGAAGGCC CCCTGGGACC CTACAAACTG TCCTGGGTTC AAGACAATGG          1100

AACCCAGGAT GAGCTGACAG TGGAGGGGAC CAGGGCCAAT TTGACAGGCT          1150

GGGATCCCCA AAAGGACCTG ATCGTACGTG TGTGCGTCTC CAATGCAGTT          1200

GGCTGTGGAC CCTGGAGTCA GCCACTGGTG GTCTCTTCTC ATGACCGTGC          1250

AGGCCAGCAG GGCCCTCCTC ACAGCCGCAC ATCCTGGGTA CCTGTGGTCC          1300

TTGGTGTGCT AACGGCCCTG GTGACGGCTG CTGCCCTGGC CCTCATCCTG          1350

CTTCGAAAGA GACGGAAAGA GACGCGGTTT GGGCAAGCCT TTGACAGTGT          1400

CATGGCCCGG GGAGAGCCAG CCGTTCACTT CCGGGCAGCC CGGTCCTTCA          1450

ATCGAGAAAG GCCCGAGCGC ATCGAGGCCA CATTGGACAG CTTGGGCATC          1500

AGCGATGAAC TAAAGGAAAA ACTGGAGGAT GTGCTCATCC AGAGCAGCA           1550

GTTCACCCTG GGCCGGATGT TGGGCAAAGG AGAGTTTGGT TCAGTGCGGG          1600

AGGCCCAGCT GAAGCAAGAG GATGGCTCCT TTGTGAAAGT GGCTGTGAAG          1650

ATGCTGAAAG CTGACATCAT TGCCTCAAGC GACATTGAAG AGTTCCTCAG          1700
```

-continued

```
GGAAGCAGCT TGCATGAAGG AGTTTGACCA TCCACACGTG GCCAAACTTG      1750

TTGGGGTAAG CCTCCGGAGC AGGGCTAAAG GCCGTCTCCC CATCCCCATG      1800

GTCATCTTGC CCTTCATGAA GCATGGGGAC CTGCATGCCT TCCTGCTCGC      1850

CTCCCGGATT GGGGAGAACC CCTTTAACCT ACCCCTCCAG ACCCTGATCC      1900

GGTTCATGGT GGACATTGCC TGCGGCATGG AGTACCTGAG CTCTCGGAAC      1950

TTCATCCACC GAGACCTGGC TGCTCGGAAT TGCATGCTGG CAGAGGACAT      2000

GACAGTGTGT GTGGCTGACT TCGGACTCTC CCGGAAGATC TACAGTGGGG      2050

ACTACTATCG TCAAGGCTGT GCCTCCAAAC TGCCTGTCAA GTGGCTGGCC      2100

CTGGAGAGCC TGGCCGACAA CCTGTATACT GTGCAGAGTG ACGTGTGGGC      2150

GTTCGGGGTG ACCATGTGGG AGATCATGAC ACGTGGGCAG ACGCCATATG      2200

CTGGCATCGA AAACGCTGAG ATTTACAACT ACCTCATTGG CGGGAACCGC      2250

CTGAAACAGC CTCCGGAGTG TATGGAGGAC GTGTATGATC TCATGTACCA      2300

GTGCTGGAGT GCTGACCCCA AGCAGCGCCC GAGCTTTACT TGTCTGCGAA      2350

TGGAACTGGA GAACATCTTG GGCCAGCTGT CTGTGCTATC TGCCAGCCAG      2400

GACCCCTTAT ACATCAACAT CGAGAGAGCT GAGGAGCCCA CTGCGGGAGG      2450

CAGCCTGGAG CTACCTGGCA GGGATCAGCC CTACAGTGGG CTGGGGATG       2500

GCAGTGGCAT GGGGCAGTG GGTGGCACTC CCAGTGACTG TCGGTACATA       2550

CTCACCCCCG GAGGGCTGGC TGAGCAGCCA GGGCAGGCAG AGCACCAGCC      2600

AGAGAGTCCC CTCAATGAGA CACAGAGGCT TTTGCTGCTG CAGCAAGGGC      2650

TACTGCCACA CTCGAGCTGC GCAGATGCTA GCCTCAAGAT GGCTGATCCA      2700

AATCGATTCC GCGGCAAAGA TCTTCCGGTC CTGTAGAAGC TT              2742
```

(2) INFORMATION FOR SEQ ID NO:3:

(i) SEQUENCE CHARACTERISTICS:
        (A) LENGTH: 814 amino acids
        (B) TYPE: amino acid
        (D) TOPOLOGY: linear (xi) SEQUENCE DESCRIPTION: SEQ ID NO:3:

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Val Ala Ala Pro Cys
                50                  55                  60

Pro Asp Ala Cys Cys Pro His Gly Ser Ser Gly Leu Arg Cys Thr
                65                  70                  75

Arg Asp Gly Ala Leu Asp Ser Leu His His Leu Pro Gly Ala Glu
                80                  85                  90

Asn Leu Thr Glu Leu Tyr Ile Glu Asn Gln Gln His Leu Gln His
                95                  100                 105

Leu Glu Leu Arg Asp Leu Arg Gly Leu Gly Glu Leu Arg Asn Leu
                110                 115                 120

Thr Ile Val Lys Ser Gly Leu Arg Phe Val Ala Pro Asp Ala Phe
                125                 130                 135

His Phe Thr Pro Arg Leu Ser Arg Leu Asn Leu Ser Phe Asn Ala
```

```
                    140                 145                 150
Leu Glu Ser Leu Ser Trp Lys Thr Val Gln Gly Leu Ser Leu Gln
                    155                 160                 165
Glu Leu Val Leu Ser Gly Asn Pro Leu His Cys Ser Cys Ala Leu
                    170                 175                 180
Arg Trp Leu Gln Arg Trp Glu Glu Glu Gly Leu Gly Gly Val Pro
                    185                 190                 195
Glu Gln Lys Leu Gln Cys His Gly Gln Gly Pro Leu Ala His Met
                    200                 205                 210
Pro Asn Ala Ser Cys Gly Val Pro Thr Leu Lys Val Gln Val Pro
                    215                 220                 225
Asn Ala Ser Val Asp Val Gly Asp Asp Val Leu Leu Arg Cys Gln
                    230                 235                 240
Val Glu Gly Arg Gly Leu Glu Gln Ala Gly Trp Ile Leu Thr Glu
                    245                 250                 255
Leu Glu Gln Ser Ala Thr Val Met Lys Ser Gly Gly Leu Pro Ser
                    260                 265                 270
Leu Gly Leu Thr Leu Ala Asn Val Thr Ser Asp Leu Asn Arg Lys
                    275                 280                 285
Asn Leu Thr Cys Trp Ala Glu Asn Asp Val Gly Arg Ala Glu Val
                    290                 295                 300
Ser Val Gln Val Asn Val Ser Phe Pro Ala Ser Val Gln Leu His
                    305                 310                 315
Thr Ala Val Glu Met His His Trp Cys Ile Pro Phe Ser Val Asp
                    320                 325                 330
Gly Gln Pro Ala Pro Ser Leu Arg Trp Leu Phe Asn Gly Ser Val
                    335                 340                 345
Leu Asn Glu Thr Ser Phe Ile Phe Thr Glu Phe Leu Glu Pro Ala
                    350                 355                 360
Ala Asn Glu Thr Val Arg His Gly Cys Leu Arg Leu Asn Gln Pro
                    365                 370                 375
Thr His Val Asn Asn Gly Asn Tyr Thr Leu Leu Ala Ala Asn Pro
                    380                 385                 390
Phe Gly Gln Ala Ser Ala Ser Ile Met Ala Ala Phe Met Asp Asn
                    395                 400                 405
Pro Phe Glu Phe Asn Pro Glu Asp Pro Ile Pro Asp Thr Asn Ser
                    410                 415                 420
Thr Ser Gly Asp Pro Val Glu Lys Lys Asp Glu Thr Pro Phe Gly
                    425                 430                 435
Val Ser Val Ala Val Gly Leu Ala Val Phe Ala Cys Leu Phe Leu
                    440                 445                 450
Ser Thr Leu Leu Leu Val Leu Asn Lys Cys Gly Arg Arg Asn Lys
                    455                 460                 465
Phe Gly Ile Asn Arg Pro Ala Val Leu Ala Pro Glu Asp Gly Leu
                    470                 475                 480
Ala Met Ser Leu His Phe Met Thr Leu Gly Gly Ser Ser Leu Ser
                    485                 490                 495
Pro Thr Glu Gly Lys Gly Ser Gly Leu Gln Gly His Ile Ile Glu
                    500                 505                 510
Asn Pro Gln Tyr Phe Ser Asp Ala Cys Val His His Ile Lys Arg
                    515                 520                 525
Arg Asp Ile Val Leu Lys Trp Glu Leu Gly Glu Gly Ala Phe Gly
                    530                 535                 540
```

```
Lys Val Phe Leu Ala Glu Cys His Asn Leu Leu Pro Glu Gln Asp
                545                 550                 555

Lys Met Leu Val Ala Val Lys Ala Leu Lys Glu Ala Ser Glu Ser
                560                 565                 570

Ala Arg Gln Asp Phe Gln Arg Glu Ala Glu Leu Leu Thr Met Leu
                575                 580                 585

Gln His Gln His Ile Val Arg Phe Phe Gly Val Cys Thr Glu Gly
                590                 595                 600

Arg Pro Leu Leu Met Val Phe Glu Tyr Met Arg His Gly Asp Leu
                605                 610                 615

Asn Arg Phe Leu Arg Ser His Gly Pro Asp Ala Lys Leu Leu Ala
                620                 625                 630

Gly Gly Glu Asp Val Ala Pro Gly Pro Leu Gly Leu Gly Gln Leu
                635                 640                 645

Leu Ala Val Ala Ser Gln Val Ala Ala Gly Met Val Tyr Leu Ala
                650                 655                 660

Gly Leu His Phe Val His Arg Asp Leu Ala Thr Arg Asn Cys Leu
                665                 670                 675

Val Gly Gln Gly Leu Val Val Lys Ile Gly Asp Phe Gly Met Ser
                680                 685                 690

Arg Asp Ile Tyr Ser Thr Asp Tyr Tyr Arg Val Gly Gly Arg Thr
                695                 700                 705

Met Leu Pro Ile Arg Trp Met Pro Pro Glu Ser Ile Leu Tyr Arg
                710                 715                 720

Lys Phe Thr Thr Glu Ser Asp Val Trp Ser Phe Gly Val Val Leu
                725                 730                 735

Trp Glu Ile Phe Thr Tyr Gly Lys Gln Pro Trp Tyr Gln Leu Ser
                740                 745                 750

Asn Thr Glu Ala Ile Asp Cys Ile Thr Gln Gly Arg Glu Leu Glu
                755                 760                 765

Arg Pro Arg Ala Cys Pro Pro Glu Val Tyr Ala Ile Met Arg Gly
                770                 775                 780

Cys Trp Gln Arg Glu Pro Gln Gln Arg His Ser Ile Lys Asp Val
                785                 790                 795

His Ala Arg Leu Gln Ala Leu Ala Gln Ala Pro Pro Val Tyr Leu
                800                 805                 810

Asp Val Leu Gly
       814

(2) INFORMATION FOR SEQ ID NO:4:

(i) SEQUENCE CHARACTERISTICS:
        (A) LENGTH: 2820 bases
        (B) TYPE: nucleic acid
        (C) STRANDEDNESS: double
        (D) TOPOLOGY: linear (xi) SEQUENCE DESCRIPTION: SEQ ID NO:4:

TATAGAATAA CATCCACTTT GCCTTTCTCT CCACAGGTGT CCACTCCCAG           50

GTCCAACTGC ACCTGAATTC CACTGCCTTC CACCAAGCTC TGCAGGATCC          100

CAGAGTCAGG GGTCTGTATC TTCCTGCTGG TGGCTCCAGT TCAGGAACAG          150

TAAACCCTGC TCCGAATATT GCCTCTCACA TCTCGTCAAT CTCCGCGAGG          200

ACTGGGGACC CTGTGACAAG CTTCAGCGCG AACGACCAAC TACCCCGATC          250

ATCAGTTATC CTTAAGGTCT CTTTTGTGTG GTGCGTTCCG GTATGGGGGG          300
```

-continued

| | |
|---|---|
| GACTGCCGCC AGGTTGGGGG CCGTGATTTT GTTTGTCGTC ATAGTGGGCC | 350 |
| TCCATGGGGT CCGCGGCAAA TATGCCTTGG CGGATGCCTC TCTCAAGATG | 400 |
| GCCGACCCCA ATCGATTTCG CGGCAAAGAC CTTCCGGTCC TGGACCAGCT | 450 |
| GCTCGAGGTA GCCGCACCCT GCCCCGATGC CTGCTGCCCC CACGGCTCCT | 500 |
| CGGGACTGCG ATGCACCCGG GATGGGCCC TGGATAGCCT CCACCACCTG | 550 |
| CCCGGCGCAG AGAACCTGAC TGAGCTCTAC ATCGAGAACC AGCAGCATCT | 600 |
| GCAGCATCTG GAGCTCCGTG ATCTGAGGGG CCTGGGGGAG CTGAGAAACC | 650 |
| TCACCATCGT GAAGAGTGGT CTCCGTTTCG TGGCGCCAGA TGCCTTCCAT | 700 |
| TTCACTCCTC GGCTCAGTCG CCTGAATCTC TCCTTCAACG CTCTGGAGTC | 750 |
| TCTCTCCTGG AAAACTGTGC AGGGCCTCTC CTTACAGGAA CTGGTCCTGT | 800 |
| CGGGGAACCC TCTGCACTGT TCTTGTGCCC TGCGCTGGCT ACAGCGCTGG | 850 |
| GAGGAGGAGG GACTGGGCGG AGTGCCTGAA CAGAAGCTGC AGTGTCATGG | 900 |
| GCAAGGGCCC CTGGCCCACA TGCCCAATGC CAGCTGTGGT GTGCCCACGC | 950 |
| TGAAGGTCCA GGTGCCCAAT GCCTCGGTGG ATGTGGGGGA CGACGTGCTG | 1000 |
| CTGCGGTGCC AGGTGGAGGG GCGGGGCCTG GAGCAGGCCG GCTGGATCCT | 1050 |
| CACAGAGCTG GAGCAGTCAG CCACGGTGAT GAAATCTGGG GGTCTGCCAT | 1100 |
| CCCTGGGGCT GACCCTGGCC AATGTCACCA GTGACCTCAA CAGGAAGAAC | 1150 |
| TTGACGTGCT GGGCAGAGAA CGATGTGGGC CGGGCAGAGG TCTCTGTTCA | 1200 |
| GGTCAACGTC TCCTTCCCGG CCAGTGTGCA GCTGCACACG GCGGTGGAGA | 1250 |
| TGCACCACTG GTGCATCCCC TTCTCTGTGG ATGGGCAGCC GGCACCGTCT | 1300 |
| CTGCGCTGGC TCTTCAATGG CTCCGTGCTC AATGAGACCA GCTTCATCTT | 1350 |
| CACTGAGTTC CTGGAGCCGG CAGCCAATGA GACCGTGCGG CACGGGTGTC | 1400 |
| TGCGCCTCAA CCAGCCCACC CACGTCAACA ACGGCAACTA CACGCTGCTG | 1450 |
| GCTGCCAACC CCTTCGGCCA GGCCTCCGCC TCCATCATGG CTGCCTTCAT | 1500 |
| GGACAACCCT TTCGAGTTCA ACCCCGAGGA CCCCATCCCT GACACTAACA | 1550 |
| GCACATCTGG AGACCCGGTG GAGAAGAAGG ACGAAACACC TTTTGGGGTC | 1600 |
| TCGGTGGCTG TGGGCCTGGC CGTCTTTGCC TGCCTCTTCC TTTCTACGCT | 1650 |
| GCTCCTTGTG CTCAACAAAT GTGGACGGAG AAACAAGTTT GGGATCAACC | 1700 |
| GCCCGGCTGT GCTGGCTCCA GAGGATGGGC TGGCCATGTC CCTGCATTTC | 1750 |
| ATGACATTGG GTGGCAGCTC CCTGTCCCCC ACCGAGGGCA AAGGCTCTGG | 1800 |
| GCTCCAAGGC CACATCATCG AGAACCCACA ATACTTCAGT GATGCCTGTG | 1850 |
| TTCACCACAT CAAGCGCCGG GACATCGTGC TCAAGTGGGA GCTGGGGGAG | 1900 |
| GGCGCCTTTG GGAAGGTCTT CCTTGCTGAG TGCCACAACC TCCTGCCTGA | 1950 |
| GCAGGACAAG ATGCTGGTGG CTGTCAAGGC ACTGAAGGAG GCGTCCGAGA | 2000 |
| GTGCTCGGCA GGACTTCCAA CGTGAGGCTG AGCTGCTCAC CATGCTGCAG | 2050 |
| CACCAGCACA TCGTGCGCTT CTTCGGCGTC TGCACCGAGG GCCGCCCCCT | 2100 |
| GCTCATGGTC TTTGAGTATA TGCGGCACGG GGACCTCAAC CGCTTCCTCC | 2150 |
| GATCCCATGG ACCTGATGCC AAGCTGCTGG CTGGTGGGGA GGATGTGGCT | 2200 |
| CCAGGCCCCC TGGGTCTGGG GCAGCTGCTG GCCGTGGCTA GCCAGGTCGC | 2250 |
| TGCGGGGATG GTGTACCTGG CGGGTCTGCA TTTTGTGCAC CGGGACCTGG | 2300 |

```
CCACACGCAA CTGTCTAGTG GGCCAGGGAC TGGTGGTCAA GATTGGTGAT              2350

TTTGGCATGA GCAGGGATAT CTACAGCACC GACTATTACC GTGTGGGAGG              2400

CCGCACCATG CTGCCCATTC GCTGGATGCC GCCCGAGAGC ATCCTGTACC              2450

GTAAGTTCAC CACCGAGAGC GACGTGTGGA GCTTCGGCGT GGTGCTCTGG              2500

GAGATCTTCA CCTACGGCAA GCAGCCCTGG TACCAGCTCT CCAACACGGA              2550

GGCAATCGAC TGCATCACGC AGGGACGTGA GTTGGAGCGG CCACGTGCCT              2600

GCCCACCAGA GGTCTACGCC ATCATGCGGG GCTGCTGGCA GCGGGAGCCC              2650

CAGCAACGCC ACAGCATCAA GGATGTGCAC GCCCGGCTGC AAGCCCTGGC              2700

CCAGGCACCT CCTGTCTACC TGGATGTCCT GGGCTAGAAT TAATTCAATC              2750

GATGGCCGCC ATGGCCCAAC TTGTTTATTG CAGCTTATAA TGGTTACAAA              2800

TAAAGCAATA GCATCACAAA                                               2820
```

(2) INFORMATION FOR SEQ ID NO:5:

(i) SEQUENCE CHARACTERISTICS:
        (A) LENGTH: 847 amino acids
        (B) TYPE: amino acid
        (D) TOPOLOGY: linear (xi) SEQUENCE DESCRIPTION: SEQ ID NO:5:

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Val Cys Pro Thr Ser
                50                  55                  60

Cys Lys Cys Ser Ala Ser Arg Ile Trp Cys Ser Asp Pro Ser Pro
                65                  70                  75

Gly Ile Val Ala Phe Pro Arg Leu Glu Pro Asn Ser Val Asp Pro
                80                  85                  90

Glu Asn Ile Thr Glu Ile Phe Ile Ala Asn Gln Lys Arg Leu Glu
                95                 100                 105

Ile Ile Asn Glu Asp Asp Val Glu Ala Tyr Val Gly Leu Arg Asn
               110                 115                 120

Leu Thr Ile Val Asp Ser Gly Leu Lys Phe Val Ala His Lys Ala
               125                 130                 135

Phe Leu Lys Asn Ser Asn Leu Gln His Ile Asn Phe Thr Arg Asn
               140                 145                 150

Lys Leu Thr Ser Leu Ser Arg Lys His Phe Arg His Leu Asp Leu
               155                 160                 165

Ser Glu Leu Ile Leu Val Gly Asn Pro Phe Thr Cys Ser Cys Asp
               170                 175                 180

Ile Met Trp Ile Lys Thr Leu Gln Glu Ala Lys Ser Ser Pro Asp
               185                 190                 195

Thr Gln Asp Leu Tyr Cys Leu Asn Glu Ser Ser Lys Asn Ile Pro
               200                 205                 210

Leu Ala Asn Leu Gln Ile Pro Asn Cys Gly Leu Pro Ser Ala Asn
               215                 220                 225

Leu Ala Ala Pro Asn Leu Thr Val Glu Gly Lys Ser Ile Thr
               230                 235                 240
```

```
Leu Ser Cys Ser Val Ala Gly Asp Pro Val Pro Asn Met Tyr Trp
            245                 250                 255

Asp Val Gly Asn Leu Val Ser Lys His Met Asn Glu Thr Ser His
            260                 265                 270

Thr Gln Gly Ser Leu Arg Ile Thr Asn Ile Ser Ser Asp Asp Ser
            275                 280                 285

Gly Lys Gln Ile Ser Cys Val Ala Glu Asn Leu Val Gly Glu Asp
            290                 295                 300

Gln Asp Ser Val Asn Leu Thr Val His Phe Ala Pro Thr Ile Thr
            305                 310                 315

Phe Leu Glu Ser Pro Thr Ser Asp His His Trp Cys Ile Pro Phe
            320                 325                 330

Thr Val Lys Gly Asn Pro Lys Pro Ala Leu Gln Trp Phe Tyr Asn
            335                 340                 345

Gly Ala Ile Leu Asn Glu Ser Lys Tyr Ile Cys Thr Lys Ile His
            350                 355                 360

Val Thr Asn His Thr Glu Tyr His Gly Cys Leu Gln Leu Asp Asn
            365                 370                 375

Pro Thr His Met Asn Asn Gly Asp Tyr Thr Leu Ile Ala Lys Asn
            380                 385                 390

Glu Tyr Gly Lys Asp Glu Lys Gln Ile Ser Ala His Phe Met Gly
            395                 400                 405

Trp Pro Gly Ile Asp Asp Gly Ala Asn Pro Asn Tyr Pro Asp Val
            410                 415                 420

Ile Tyr Glu Asp Tyr Gly Thr Ala Ala Asn Asp Ile Gly Asp Thr
            425                 430                 435

Thr Asn Arg Ser Asn Glu Ile Pro Ser Thr Asp Val Thr Asp Lys
            440                 445                 450

Thr Gly Arg Glu His Leu Ser Val Tyr Ala Val Val Val Ile Ala
            455                 460                 465

Ser Val Val Gly Phe Cys Leu Leu Val Met Leu Phe Leu Leu Lys
            470                 475                 480

Leu Ala Arg His Ser Lys Phe Gly Met Lys Gly Pro Ala Ser Val
            485                 490                 495

Ile Ser Asn Asp Asp Asp Ser Ala Ser Pro Leu His His Ile Ser
            500                 505                 510

Asn Gly Ser Asn Thr Pro Ser Ser Ser Glu Gly Gly Pro Asp Ala
            515                 520                 525

Val Ile Ile Gly Met Thr Lys Ile Pro Val Ile Glu Asn Pro Gln
            530                 535                 540

Tyr Phe Gly Ile Thr Asn Ser Gln Leu Lys Pro Asp Thr Phe Val
            545                 550                 555

Gln His Ile Lys Arg His Asn Ile Val Leu Lys Arg Glu Leu Gly
            560                 565                 570

Glu Gly Ala Phe Gly Lys Val Phe Leu Ala Glu Cys Tyr Asn Leu
            575                 580                 585

Cys Pro Glu Gln Asp Lys Ile Leu Val Ala Val Lys Thr Leu Lys
            590                 595                 600

Asp Ala Ser Asp Asn Ala Arg Lys Asp Phe His Arg Glu Ala Glu
            605                 610                 615

Leu Leu Thr Asn Leu Gln His Glu His Ile Val Lys Phe Tyr Gly
            620                 625                 630

Val Cys Val Glu Gly Asp Pro Leu Ile Met Val Phe Glu Tyr Met
            635                 640                 645
```

```
Lys His Gly Asp Leu Asn Lys Phe Leu Arg Ala His Gly Pro Asp
            650                 655                 660

Ala Val Leu Met Ala Glu Gly Asn Pro Pro Thr Glu Leu Thr Gln
            665                 670                 675

Ser Gln Met Leu His Ile Ala Gln Gln Ile Ala Ala Gly Met Val
            680                 685                 690

Tyr Leu Ala Ser Gln His Phe Val His Arg Asp Leu Ala Thr Arg
            695                 700                 705

Asn Cys Leu Val Gly Glu Asn Leu Leu Val Lys Ile Gly Asp Phe
            710                 715                 720

Gly Met Ser Arg Asp Val Tyr Ser Thr Asp Tyr Tyr Arg Val Gly
            725                 730                 735

Gly His Thr Met Leu Pro Ile Arg Trp Met Pro Pro Glu Ser Ile
            740                 745                 750

Met Tyr Arg Lys Phe Thr Thr Glu Ser Asp Val Trp Ser Leu Gly
            755                 760                 765

Val Val Leu Trp Glu Ile Phe Thr Tyr Gly Lys Gln Pro Trp Tyr
            770                 775                 780

Gln Leu Ser Asn Asn Glu Val Ile Glu Cys Ile Thr Gln Gly Arg
            785                 790                 795

Val Leu Gln Arg Pro Arg Thr Cys Pro Gln Glu Val Tyr Glu Leu
            800                 805                 810

Met Leu Gly Cys Trp Gln Arg Glu Pro His Met Arg Lys Asn Ile
            815                 820                 825

Lys Gly Ile His Thr Leu Leu Gln Asn Leu Ala Lys Ala Ser Pro
            830                 835                 840

Val Tyr Leu Asp Ile Leu Gly
            845     847

(2) INFORMATION FOR SEQ ID NO:6:

(i) SEQUENCE CHARACTERISTICS:
        (A) LENGTH: 3060 bases
        (B) TYPE: nucleic acid
        (C) STRANDEDNESS: double
        (D) TOPOLOGY: linear (xi) SEQUENCE DESCRIPTION: SEQ ID NO:6:

TATAGAATAA CATCCACTTT GCCTTTCTCT CCACAGGTGT CCACTCCCAG           50

GTCCAACTGC ACCTCGGTTC TATCGATTGA ATTCCACTGC CTTCCACCAA          100

GCTCTGCAGG ATCCCAGAGT CAGGGGTCTG TATCTTCCTG CTGGTGGCTC          150

CAGTTCAGGA ACAGTAAACC CTGCTCCGAA TATTGCCTCT CACATCTCGT          200

CAATCTCCGC GAGGACTGGG GACCCTGTGA CAAGCTTCAG CGCGAACGAC          250

CAACTACCCC GATCATCAGT TATCCTTAAG GTCTCTTTTG TGTGGTGCGT          300

TCCGGTATGG GGGGACTGC CGCCAGGTTG GGGGCCGTGA TTTTGTTTGT           350

CGTCATAGTG GGCCTCCATG GGTCCGCGG CAAATATGCC TTGGCGGATG           400

CCTCTCTCAA GATGGCCGAC CCCAATCGAT TTCGCGGCAA AGACCTTCCG          450

GTCCTGGACC AGCTGCTCGA GGTATGTCCC ACGTCCTGCA AATGCAGTGC          500

CTCTCGGATC TGGTGCAGCG ACCCTTCTCC TGGCATCGTG GCATTTCCGA          550

GATTGGAGCC TAACAGTGTA GATCCTGAGA CATCACCGA AATTTTCATC           600

GCAAACCAGA AAAGGTTAGA ATCATCAAC GAAGATGATG TTGAAGCTTA           650
```

```
TGTGGGACTG AGAAATCTGA CAATTGTGGA TTCTGGATTA AAATTTGTGG    700

CTCATAAAGC ATTTCTGAAA AACAGCAACC TGCAGCACAT CAATTTTACC    750

CGAAACAAAC TGACGAGTTT GTCTAGGAAA CATTTCCGTC ACCTTGACTT    800

GTCTGAACTG ATCCTGGTGG GCAATCCATT TACATGCTCC TGTGACATTA    850

TGTGGATCAA GACTCTCCAA GAGGCTAAAT CCAGTCCAGA CACTCAGGAT    900

TTGTACTGCC TGAATGAAAG CAGCAAGAAT ATTCCCCTGG CAAACCTGCA    950

GATACCCAAT TGTGGTTTGC CATCTGCAAA TCTGGCCGCA CCTAACCTCA    1000

CTGTGGAGGA AGGAAAGTCT ATCACATTAT CCTGTAGTGT GGCAGGTGAT    1050

CCGGTTCCTA ATATGTATTG GGATGTTGGT AACCTGGTTT CCAAACATAT    1100

GAATGAAACA AGCCACACAC AGGGCTCCTT AAGGATAACT AACATTTCAT    1150

CCGATGACAG TGGGAAGCAG ATCTCTTGTG TGGCGGAAAA TCTTGTAGGA    1200

GAAGATCAAG ATTCTGTCAA CCTCACTGTG CATTTTGCAC CAACTATCAC    1250

ATTTCTCGAA TCTCCAACCT CAGACCACCA CTGGTGCATT CCATTCACTG    1300

TGAAAGGCAA CCCAAAACCA GCGCTTCAGT GGTTCTATAA CGGGGCAATA    1350

TTGAATGAGT CCAAATACAT CTGTACTAAA ATACATGTTA CCAATCACAC    1400

GGAGTACCAC GGCTGCCTCC AGCTGGATAA TCCCACTCAC ATGAACAATG    1450

GGGACTACAC TCTAATAGCC AAGAATGAGT ATGGGAAGGA TGAGAAACAG    1500

ATTTCTGCTC ACTTCATGGG CTGGCCTGGA ATTGACGATG GTGCAAACCC    1550

AAATTATCCT GATGTAATTT ATGAAGATTA TGGAACTGCA GCGAATGACA    1600

TCGGGACAC CACGAACAGA AGTAATGAAA TCCCTTCCAC AGACGTCACT    1650

GATAAAACCG GTCGGAACA TCTCTCGGTC TATGCTGTGG TGGTGATTGC    1700

GTCTGTGGTG GGATTTTGCC TTTTGGTAAT GCTGTTTCTG CTTAAGTTGG    1750

CAAGACACTC CAAGTTTGGC ATGAAAGGCC CAGCCTCCGT TATCAGCAAT    1800

GATGATGACT CTGCCAGCCC ACTCCATCAC ATCTCCAATG GGAGTAACAC    1850

TCCATCTTCT TCGGAAGGTG GCCCAGATGC TGTCATTATT GGAATGACCA    1900

AGATCCCTGT CATTGAAAAT CCCCAGTACT TTGGCATCAC CAACAGTCAG    1950

CTCAAGCCAG ACACATTTGT TCAGCACATC AAGCGACATA ACATTGTTCT    2000

GAAAAGGGAG CTAGGCGAAG GAGCCTTTGG AAAAGTGTTC CTAGCTGAAT    2050

GCTATAACCT CTGTCCTGAG CAGGACAAGA TCTTGGTGGC AGTGAAGACC    2100

CTGAAGGATG CCAGTGACAA TGCACGCAAG GACTTCCACC GTGAGGCCGA    2150

GCTCCTGACC AACCTCCAGC ATGAGCACAT CGTCAAGTTC TATGGCGTCT    2200

GCGTGGAGGG CGACCCCCTC ATCATGGTCT TTGAGTACAT GAAGCATGGG    2250

GACCTCAACA AGTTCCTCAG GGCACACGGC CCTGATGCCG TGCTGATGGC    2300

TGAGGGCAAC CCGCCCACGG AACTGACGCA GTCGCAGATG CTGCATATAG    2350

CCCAGCAGAT CGCCGCGGGC ATGGTCTACC TGGCGTCCCA GCACTTCGTG    2400

CACCGCGATT TGGCCACCAG GAACTGCCTG GTCGGGGAGA ACTTGCTGGT    2450

GAAAATCGGG GACTTTGGGA TGTCCCGGGA CGTGTACAGC ACTGACTACT    2500

ACAGGGTCGG TGGCCACACA ATGCTGCCCA TTCGCTGGAT GCCTCCAGAG    2550

AGCATCATGT ACAGGAAATT CACGACGGAA AGCGACGTCT GGAGCCTGGG    2600

GGTCGTGTTG TGGGAGATTT TCACCTATGG CAAACAGCCC TGGTACCAGC    2650
```

-continued

```
TGTCAAACAA TGAGGTGATA GAGTGTATCA CTCAGGGCCG AGTCCTGCAG         2700

CGACCCCGCA CGTGCCCCCA GGAGGTGTAT GAGCTGATGC TGGGGTGCTG         2750

GCAGCGAGAG CCCCACATGA GGAAGAACAT CAAGGGCATC CATACCCTCC         2800

TTCAGAACTT GGCCAAGGCA TCTCCGGTCT ACCTGGACAT TCTAGGCTAG         2850

GGCCCTTTTC CCCAGACCGA TCCTTCCCAA CGTACTCCTC AGACGGGCTG         2900

AGAGGATGAA CATCTTTTAA CTGCCGCTGG AGGCCACCAA GCTGCTCTCC         2950

TTCACTCTGA CAGTATTAAC ATCAAAGACT CCGAGAAGCT CTCGACCTGC         3000

AGAAGCTTGG CCGCCATGGC CCAACTTGTT TATTGCAGCT TATAATGGTT         3050

ACAAATAAAG                                                     3060
```

(2) INFORMATION FOR SEQ ID NO:7:

(i) SEQUENCE CHARACTERISTICS:
        (A) LENGTH: 850 amino acids
        (B) TYPE: amino acid
        (D) TOPOLOGY: linear (xi) SEQUENCE DESCRIPTION: SEQ ID NO:7:

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Val Cys Pro Ala Asn
                50                  55                  60

Cys Val Cys Ser Lys Thr Glu Ile Asn Cys Arg Arg Pro Asp Asp
                65                  70                  75

Gly Asn Leu Phe Pro Leu Leu Glu Gly Gln Asp Ser Gly Asn Ser
                80                  85                  90

Asn Gly Asn Ala Asn Ile Asn Ile Thr Asp Ile Ser Arg Asn Ile
                95                 100                 105

Thr Ser Ile His Ile Glu Asn Trp Arg Ser Leu His Thr Leu Asn
               110                 115                 120

Ala Val Asp Met Glu Leu Tyr Thr Gly Leu Gln Lys Leu Thr Ile
               125                 130                 135

Lys Asn Ser Gly Leu Arg Ser Ile Gln Pro Arg Ala Phe Ala Lys
               140                 145                 150

Asn Pro His Leu Arg Tyr Ile Asn Leu Ser Ser Asn Arg Leu Thr
               155                 160                 165

Thr Leu Ser Trp Gln Leu Phe Gln Thr Leu Ser Leu Arg Glu Leu
               170                 175                 180

Gln Leu Glu Gln Asn Phe Phe Asn Cys Ser Cys Asp Ile Arg Trp
               185                 190                 195

Met Gln Leu Trp Gln Glu Gln Gly Glu Ala Lys Leu Asn Ser Gln
               200                 205                 210

Asn Leu Tyr Cys Ile Asn Ala Asp Gly Ser Gln Leu Pro Leu Phe
               215                 220                 225

Arg Met Asn Ile Ser Gln Cys Asp Leu Pro Glu Ile Ser Val Ser
               230                 235                 240

His Val Asn Leu Thr Val Arg Glu Gly Asp Asn Ala Val Ile Thr
               245                 250                 255

Cys Asn Gly Ser Gly Ser Pro Leu Pro Asp Val Asp Trp Ile Val
```

```
                    260                 265                 270
Thr Gly Leu Gln Ser Ile Asn Thr His Gln Thr Asn Leu Asn Trp
                275                 280                 285
Thr Asn Val His Ala Ile Asn Leu Thr Leu Val Asn Val Thr Ser
                290                 295                 300
Glu Asp Asn Gly Phe Thr Leu Thr Cys Ile Ala Glu Asn Val Val
                305                 310                 315
Gly Met Ser Asn Ala Ser Val Ala Leu Thr Val Tyr Tyr Pro Pro
                320                 325                 330
Arg Val Val Ser Leu Glu Glu Pro Glu Leu Arg Leu Glu His Cys
                335                 340                 345
Ile Glu Phe Val Val Arg Gly Asn Pro Pro Pro Thr Leu His Trp
                350                 355                 360
Leu His Asn Gly Gln Pro Leu Arg Glu Ser Lys Ile Ile His Val
                365                 370                 375
Glu Tyr Tyr Gln Glu Gly Glu Ile Ser Glu Gly Cys Leu Leu Phe
                380                 385                 390
Asn Lys Pro Thr His Tyr Asn Asn Gly Asn Tyr Thr Leu Ile Ala
                395                 400                 405
Lys Asn Pro Leu Gly Thr Ala Asn Gln Thr Ile Asn Gly His Phe
                410                 415                 420
Leu Lys Glu Pro Phe Pro Glu Ser Thr Asp Asn Phe Ile Leu Phe
                425                 430                 435
Asp Glu Val Ser Pro Thr Pro Pro Ile Thr Val Thr His Lys Pro
                440                 445                 450
Glu Glu Asp Thr Phe Gly Val Ser Ile Ala Val Gly Leu Ala Ala
                455                 460                 465
Phe Ala Cys Val Leu Leu Val Val Leu Phe Val Met Ile Asn Lys
                470                 475                 480
Tyr Gly Arg Arg Ser Lys Phe Gly Met Lys Gly Pro Val Ala Val
                485                 490                 495
Ile Ser Gly Glu Glu Asp Ser Ala Ser Pro Leu His His Ile Asn
                500                 505                 510
His Gly Ile Thr Thr Pro Ser Ser Leu Asp Ala Gly Pro Asp Thr
                515                 520                 525
Val Val Ile Gly Met Thr Arg Ile Pro Val Ile Glu Asn Pro Gln
                530                 535                 540
Tyr Phe Arg Gln Gly His Asn Cys His Lys Pro Asp Thr Tyr Val
                545                 550                 555
Gln His Ile Lys Arg Arg Asp Ile Val Leu Lys Arg Glu Leu Gly
                560                 565                 570
Glu Gly Ala Phe Gly Lys Val Phe Leu Ala Glu Cys Tyr Asn Leu
                575                 580                 585
Ser Pro Thr Lys Asp Lys Met Leu Val Ala Val Lys Ala Leu Lys
                590                 595                 600
Asp Pro Thr Leu Ala Ala Arg Lys Asp Phe Gln Arg Glu Ala Glu
                605                 610                 615
Leu Leu Thr Asn Leu Gln His Glu His Ile Val Lys Phe Tyr Gly
                620                 625                 630
Val Cys Gly Asp Gly Asp Pro Leu Ile Met Val Phe Glu Tyr Met
                635                 640                 645
Lys His Gly Asp Leu Asn Lys Phe Leu Arg Ala His Gly Pro Asp
                650                 655                 660
```

```
Ala Met Ile Leu Val Asp Gly Gln Pro Arg Gln Ala Lys Gly Glu
                665                 670                 675

Leu Gly Leu Ser Gln Met Leu His Ile Ala Ser Gln Ile Ala Ser
            680                 685                 690

Gly Met Val Tyr Leu Ala Ser Gln His Phe Val His Arg Asp Leu
        695                 700                 705

Ala Thr Arg Asn Cys Leu Val Gly Ala Asn Leu Leu Val Lys Ile
    710                 715                 720

Gly Asp Phe Gly Met Ser Arg Asp Val Tyr Ser Thr Asp Tyr Tyr
725                 730                 735

Arg Val Gly Gly His Thr Met Leu Pro Ile Arg Trp Met Pro Pro
                740                 745                 750

Glu Ser Ile Met Tyr Arg Lys Phe Thr Thr Glu Ser Asp Val Trp
            755                 760                 765

Ser Phe Gly Val Ile Leu Trp Glu Ile Phe Thr Tyr Gly Lys Gln
        770                 775                 780

Pro Trp Phe Gln Leu Ser Asn Thr Glu Val Ile Glu Cys Ile Thr
    785                 790                 795

Gln Gly Arg Val Leu Glu Arg Pro Arg Val Cys Pro Lys Glu Val
800                 805                 810

Tyr Asp Val Met Leu Gly Cys Trp Gln Arg Glu Pro Gln Gln Arg
                815                 820                 825

Leu Asn Ile Lys Glu Ile Tyr Lys Ile Leu His Ala Leu Gly Lys
            830                 835                 840

Ala Thr Pro Ile Tyr Leu Asp Ile Leu Gly
        845                 850

(2) INFORMATION FOR SEQ ID NO:8:

(i) SEQUENCE CHARACTERISTICS:
        (A) LENGTH: 2940 bases
        (B) TYPE: nucleic acid
        (C) STRANDEDNESS: double
        (D) TOPOLOGY: linear (xi) SEQUENCE DESCRIPTION: SEQ ID NO:8:

TATAGAATAA CATCCACTTT GCCTTTCTCT CCACAGGTGT CCACTCCCAG          50

GTCCAACTGC ACCTGAATTC CACTGCCTTC CACCAAGCTC TGCAGGATCC         100

CAGAGTCAGG GGTCTGTATC TTCCTGCTGG TGGCTCCAGT TCAGGAACAG         150

TAAACCCTGC TCCGAATATT GCCTCTCACA TCTCGTCAAT CTCCGCGAGG         200

ACTGGGGACC CTGTGACAAG CTTCAGCGCG AACGACCAAC TACCCCGATC         250

ATCAGTTATC CTTAAGGTCT CTTTTGTGTG GTGCGTTCCG GTATGGGGGG         300

GACTGCCGCC AGGTTGGGGG CCGTGATTTT GTTTGTCGTC ATAGTGGGCC         350

TCCATGGGGT CCGCGGCAAA TATGCCTTGG CGGATGCCTC TCTCAAGATG         400

GCCGACCCCA ATCGATTTCG CGGCAAAGAC CTTCCGGTCC TGGACCAGCT         450

GCTCGAGGTA TGCCCTGCAA ATTGTGTCTG CAGCAAGACT GAGATCAATT         500

GCCGGCGGCC GGACGATGGG AACCTCTTCC CCCTCCTGGA AGGGCAGGAT         550

TCAGGGAACA GCAATGGGAA CGCCAATATC AACATCACGG ACATCTCAAG         600

GAATATCACT TCCATACACA TAGAGAACTG GCGCAGTCTT CACACGCTCA         650

ACGCCGTGGA CATGGAGCTC TACACCGGAC TTCAAAAGCT GACCATCAAG         700

AACTCAGGAC TTCGGAGCAT TCAGCCCAGA GCCTTTGCCA AGAACCCCCA         750
```

-continued

| | |
|---|---|
| TTTGCGTTAT ATAAACCTGT CAAGTAACCG GCTCACCACA CTCTCGTGGC | 800 |
| AGCTCTTCCA GACGCTGAGT CTTCGGGAAT TGCAGTTGGA GCAGAACTTT | 850 |
| TTCAACTGCA GCTGTGACAT CCGCTGGATG CAGCTCTGGC AGGAGCAGGG | 900 |
| GGAGGCCAAG CTCAACAGCC AGAACCTCTA CTGCATCAAT GCTGATGGCT | 950 |
| CCCAGCTTCC TCTCTTCCGC ATGAACATCA GTCAGTGTGA CCTTCCTGAG | 1000 |
| ATCAGCGTGA GCCACGTCAA CCTGACCGTA CGAGAGGGTG ACAATGCTGT | 1050 |
| TATCACTTGC AATGGCTCTG GATCACCCCT TCCTGATGTG GACTGGATAG | 1100 |
| TCACTGGGCT GCAGTCCATC AACACTCACC AGACCAATCT GAACTGGACC | 1150 |
| AATGTTCATG CCATCAACTT GACGCTGGTG AATGTGACGA GTGAGGACAA | 1200 |
| TGGCTTCACC CTGACGTGCA TTGCAGAGAA CGTGGTGGGC ATGAGCAATG | 1250 |
| CCAGTGTTGC CCTCACTGTC TACTATCCCC CACGTGTGGT GAGCCTGGAG | 1300 |
| GAGCCTGAGC TGCGCCTGGA GCACTGCATC GAGTTTGTGG TGCGTGGCAA | 1350 |
| CCCCCCACCA ACGCTGCACT GGCTGCACAA TGGGCAGCCT CTGCGGGAGT | 1400 |
| CCAAGATCAT CCATGTGGAA TACTACCAAG AGGGAGAGAT TTCCGAGGGC | 1450 |
| TGCCTGCTCT TCAACAAGCC CACCCACTAC AACAATGGCA ACTATACCCT | 1500 |
| CATTGCCAAA AACCCACTGG GCACAGCCAA CCAGACCATC AATGGCCACT | 1550 |
| TCCTCAAGGA GCCCTTTCCA GAGAGCACGG ATAACTTTAT CTTGTTTGAC | 1600 |
| GAAGTGAGTC CCACACCTCC TATCACTGTG ACCCACAAAC CAGAAGAAGA | 1650 |
| CACTTTTGGG GTATCCATAG CAGTTGGACT TGCTGCTTTT GCCTGTGTCC | 1700 |
| TGTTGGTGGT TCTCTTCGTC ATGATCAACA AATATGGTCG ACGGTCCAAA | 1750 |
| TTTGGAATGA AGGGTCCCGT GGCTGTCATC AGTGGTGAGG AGGACTCAGC | 1800 |
| CAGCCCACTG CACCACATCA ACCACGGCAT CACCACGCCC TCGTCACTGG | 1850 |
| ATGCCGGGCC CGACACTGTG GTCATTGGCA TGACTCGCAT CCCTGTCATT | 1900 |
| GAGAACCCCC AGTACTTCCG TCAGGGACAC AACTGCCACA GCCGGACAC | 1950 |
| GTATGTGCAG CACATTAAGA GGAGAGACAT CGTGCTGAAG CGAGAACTGG | 2000 |
| GTGAGGGAGC CTTTGGAAAG GTCTTCCTGG CCGAGTGCTA CAACCTCAGC | 2050 |
| CCGACCAAGG ACAAGATGCT TGTGGCTGTG AAGGCCCTGA AGGATCCCAC | 2100 |
| CCTGGCTGCC CGGAAGGATT TCCAGAGGGA GGCCGAGCTG CTCACCAACC | 2150 |
| TGCAGCATGA GCACATTGTC AAGTTCTATG GAGTGTGCGG CGATGGGGAC | 2200 |
| CCCCTCATCA TGGTCTTTGA ATACATGAAG CATGGAGACC TGAATAAGTT | 2250 |
| CCTCAGGGCC CATGGGCCAG ATGCAATGAT CCTTGTGGAT GGACAGCCAC | 2300 |
| GCCAGGCCAA GGGTGAGCTG GGGCTCTCCC AAATGCTCCA CATTGCCAGT | 2350 |
| CAGATCGCCT CGGGTATGGT GTACCTGGCC TCCCAGCACT TGTGCACCG | 2400 |
| AGACCTGGCC ACCAGGAACT GCCTGGTTGG AGCGAATCTG CTAGTGAAGA | 2450 |
| TTGGGGACTT CGGCATGTCC AGAGATGTCT ACAGCACGGA TTATTACAGG | 2500 |
| GTGGGAGGAC ACACCATGCT CCCCATTCGC TGGATGCCTC CTGAAAGCAT | 2550 |
| CATGTACCGG AAGTTCACTA CAGAGAGTGA TGTATGGAGC TTCGGGGTGA | 2600 |
| TCCTCTGGGA GATCTTCACC TATGGAAAGC AGCCATGGTT CCAACTCTCA | 2650 |
| AACACGGAGG TCATTGAGTG CATTACCCAA GGTCGTGTTT TGGAGCGGCC | 2700 |
| CCGAGTCTGC CCCAAAGAGG TGTACGATGT CATGCTGGGG TGCTGGCAGA | 2750 |

```
GGGAACCACA GCAGCGGTTG AACATCAAGG AGATCTACAA AATCCTCCAT         2800

GCTTTGGGGA AGGCCACCCC AATCTACCTG GACATTCTTG GCTAGTGGTG         2850

GCTGGTGGTC ATGAATTAAT TCAATCGATG GCCGCCATGG CCCAACTTGT         2900

TTATTGCAGC TTATAATGGT TACAAATAAA GCAATAGCAT                    2940

(2) INFORMATION FOR SEQ ID NO:9:

(i) SEQUENCE CHARACTERISTICS:
        (A) LENGTH: 5141 bases
        (B) TYPE: nucleic acid
        (C) STRANDEDNESS: double
        (D) TOPOLOGY: linear (xi) SEQUENCE DESCRIPTION: SEQ ID NO:9:

TTCGAGCTCG CCCGACATTG ATTATTGACT AGAGTCGATC GACAGCTGTG           50

GAATGTGTGT CAGTTAGGGT GTGGAAAGTC CCCAGGCTCC CCAGCAGGCA          100

GAAGTATGCA AAGCATGCAT CTCAATTAGT CAGCAACCAG GTGTGGAAAG          150

TCCCCAGGCT CCCCAGCAGG CAGAAGTATG CAAAGCATGC ATCTCAATTA          200

GTCAGCAACC ATAGTCCCGC CCCTAACTCC GCCCATCCCG CCCCTAACTC          250

CGCCCAGTTC CGCCCATTCT CCGCCCCATG GCTGACTAAT TTTTTTTATT          300

TATGCAGAGG CCGAGGCCGC CTCGGCCTCT GAGCTATTCC AGAAGTAGTG          350

AGGAGGCTTT TTTGGAGGCC TAGGCTTTTG CAAAAAGCTA GCTTATCCGG          400

CCGGGAACGG TGCATTGGAA CGCGGATTCC CCGTGCCAAG AGTGACGTAA          450

GTACCGCCTA TAGAGCGATA AGAGGATTTT ATCCCCGCTG CCATCATGGT          500

TCGACCATTG AACTGCATCG TCGCCGTGTC CCAAAATATG GGGATTGGCA          550

AGAACGGAGA CCTACCCTGG CCTCCGCTCA GGAACGAGTT CAAGTACTTC          600

CAAAGAATGA CCACAACCTC TTCAGTGGAA GGTAAACAGA ATCTGGTGAT          650

TATGGGTAGG AAAACCTGGT TCTCCATTCC TGAGAAGAAT CGACCTTTAA          700

AGGACAGAAT TAATATAGTT CTCAGTAGAG AACTCAAAGA ACCACCACGA          750

GGAGCTCATT TTCTTGCCAA AAGTTTGGAT GATGCCTTAA GACTTATTGA          800

ACAACCGGAA TTGGCAAGTA AAGTAGACAT GGTTTGGATA GTCGGAGGCA          850

GTTCTGTTTA CCAGGAAGCC ATGAATCAAC CAGGCCACCT TAGACTCTTT          900

GTGACAAGGA TCATGCAGGA ATTTGAAAGT GACACGTTTT TCCCAGAAAT          950

TGATTTGGGG AAATATAAAC CTCTCCCAGA ATACCCAGGC GTCCTCTCTG         1000

AGGTCCAGGA GGAAAAAGGC ATCAAGTATA AGTTTGAAGT CTACGAGAAG         1050

AAAGACTAAC AGGAAGATGC TTTCAAGTTC TCTGCTCCCC TCCTAAAGCT         1100

ATGCATTTTT ATAAGACCAT GGGACTTTTG CTGGCTTTAG ATCCCCTTGG         1150

CTTCGTTAGA ACGCGGCTAC AATTAATACA TAACCTTATG TATCATACAC         1200

ATACGATTTA GGTGACACTA TAGATAACAT CCACTTTGCC TTTCTCTCCA         1250

CAGGTGTCCA CTCCCAGGTC CAACTGCACC TCGGTTCTAA GCTTCTGCAG         1300

GTCGACTCTA GAGGATCCCC GGGAATTCA ATCGATGGCC GCCATGGCCC          1350

AACTTGTTTA TTGCAGCTTA TAATGGTTAC AAATAAAGCA ATAGCATCAC         1400

AAATTTCACA AATAAAGCAT TTTTTTCACT GCATTCTAGT TGTGGTTTGT         1450

CCAAACTCAT CAATGTATCT TATCATGTCT GGATCGATCG GGAATTAATT         1500

CGGCGCAGCA CCATGGCCTG AAATAACCTC TGAAAGAGGA ACTTGGTTAG         1550
```

```
GTACCTTCTG AGGCGGAAAG AACCAGCTGT GGAATGTGTG TCAGTTAGGG        1600

TGTGGAAAGT CCCCAGGCTC CCCAGCAGGC AGAAGTATGC AAAGCATGCA        1650

TCTCAATTAG TCAGCAACCA GGTGTGGAAA GTCCCCAGGC TCCCCAGCAG        1700

GCAGAAGTAT GCAAAGCATG CATCTCAATT AGTCAGCAAC CATAGTCCCG        1750

CCCCTAACTC CGCCCATCCC GCCCCTAACT CCGCCCAGTT CCGCCCATTC        1800

TCCGCCCCAT GGCTGACTAA TTTTTTTTAT TTATGCAGAG GCCGAGGCCG        1850

CCTCGGCCTC TGAGCTATTC CAGAAGTAGT GAGGAGGCTT TTTTGGAGGC        1900

CTAGGCTTTT GCAAAAAGCT GTTACCTCGA GCGGCCGCTT AATTAAGGCG        1950

CGCCATTTAA ATCCTGCAGG TAACAGCTTG GCACTGGCCG TCGTTTTACA        2000

ACGTCGTGAC TGGGAAAACC CTGGCGTTAC CCAACTTAAT CGCCTTGCAG        2050

CACATCCCCC TTCGCCAGC TGGCGTAATA GCGAAGAGGC CCGCACCGAT         2100

CGCCCTTCCC AACAGTTGCG TAGCCTGAAT GGCGAATGGC GCCTGATGCG        2150

GTATTTTCTC CTTACGCATC TGTGCGGTAT TTCACACCGC ATACGTCAAA        2200

GCAACCATAG TACGCGCCCT GTAGCGGCGC ATTAAGCGCG GCGGGTGTGG        2250

TGGTTACGCG CAGCGTGACC GCTACACTTG CCAGCGCCCT AGCGCCCGCT        2300

CCTTTCGCTT TCTTCCCTTC CTTTCTCGCC ACGTTCGCCG GCTTTCCCCG        2350

TCAAGCTCTA AATCGGGGGC TCCCTTTAGG GTTCCGATTT AGTGCTTTAC        2400

GGCACCTCGA CCCCAAAAAA CTTGATTTGG GTGATGGTTC ACGTAGTGGG        2450

CCATCGCCCT GATAGACGGT TTTTCGCCCT TTGACGTTGG AGTCCACGTT        2500

CTTTAATAGT GGACTCTTGT TCCAAACTGG AACAACACTC AACCCTATCT        2550

CGGGCTATTC TTTTGATTTA TAAGGGATTT TGCCGATTTC GGCCTATTGG        2600

TTAAAAAATG AGCTGATTTA ACAAAAATTT AACGCGAATT TTAACAAAAT        2650

ATTAACGTTT ACAATTTTAT GGTGCACTCT CAGTACAATC TGCTCTGATG        2700

CCGCATAGTT AAGCCAACTC CGCTATCGCT ACGTGACTGG GTCATGGCTG        2750

CGCCCCGACA CCCGCCAACA CCCGCTGACG CGCCCTGACG GGCTTGTCTG        2800

CTCCCGGCAT CCGCTTACAG ACAAGCTGTG ACCGTCTCCG GGAGCTGCAT        2850

GTGTCAGAGG TTTTCACCGT CATCACCGAA ACGCGCGAGG CAGTATTCTT        2900

GAAGACGAAA GGGCCTCGTG ATACGCCTAT TTTTATAGGT TAATGTCATG        2950

ATAATAATGG TTTCTTAGAC GTCAGGTGGC ACTTTTCGGG GAAATGTGCG        3000

CGGAACCCCT ATTTGTTTAT TTTTCTAAAT ACATTCAAAT ATGTATCCGC        3050

TCATGAGACA ATAACCCTGA TAAATGCTTC AATAATATTG AAAAAGGAAG        3100

AGTATGAGTA TTCAACATTT CCGTGTCGCC CTTATTCCCT TTTTTGCGGC        3150

ATTTTGCCTT CCTGTTTTTG CTCACCCAGA AACGCTGGTG AAAGTAAAAG        3200

ATGCTGAAGA TCAGTTGGGT GCACGAGTGG GTTACATCGA ACTGGATCTC        3250

AACAGCGGTA AGATCCTTGA GAGTTTTCGC CCCGAAGAAC GTTTTCCAAT        3300

GATGAGCACT TTTAAAGTTC TGCTATGTGG CGCGGTATTA TCCCGTGATG        3350

ACGCCGGGCA AGAGCAACTC GGTCGCCGCA TACACTATTC TCAGAATGAC        3400

TTGGTTGAGT ACTCACCAGT CACAGAAAAG CATCTTACGG ATGGCATGAC        3450

AGTAAGAGAA TTATGCAGTG CTGCCATAAC CATGAGTGAT AACACTGCGG        3500

CCAACTTACT TCTGACAACG ATCGGAGGAC CGAAGGAGCT AACCGCTTTT        3550
```

```
TTGCACAACA TGGGGGATCA TGTAACTCGC CTTGATCGTT GGGAACCGGA       3600

GCTGAATGAA GCCATACCAA ACGACGAGCG TGACACCACG ATGCCAGCAG       3650

CAATGGCAAC AACGTTGCGC AAACTATTAA CTGGCGAACT ACTTACTCTA       3700

GCTTCCCGGC AACAATTAAT AGACTGGATG GAGGCGGATA AAGTTGCAGG       3750

ACCACTTCTG CGCTCGGCCC TTCCGGCTGG CTGGTTTATT GCTGATAAAT       3800

CTGGAGCCGG TGAGCGTGGG TCTCGCGGTA TCATTGCAGC ACTGGGGCCA       3850

GATGGTAAGC CCTCCCGTAT CGTAGTTATC TACACGACGG GGAGTCAGGC       3900

AACTATGGAT GAACGAAATA GACAGATCGC TGAGATAGGT GCCTCACTGA       3950

TTAAGCATTG GTAACTGTCA GACCAAGTTT ACTCATATAT ACTTTAGATT       4000

GATTTAAAAC TTCATTTTTA ATTTAAAAGG ATCTAGGTGA AGATCCTTTT       4050

TGATAATCTC ATGACCAAAA TCCCTTAACG TGAGTTTTCG TTCCACTGAG       4100

CGTCAGACCC CGTAGAAAAG ATCAAAGGAT CTTCTTGAGA TCCTTTTTTT       4150

CTGCGCGTAA TCTGCTGCTT GCAAACAAAA AAACCACCGC TACCAGCGGT       4200

GGTTTGTTTG CCGGATCAAG AGCTACCAAC TCTTTTTCCG AAGGTAACTG       4250

GCTTCAGCAG AGCGCAGATA CCAAATACTG TCCTTCTAGT GTAGCCGTAG       4300

TTAGGCCACC ACTTCAAGAA CTCTGTAGCA CCGCCTACAT ACCTCGCTCT       4350

GCTAATCCTG TTACCAGTGG CTGCTGCCAG TGGCGATAAG TCGTGTCTTA       4400

CCGGGTTGGA CTCAAGACGA TAGTTACCGG ATAAGGCGCA GCGGTCGGGC       4450

TGAACGGGGG GTTCGTGCAC ACAGCCCAGC TTGGAGCGAA CGACCTACAC       4500

CGAACTGAGA TACCTACAGC GTGAGCATTG AGAAAGCGCC ACGCTTCCCG       4550

AAGGGAGAAA GGCGGACAGG TATCCGGTAA GCGGCAGGGT CGGAACAGGA       4600

GAGCGCACGA GGGAGCTTCC AGGGGGAAAC GCCTGGTATC TTTATAGTCC       4650

TGTCGGGTTT CGCCACCTCT GACTTGAGCG TCGATTTTTG TGATGCTCGT       4700

CAGGGGGGCG GAGCCTATGG AAAAACGCCA GCAACGCGGC CTTTTTACGG       4750

TTCCTGGCCT TTTGCTGGCC TTTTGCTCAC ATGTTCTTTC CTGCGTTATC       4800

CCCTGATTCT GTGGATAACC GTATTACCGC CTTTGAGTGA GCTGATACCG       4850

CTCGCCGCAG CCGAACGACC GAGCGCAGCG AGTCAGTGAG CGAGGAAGCG       4900

GAAGAGCGCC CAATACGCAA ACCGCCTCTC CCCGCGCGTT GGCCGATTCA       4950

TTAATCCAGC TGGCACGACA GGTTTCCCGA CTGGAAAGCG GGCAGTGAGC       5000

GCAACGCAAT TAATGTGAGT TACCTCACTC ATTAGGCACC CCAGGCTTTA       5050

CACTTTATGC TTCCGGCTCG TATGTTGTGT GGAATTGTGA GCGGATAACA       5100

ATTTCACACA GGAAACAGCT ATGACCATGA TTACGAATTA A               5141

(2) INFORMATION FOR SEQ ID NO:10:

(i) SEQUENCE CHARACTERISTICS:
        (A) LENGTH: 103 bases
        (B) TYPE: nucleic acid
        (C) STRANDEDNESS: single
        (D) TOPOLOGY: linear (xi) SEQUENCE DESCRIPTION: SEQ ID NO:10:

TGCAGCAAGG GCTACTGCCA CACTCGAGCT GCGCAGATGC TAGCCTCAAG       50

ATGGCTGATC CAAATCGATT CCGCGGCAAA GATCTTCCGG TCCTGTAGAA      100
```

-continued

```
GCT                                                                     103

(2) INFORMATION FOR SEQ ID NO:11:

(i) SEQUENCE CHARACTERISTICS:
        (A) LENGTH: 103 bases
        (B) TYPE: nucleic acid
        (C) STRANDEDNESS: single
        (D) TOPOLOGY: linear (xi) SEQUENCE DESCRIPTION: SEQ ID NO:11:

AGCTTCTACA GGACCGGAAG ATCTTTGCCG CGGAATCGAT TTGGATCAGC                    50

CATCTTGAGG CTAGCATCTG CGCAGCTCGA GTGTGGCAGT AGCCCTTGCT                   100

GCA                                                                     103
```

We claim:

1. An assay for measuring autophosphorylation of a Her2 tyrosine kinase receptor comprising the steps of:

(a) coating a first solid phase with a homogeneous population of eukaryotic cells so that the cells adhere to the first solid phase, wherein, positioned in their membranes, the cells have a receptor construct comprising a flag polypeptide and the tyrosine kinase receptor, wherein said tyrosine kinase receptor comprises the Her2 receptor;

(b) exposing the adhering cells to an analytewhich is known to contain or is (c) solubilizing the adhering cells, thereby releasing cell lysate therefrom;

(d) coating a second solid phase with a capture agent which binds specifically to the flag polypeptide so that the capture agent adheres to the second solid phase;

(e) exposing the adhering capture agent to the cell lysate obtained in step (c) so that the receptor construct adheres to the second solid phase;

(f) washing the second solid phase so as to remove unbound cell lysate;

(g) exposing the adhering receptor construct to an anti-phosphotyrosine antibody which identifies phosphorylated tyrosine residues in the tyrosine kinase receptor; and (h) measuring binding of the anti-phosphotyrosine antibody to the adhering receptor construct, wherein the amount of anti-phosphotyrosine antibody binding to the adhering receptor construct is proportional to the amount of autophosphorylation of said tyrosine kinase receptor.

2. The method of claim 1 wherein the cells are transformed with nucleic acid encoding the receptor construct prior to step (a).

3. The method of claim 1 wherein the cells comprise a mammalian cell line.

4. The method of claim 1 wherein the capture agent comprises a capture antibody.

5. The method of claim 4 wherein the capture antibody comprises an affinity purified polyclonal antibody.

6. The method of claim 4 wherein the capture antibody comprises a monoclonal antibody.

7. The method of claim 1 wherein the first solid phase comprises a well of a first assay plate.

8. The method of claim 7 wherein the first assay plate is a microtiter plate.

9. The method of claim 7 wherein between about $1 \times 10^4$ to $3 \times 10^5$ cells are added to the well in step (a).

10. The method of claim 1 wherein the second solid phase comprises a well of a second assay plate.

11. The method of claim 10 wherein the second assay plate comprises a microtiter plate.

12. The method of claim 1 wherein the cell lysate is not concentrated or clarified prior to step (e).

13. The method of claim 7 wherein step (c) comprises adding a lysis buffer to the well of the first assay plate and gently agitating the first assay plate.

14. The method of claim 13 wherein the lysis buffer comprises a solubilizing detergent.

15. The method of claim 1 wherein the anti-phosphotyrosine antibody is labelled.

16. The method of claim 15 wherein the label is added to the anti-phosphotyrosine antibody after step (g).

17. The method of claim 15 wherein the label is added to the anti-phosphotyrosine antibody prior to step (g).

18. The method of claim 15 wherein the label comprises a non-radioactive label.

19. The method of claim 18 wherein the label comprises an enzyme.

20. The method of claim 19 comprising exposing the enzyme to a color reagent and determining the color change of the color reagent in step (h).

21. The method of claim 1 wherein the flag polypeptide is fused to the amino terminus of the tyrosine kinase receptor.

22. The method of claim 1 wherein the flag polypeptide is fused to the carboxyl terminus of the tyrosine kinase receptor.

23. The method of claim 1 wherein the analyte comprises a ligand for the tyrosine kinase receptor.

24. The method of claim 23 wherein the ligand comprises an agonist for the tyrosine kinase receptor.

25. The method of claim 23 wherein the ligand comprises an antagonist for the tyrosine kinase receptor.

26. The method of claim 25 wherein the antagonist competitively inhibits binding or activation of the tyrosine kinase receptor by an agonist thereto and step (b) is followed by a step wherein the adhering cells are exposed to the agonist.

27. The method of claim 1 wherein the analyte is a composition which comprises an antagonist and an agonist for the receptor and wherein the amount of anti-phosphotyrosine antibody binding to the adhering receptor construct directly correlates with the ability of the antagonist to bind to the agonist and thereby reduce activation of the tyrosine kinase receptor by the agonist.

28. The method of claim 1 wherein a block buffer is added to the second solid phase following step (d).

29. An assay for measuring autophosphorylation of a Her2 tyrosine kinase receptor comprising the steps of:
  (a) coating a well of a first assay plate with a homogeneous population of adherent cells so that the cells adhere to the well, wherein the cells have a tyrosine kinase receptor positioned in the cell membrane thereof, wherein said tyrosine kinase receptor comprises the Her2 receptor;
  (b) exposing the adhering cells to an analyte which is known to contain or is suspected of containing a ligand for the tyrosine kinase receptor;
  (c) solubilizing the adhering cells thereby releasing cell lysate therefrom;
  (d) coating a well of a second assay plate with a capture agent which binds specifically to the tyrosine kinase receptor so that the capture agent adheres to the well;
  (e) exposing the cell lysate obtained in step (c) to the adhering capture agent so that the tyrosine kinase receptor adheres to the well;
  (f) washing the well so as to remove unbound cell lysate;
  (g) exposing the adhering tyrosine kinase receptor to an anti-phosphotyrosine antibody which binds selectively to phosphorylated tyrosine residues in the tyrosine kinase receptor; and
  (h) measuring binding of the anti-phosphotyrosine antibody to the adhering tyrosine kinase receptor, wherein the amount of anti-phosphotyrosine antibody binding to the adhering tyrosine kinase receptor is proportional to the amount of autophosphorylation of said tyrosine kinase receptor.

* * * * *